(12) United States Patent
Roubos et al.

(10) Patent No.: US 7,888,489 B2
(45) Date of Patent: Feb. 15, 2011

(54) METHOD FOR PRODUCING A COMPOUND OF INTEREST IN A FILAMENTOUS FUNGAL CELL

(75) Inventors: Johannes Andries Roubos, Pijnacker (NL); Serge Petrus Donkers, Hellevoetsluis (NL); Hein Stam, Huizen (NL); Noël Nicolaas Maria Elisabeth Van Peij, Delft (NL)

(73) Assignee: DSM IP Assets B.V., Heerlen (NL)

( * ) Notice: Subject to any disclaimer, the term of this patent is extended or adjusted under 35 U.S.C. 154(b) by 641 days.

(21) Appl. No.: 11/795,824

(22) PCT Filed: Jan. 24, 2006

(86) PCT No.: PCT/EP2006/050398

§ 371 (c)(1), (2), (4) Date: Oct. 3, 2007

(87) PCT Pub. No.: WO2006/077258

PCT Pub. Date: Jul. 27, 2006

(65) Prior Publication Data

US 2008/0118965 A1    May 22, 2008

(30) Foreign Application Priority Data

Jan. 24, 2005    (EP) ................... 05100408

(51) Int. Cl.
*C12N 15/11* (2006.01)
*C12N 1/00* (2006.01)
*C12Q 1/68* (2006.01)

(52) U.S. Cl. ............ 536/23.1; 435/6; 435/254.1

(58) Field of Classification Search ............ None
See application file for complete search history.

(56) References Cited

U.S. PATENT DOCUMENTS

| 2004/0005600 A1 | 1/2004 | Angov et al. |
| 2004/0161840 A1 | 8/2004 | Contreras et al. |

FOREIGN PATENT DOCUMENTS

| EP | 1 231 272 A2 | 8/2002 |
| EP | 1 231 272 A3 | 8/2002 |
| WO | 03/070957 A2 | 8/2003 |
| WO | 03/070957 A3 | 8/2003 |
| WO | 03/085114 A1 | 10/2003 |

OTHER PUBLICATIONS

COmeron et al. Selective and mutational patterns associated with gene expression in humans: influences on synonymous composition and intron presence. Genetics. Jul. 2004;167(3):1293-304.*
International Search Report for PCT/EP2006/050398, all pages, mailed Jun. 19, 2006.

* cited by examiner

*Primary Examiner*—Michele K Joike
(74) *Attorney, Agent, or Firm*—Nixon & Vanderhye

(57) ABSTRACT

The invention relates to a nucleotide sequence comprising; a synonymous nucleotide coding sequence with optimized codon frequency such that a native codon has been exchanged with a synonymous codon, the synonymous codon encoding the same amino acid as the native codon and having a higher frequency in codon usage as defined in Table 1 than the native codon; and optionally the nucleotide sequence comprises control sequences such as; one translational termination sequence orientated in 5' towards 3' direction selected from the following list of sequences; TAAG, TAGA and TAAA, preferably TAAA, and/or one translational initiator coding sequence orientated in 5' towards 3' direction selected from the following list of sequences; gctnccyyc (SEQ ID NO:20), using ambiguity codes for nucleotides; v (A/C/G); n (A/C/G/T), preferably 5'-GCT TCC TTC-3' (SEQ ID NO:21). The invention further relates to a consensus translational initiator sequence; 5'-mwChkyCAmv-3' (SEQ ID NO:16), preferably the translational initiator sequence is selected from the list consisting of; 5'-mwChkyCAAA-3' (SEQ ID NO:17), 5'-mwChkyCACA-3' (SEQ ID NO:18), and 5'-mwChky-CAAG-3' (SEQ ID NO:19).

19 Claims, 10 Drawing Sheets

FIG. 6 (continued)

SEQUENCE LISTING

```
<160> NUMBER OF SEQ ID NOS: 194

<210> SEQ ID NO 1
<211> LENGTH: 1056
<212> TYPE: DNA
<213> ORGANISM: Aspergillus oryzae
<220> FEATURE:
<221> NAME/KEY: exon
<222> LOCATION: (1)..(79)
<220> FEATURE:
<221> NAME/KEY: intron
<222> LOCATION: (80)..(142)
<220> FEATURE:
```

```
<221> NAME/KEY: exon
<222> LOCATION: (143)..(308)
<220> FEATURE:
<221> NAME/KEY: intron
<222> LOCATION: (309)..(362)
<220> FEATURE:
<221> NAME/KEY: exon
<222> LOCATION: (363)..(699)
<220> FEATURE:
<221> NAME/KEY: intron
<222> LOCATION: (700)..(750)
<220> FEATURE:
<221> NAME/KEY: exon
<222> LOCATION: (751)..(1056)

<400> SEQUENCE: 1 atg ttt agt ctc gcg cga ttg ggg acc gtt gca ggt cta ttt tta ctg      48
Met Phe Ser Leu Ala Arg Leu Gly Thr Val Ala Gly Leu Phe Leu Leu
 1               5                  10                  15 gct cag gct gcc ccg gct tca ctg cgc aga g gtatgtttat tttctccaca      99
Ala Gln Ala Ala Pro Ala Ser Leu Arg Arg
             20                  25 acttgtaaca cagcattcgc ttgagccaga ctgacggatt tag at gtc agc tct       153
                                                Asp Val Ser Ser
                                                            30 tcc ctt ctc aat aac ctg gat ctc ttt gca cag tac agc gcc gcc gca      201
Ser Leu Leu Asn Asn Leu Asp Leu Phe Ala Gln Tyr Ser Ala Ala Ala
                 35                  40                  45 tac tgt gat gag aac ctg aac tct acg ggg acc aag ttg aca tgc tct      249
Tyr Cys Asp Glu Asn Leu Asn Ser Thr Gly Thr Lys Leu Thr Cys Ser
             50                  55                  60 gtt ggc aac tgt cct ttg gta gaa gcg gcc tct acc caa tca ttg gat      297
Val Gly Asn Cys Pro Leu Val Glu Ala Ala Ser Thr Gln Ser Leu Asp
 65                  70                  75 gaa ttc aac ga gtaagtcacc gcaaatatac aattctagtt cataagcaac          348
Glu Phe Asn Glu
             80 tactgacaac tcag a tcg tca tcc tac ggc aac ccc gcc ggg tac ctc gcc   399
                 Ser Ser Ser Tyr Gly Asn Pro Ala Gly Tyr Leu Ala
                                 85                  90 gct gat gag act aac aag ctc cta gtc ctg tcc ttc cgg ggt agc gct      447
Ala Asp Glu Thr Asn Lys Leu Leu Val Leu Ser Phe Arg Gly Ser Ala
 95                 100                 105                 110 gac ttg gcc aat tgg gtc gcc aac ctg aat ttt ggt ctc gag gat gcc      495
Asp Leu Ala Asn Trp Val Ala Asn Leu Asn Phe Gly Leu Glu Asp Ala
                115                 120                 125 agc gat ctg tgt tct ggg tgc gaa gtg cac agc ggc ttc tgg aag gca      543
Ser Asp Leu Cys Ser Gly Cys Glu Val His Ser Gly Phe Trp Lys Ala
            130                 135                 140 tgg agt gaa atc gcc gac acc atc act tcc aaa gtg gaa tca gct ttg      591
Trp Ser Glu Ile Ala Asp Thr Ile Thr Ser Lys Val Glu Ser Ala Leu
        145                 150                 155 tcg gat cat tcc gat tat tcc ttg gtc ttg acc gga cat agt tac ggc      639
Ser Asp His Ser Asp Tyr Ser Leu Val Leu Thr Gly His Ser Tyr Gly
    160                 165                 170 gct gcg ctg gca gcc ctc gca gcg act gct ctg cgg aac tcc ggc cat      687
Ala Ala Leu Ala Ala Leu Ala Ala Thr Ala Leu Arg Asn Ser Gly His
175                 180                 185                 190 agt gtt gag ctg gtaagttatc ctcattttgt aagtgacggt gcgccaaatc         739
Ser Val Glu Leu tgaccaaata g tac aac tac ggt caa cct cga ctt gga aac gag gca ttg    789
             Tyr Asn Tyr Gly Gln Pro Arg Leu Gly Asn Glu Ala Leu
                 195                 200                 205
```

```
gca aca tat atc acg gac caa aac aag ggt ggc aac tat cgc gtt acg    837
Ala Thr Tyr Ile Thr Asp Gln Asn Lys Gly Gly Asn Tyr Arg Val Thr
        210                 215                 220 cac act aat gat att gtg cct aaa ctg cca ccc acg ctg ctc ggg tat    885
His Thr Asn Asp Ile Val Pro Lys Leu Pro Pro Thr Leu Leu Gly Tyr
    225                 230                 235 cac cac ttc agc cca gag tac tat atc agc agc gcc gac gag gca acg    933
His His Phe Ser Pro Glu Tyr Tyr Ile Ser Ser Ala Asp Glu Ala Thr
240                 245                 250                 255 gtg acc acc act gat gtg act gag gtt acg gga atc gat gct acg ggc    981
Val Thr Thr Thr Asp Val Thr Glu Val Thr Gly Ile Asp Ala Thr Gly
                260                 265                 270 ggt aat gat gga acc gac gga act agc atc gat gct cat cgg tgg tac   1029
Gly Asn Asp Gly Thr Asp Gly Thr Ser Ile Asp Ala His Arg Trp Tyr
            275                 280                 285 ttt att tat att agc gaa tgt tca tag                                1056
Phe Ile Tyr Ile Ser Glu Cys Ser
            290                 295

<210> SEQ ID NO 2
<211> LENGTH: 888
<212> TYPE: DNA
<213> ORGANISM: Aspergillus oryzae

<400> SEQUENCE: 2
atgtttagtc tcgcgcgatt ggggaccgtt gcaggtctat ttttactggc tcaggctgcc     60
ccggcttcac tgcgcagaga gtcagctct tcccttctca ataacctgga tctctttgca    120
cagtacagcg ccgccgcata ctgtgatgag aacctgaact ctacggggac caagttgaca    180
tgctctgttg gcaactgtcc tttggtagaa gcggcctcta cccaatcatt ggatgaattc    240
aacgaatcgt catcctacgg caaccccgcc gggtacctcg ccgctgatga gactaacaag    300
ctcctagtcc tgtccttccg gggtagcgct gacttggcca attgggtcgc caacctgaat    360
tttggtctcg aggatgccag cgatctgtgt tctgggtgcg aagtgcacag cggcttctgg    420
aaggcatgga gtgaaatcgc cgacaccatc acttccaaag tggaatcagc tttgtcggat    480
cattccgatt attccttggt cttgaccgga catagttacg gcgctgcgct ggcagccctc    540
gcagcgactc tctgcggaa ctccggccat agtgttgagc tgtacaacta cggtcaacct    600
cgacttggaa acgaggcatt ggcaacatat atcacggacc aaaacaaggg tggcaactat    660
cgcgttacgc acactaatga tattgtgcct aaactgccac ccacgctgct cgggtatcac    720
cacttcagcc cagagtacta tatcagcagc gccgacgagg caacggtgac caccactgat    780
gtgactgagg ttacgggaat cgatgctacg ggcggtaatg atggaaccga cggaactagc    840
atcgatgctc atcggtggta ctttatttat attagcgaat gttcatag              888

<210> SEQ ID NO 3
<211> LENGTH: 295
<212> TYPE: PRT
<213> ORGANISM: Aspergillus oryzae

<400> SEQUENCE: 3

Met Phe Ser Leu Ala Arg Leu Gly Thr Val Ala Gly Leu Phe Leu Leu
1               5                   10                  15

Ala Gln Ala Ala Pro Ala Ser Leu Arg Arg Asp Val Ser Ser Ser Leu
            20                  25                  30

Leu Asn Asn Leu Asp Leu Phe Ala Gln Tyr Ser Ala Ala Ala Tyr Cys
        35                  40                  45
```

```
Asp Glu Asn Leu Asn Ser Thr Gly Thr Lys Leu Thr Cys Ser Val Gly
 50                  55                  60

Asn Cys Pro Leu Val Glu Ala Ala Ser Thr Gln Ser Leu Asp Glu Phe
 65                  70                  75                  80

Asn Glu Ser Ser Ser Tyr Gly Asn Pro Ala Gly Tyr Leu Ala Ala Asp
                 85                  90                  95

Glu Thr Asn Lys Leu Leu Val Leu Ser Phe Arg Gly Ser Ala Asp Leu
            100                 105                 110

Ala Asn Trp Val Ala Asn Leu Asn Phe Gly Leu Glu Asp Ala Ser Asp
        115                 120                 125

Leu Cys Ser Gly Cys Glu Val His Ser Gly Phe Trp Lys Ala Trp Ser
130                 135                 140

Glu Ile Ala Asp Thr Ile Thr Ser Lys Val Glu Ser Ala Leu Ser Asp
145                 150                 155                 160

His Ser Asp Tyr Ser Leu Val Leu Thr Gly His Ser Tyr Gly Ala Ala
                165                 170                 175

Leu Ala Ala Leu Ala Ala Thr Ala Leu Arg Asn Ser Gly His Ser Val
            180                 185                 190

Glu Leu Tyr Asn Tyr Gly Gln Pro Arg Leu Gly Asn Glu Ala Leu Ala
        195                 200                 205

Thr Tyr Ile Thr Asp Gln Asn Lys Gly Gly Asn Tyr Arg Val Thr His
    210                 215                 220

Thr Asn Asp Ile Val Pro Lys Leu Pro Pro Thr Leu Leu Gly Tyr His
225                 230                 235                 240

His Phe Ser Pro Glu Tyr Tyr Ile Ser Ser Ala Asp Glu Ala Thr Val
                245                 250                 255

Thr Thr Thr Asp Val Thr Glu Val Thr Gly Ile Asp Ala Thr Gly Gly
            260                 265                 270

Asn Asp Gly Thr Asp Gly Thr Ser Ile Asp Ala His Arg Trp Tyr Phe
        275                 280                 285

Ile Tyr Ile Ser Glu Cys Ser
    290                 295

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agcatcatta cacctcagca atgtttagtc tcgcgcgatt gg                          42

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggattgattg tacgtactat gaac                                              24

<210> SEQ ID NO 6
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 6
gcatcccagg ccagtgaggc cag                                           23

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccaatcgcgc gagactaaac attgctgagg tgtaatgatg ctgg                    44

<210> SEQ ID NO 8
<211> LENGTH: 1263
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Recombinant fusion construct, generated by PCR,
      of a promoter fragment and a gene fragment
<220> FEATURE:
<221> NAME/KEY: promoter
<222> LOCATION: (1)...(204)
<220> FEATURE:
<221> NAME/KEY: gene
<222> LOCATION: (205)...(1263)

<400> SEQUENCE: 8
gaattcaagc tagatgctaa gcgatattgc atggcaatat gtgttgatgc atgtgcttct    60
tccttcagct tcccctcgtg cagatgaggt ttggctataa attgaagtgg ttggtcgggg   120
ttccgtgagg ggctgaagtg cttcctccct tttagacgca actgagagcc tgagcttcat   180
ccccagcatc attacacctc agcaatgttt agtctcgcgc gattggggac cgttgcaggt   240
ctatttttac tggctcaggc tgccccggct tcactgcgca gaggtatgtt tattttctcc   300
acaacttgta acacagcatt cgcttgagcc agactgacgg atttagatgt cagctcttcc   360
cttctcaata acctggatct cttttgcacag tacagcgccg ccgcatactg tgatgagaac   420
ctgaactcta cggggaccaa gttgacatgc tctgttggca actgtccttt ggtagaagcg   480
gcctctaccc aatcattgga tgaattcaac gagtaagtca ccgcaaatat acaattctag   540
ttcataagca actactgaca actcagatcg tcatcctacg gcaaccccgc cgggtacctc   600
gccgctgatg agactaacaa gctcctagtc ctgtccttcc ggggtagcgc tgacttggcc   660
aattgggtcg ccaacctgaa ttttggtctc gaggatgcca gcgatctgtg ttctgggtgc   720
gaagtgcaca gcggcttctg gaaggcatgg agtgaaatcg ccgacaccat cacttccaaa   780
gtggaatcag ctttgtcgga tcattccgat tattccttgg tcttgaccgg acatagttac   840
ggcgctgcgc tggcagccct cgcagcgact gctctgcgga actccggcca tagtgttgag   900
ctggtaagtt atcctcattt tgtaagtgac ggtgcgccaa atctgaccaa atagtacaac   960
tacggtcaac ctcgacttgg aaacgaggca ttggcaacat atatcacgga ccaaaacaag  1020
ggtggcaact atcgcgttac gcacactaat gatattgtgc ctaaactgcc acccacgctg  1080
ctcgggtatc accacttcag cccagagtac tatatcagca gcgccgacga ggcaacggtg  1140
```

-continued

```
accaccactg atgtgactga ggttacggga atcgatgcta cgggcggtaa tgatggaacc      1200
gacggaacta gcatcgatgc tcatcggtgg tactttattt atattagcga atgttcatag      1260
tac                                                                   1263
```

<210> SEQ ID NO 9
<211> LENGTH: 507
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Recombinant fusion construct, generated by PCR,
    of a promoter fragment and a gene fragment
<220> FEATURE:
<221> NAME/KEY: promoter
<222> LOCATION: (1)..(204)
<220> FEATURE:
<221> NAME/KEY: gene
<222> LOCATION: (205)..(507)

<400> SEQUENCE: 9

```
gaattcaagc tagatgctaa gcgatattgc atggcaatat gtgttgatgc atgtgcttct       60
tccttcagct tcccctcgtg cagatgaggt ttggctataa attgaagtgg ttggtcgggg      120
ttccgtgagg ggctgaagtg cttcctccct tttagacgca actgagagcc tgagcttcat      180
ccccagcatc attacaccgt caaaatgttt agtctcgcgc gattggggac cgttgcaggt      240 ctattttttac tggctcaggc tgccccggct tcactgcgca gaggtatgtt tattttctcc      300
acaacttgta acacagcatt cgcttgagcc agactgacgg atttagatgt cagctcttcc      360
cttctcaata acctggatct cttttgcacag tacagcgccg ccgcatactg tgatgagaac      420
ctgaactcta cggggaccaa gttgacatgc tctgttggca actgtccttt ggtagaagcg      480
gcctctaccc aatcattgga tgaattc                                          507
```

<210> SEQ ID NO 10
<211> LENGTH: 507
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Recombinant fusion construct, generated by PCR,
    of a promoter fragment and a gene fragment
<220> FEATURE:
<221> NAME/KEY: promoter
<222> LOCATION: (1)..(204)
<220> FEATURE:
<221> NAME/KEY: gene
<222> LOCATION: (205)..(507)

<400> SEQUENCE: 10

```
gaattcaagc tagatgctaa gcgatattgc atggcaatat gtgttgatgc atgtgcttct       60
tccttcagct tcccctcgtg cagatgaggt ttggctataa attgaagtgg ttggtcgggg      120
ttccgtgagg ggctgaagtg cttcctccct tttagacgca actgagagcc tgagcttcat      180
ccccagcatc attacgcagt caagatgttt agtctcgcgc gattggggac cgttgcaggt      240 ctattttttac tggctcaggc tgccccggct tcactgcgca gaggtatgtt tattttctcc      300
acaacttgta acacagcatt cgcttgagcc agactgacgg atttagatgt cagctcttcc      360
cttctcaata acctggatct cttttgcacag tacagcgccg ccgcatactg tgatgagaac      420
```

```
ctgaactcta cggggaccaa gttgacatgc tctgttggca actgtccttt ggtagaagcg      480
gcctctaccc aatcattgga tgaattc                                         507

<210> SEQ ID NO 11
<211> LENGTH: 1265
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Recombinant fusion construct, generated by PCR,
      of a promoter fragment and a gene fragment
<220> FEATURE:
<221> NAME/KEY: promoter
<222> LOCATION: (1)..(205)
<220> FEATURE:
<221> NAME/KEY: gene
<222> LOCATION: (206)..(1265)

<400> SEQUENCE: 11
ggaattcaag ctagatgcta agcgatattg catggcaata tgtgttgatg catgtgcttc       60
ttccttcagc ttcccctcgt gcagatgagg tttggctata aattgaagtg gttggtcggg      120
gttccgtgag gggctgaagt gcttcctccc ttttagacgc aactgagagc ctgagcttca      180
tccccagcat cattcaccct cagcaatgtt ctctctcgcc cgccttggta ccgtcgctgg      240
tctcttcctt ctcgctcagg ctgccccgc ttccctgcgc cgtggtatgt ttattttctc       300
cacaacttgt aacacagcat tcgcttgagc cagactgacg gatttagacg tctcctcttc      360
ccttctcaac aacctggacc tcttcgctca gtacagcgcc gccgcttact gcgatgagaa      420
cctgaactct accggtacca gttgacctg ctctgttggc aactgccctc ttgtcgaggc       480
ggcctctacc cagtccttgg atgagttcaa cgagtaagtc accgcaaata tacaattcta      540
gttcataagc aactactgac aactcagatc gtcctcctac ggcaacccg ccggttacct       600 cgccgctgac gagactaaca agctcctcgt cctgtccttc cgtggtagcg ctgaccttgc      660
caactgggtc gccaacctga acttcggtct cgaggacgcc agcgatctgt gctctgttg      720 cgaagtccac tccggcttct ggaaggcttg gtctgagatc gccgacacca tcacttccaa      780
ggtggaatcc gctttgtcgg atcactccga ttactccctc gtcttgaccg gtcactcgta      840
cggcgctgcg ctggccgccc tcgccgcgac tgctctgcgt aactccggcc actcggttga      900
gctggtaagt tatcctcatt ttgtaagtga cggtgcgcca aatctgacca aatagtacaa      960
ctacggtcag cctcgccttg gcaacgaggc cctcgccacc tacatcaccg accagaacaa     1020
gggtggcaac taccgcgtta cccacactaa cgacatcgtc cctaagctgc cccccacccct    1080 gctcggttac caccacttca gccccgagta ctacatcagc agcgccgacg aggccaccgt     1140
gaccaccact gacgtgactg aggttaccgg aatcgatgct accggcggta acgatggaac     1200
cgacggaact agcatcgacg ctcaccgttg gtacttcatt tacatttccg aatgctccta     1260
aatac                                                                 1265

<210> SEQ ID NO 12
<211> LENGTH: 1265
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Recombinant fusion construct, generated by PCR,
      of a promoter fragment and a gene fragment
```

<220> FEATURE:
<221> NAME/KEY: promoter
<222> LOCATION: (1)..(205)
<220> FEATURE:
<221> NAME/KEY: gene
<222> LOCATION: (206)..(1265)

<400> SEQUENCE: 12

| | | | | | |
|---|---|---|---|---|---|
| ggaattcaag | ctagatgcta | agcgatattg | catggcaata | tgtgttgatg | catgtgcttc | 60 |
| ttccttcagc | ttcccctcgt | gcagatgagg | tttggctata | aattgaagtg | gttggtcggg | 120 |
| gttccgtgag | gggctgaagt | gcttcctccc | ttttagacgc | aactgagagc | ctgagcttca | 180 |
| tccccagcat | cattacaccg | tcaaaatgtt | ctctctcgcc | cgccttggta | ccgtcgctgg | 240 |
| tctcttcctt | ctcgctcagg | ctgccccgc | ttccctgcgc | cgtggtatgt | ttattttctc | 300 |
| cacaacttgt | aacacagcat | tcgcttgagc | cagactgacg | gatttagacg | tctcctcttc | 360 |
| ccttctcaac | aacctggacc | tcttcgctca | gtacagcgcc | gccgcttact | gcgatgagaa | 420 |
| cctgaactct | accggtacca | agttgacctg | ctctgttggc | aactgccctc | ttgtcgaggc | 480 |
| ggcctctacc | cagtccttgg | atgagttcaa | cgagtaagtc | accgcaaata | tacaattcta | 540 |
| gttcataagc | aactactgac | aactcagatc | gtcctcctac | ggcaaccccg | ccggttacct | 600 |
| cgccgctgac | gagactaaca | agctcctcgt | cctgtccttc | cgtggtagcg | ctgaccttgc | 660 |
| caactgggtc | gccaacctga | acttcggtct | cgaggacgcc | agcgatctgt | gctctggttg | 720 |
| cgaagtccac | tccggcttct | ggaaggcttg | gtctgagatc | gccgacacca | tcacttccaa | 780 |
| ggtggaatcc | gctttgtcgg | atcactccga | ttactccctc | gtcttgaccg | gtcactcgta | 840 |
| cggcgctgcg | ctggccgccc | tcgccgcgac | tgctctgcgt | aactccggcc | actcggttga | 900 |
| gctggtaagt | tatcctcatt | ttgtaagtga | cggtgcgcca | aatctgacca | aatagtacaa | 960 |
| ctacggtcag | cctcgccttg | gcaacgaggc | cctcgccacc | tacatcaccg | accagaacaa | 1020 |
| gggtggcaac | taccgcgtta | cccacactaa | cgacatcgtc | cctaagctgc | ccccacccct | 1080 |
| gctcggttac | caccacttca | gccccgagta | ctacatcagc | agcgccgacg | aggccaccgt | 1140 |
| gaccaccact | gacgtgactg | aggttaccgg | aatcgatgct | accggcggta | acgatggaac | 1200 |
| cgacggaact | agcatcgacg | ctcaccgttg | gtacttcatt | tacatttccg | aatgctccta | 1260 |
| aatac | | | | | 1265 |

<210> SEQ ID NO 13
<211> LENGTH: 1265
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Recombinant fusion construct, generated by PCR,
      of a promoter fragment and a gene fragment
<220> FEATURE:
<221> NAME/KEY: promoter
<222> LOCATION: (1)..(205)
<220> FEATURE:
<221> NAME/KEY: gene
<222> LOCATION: (206)..(1265)

<400> SEQUENCE: 13

| | | | | | |
|---|---|---|---|---|---|
| ggaattcaag | ctagatgcta | agcgatattg | catggcaata | tgtgttgatg | catgtgcttc | 60 |
| ttccttcagc | ttcccctcgt | gcagatgagg | tttggctata | aattgaagtg | gttggtcggg | 120 |
| gttccgtgag | gggctgaagt | gcttcctccc | ttttagacgc | aactgagagc | ctgagcttca | 180 |

-continued

```
tccccagcat cattacgcag tcaagatgtt ctctctcgcc cgccttggta ccgtcgctgg    240
tctcttcctt ctcgctcagg ctgccccgc ttccctgcgc cgtggtatgt ttattttctc     300
cacaacttgt aacacagcat tcgcttgagc cagactgacg gatttagacg tctcctcttc    360
ccttctcaac aacctggacc tcttcgctca gtacagcgcc gccgcttact gcgatgagaa    420
cctgaactct accggtacca agttgacctg ctctgttggc aactgccctc ttgtcgaggc    480
ggcctctacc cagtccttgg atgagttcaa cgagtaagtc accgcaaata tacaattcta    540
gttcataagc aactactgac aactcagatc gtcctcctac ggcaacccccg ccggttacct   600 cgccgctgac gagactaaca agctcctcgt cctgtccttc cgtggtagcg ctgaccttgc    660
caactgggtc gccaacctga acttcggtct cgaggacgcc agcgatctgt gctctggttg    720
cgaagtccac tccggcttct ggaaggcttg gtctgagatc gccgacacca tcacttccaa    780
ggtggaatcc gctttgtcgg atcactccga ttactccctc gtcttgaccg gtcactcgta    840
cggcgctgcg ctgccgcc tcgccgcgac tgctctgcgt aactccggcc actcggttga     900
gctggtaagt tatcctcatt ttgtaagtga cggtgcgcca aatctgacca aatagtacaa    960
ctacggtcag cctcgccttg gcaacgaggc cctcgccacc tacatcaccg accagaacaa   1020
gggtggcaac taccgcgtta cccacactaa cgacatcgtc cctaagctgc cccccaccct   1080
gctcggttac caccacttca gccccgagta ctacatcagc agcgccgacg aggccaccgt   1140
gaccaccact gacgtgactg aggttaccgg aatcgatgct accggcggta acgatggaac   1200
cgacggaact agcatcgacg ctcaccgttg gtacttcatt tacatttccg aatgctccta   1260
aatac                                                              1265
```

<210> SEQ ID NO 14
<211> LENGTH: 1265
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Recombinant fusion construct, generated by PCR,
      of a promoter fragment and a gene fragment
<220> FEATURE:
<221> NAME/KEY: promoter
<222> LOCATION: (1)..(205)
<220> FEATURE:
<221> NAME/KEY: gene
<222> LOCATION: (206)..(1265)

<400> SEQUENCE: 14

```
ggaattcaag ctagatgcta agcgatattg catggcaata tgtgttgatg catgtgcttc     60
ttccttcagc ttccctcgt gcagatgagg tttggctata aattgaagtg gttggtcggg    120
gttccgtgag gggctgaagt gcttcctccc ttttagacgc aactgagagc ctgagcttca    180
tccccagcat cattacaccg tcaaaatggc ttccttcgcc cgccttggta ccgtcgctgg    240
tctcttcctt ctcgctcagg ctgccccgc ttccctgcgc cgtggtatgt ttattttctc     300
cacaacttgt aacacagcat tcgcttgagc cagactgacg gatttagacg tctcctcttc    360
ccttctcaac aacctggacc tcttcgctca gtacagcgcc gccgcttact gcgatgagaa    420
cctgaactct accggtacca agttgacctg ctctgttggc aactgccctc ttgtcgaggc    480
ggcctctacc cagtccttgg atgagttcaa cgagtaagtc accgcaaata tacaattcta    540
gttcataagc aactactgac aactcagatc gtcctcctac ggcaacccccg ccggttacct   600 cgccgctgac gagactaaca agctcctcgt cctgtccttc cgtggtagcg ctgaccttgc    660
```

```
caactgggtc gccaacctga acttcggtct cgaggacgcc agcgatctgt gctctggttg    720
cgaagtccac tccggcttct ggaaggcttg gtctgagatc gccgacacca tcacttccaa    780
ggtggaatcc gctttgtcgg atcactccga ttactccctc gtcttgaccg gtcactcgta    840
cggcgctgcg ctggccgccc tcgccgcgac tgctctgcgt aactccggcc actcggttga    900
gctggtaagt tatcctcatt ttgtaagtga cggtgcgcca aatctgacca aatagtacaa    960
ctacggtcag cctcgccttg caacgaggc cctcgccacc tacatcaccg accagaacaa   1020
gggtggcaac taccgcgtta cccacactaa cgacatcgtc cctaagctgc cccccaccct   1080
gctcggttac caccacttca gccccgagta ctacatcagc agcgccgacg aggccaccgt   1140
gaccaccact gacgtgactg aggttaccgg aatcgatgct accggcggta acgatggaac   1200
cgacggaact agcatcgacg ctcaccgttg gtacttcatt tacatttccg aatgctccta   1260
aatac                                                              1265
```

```
<210> SEQ ID NO 15
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Phospholipase A1 from Aspergillus oryzae with
      modified signal sequence

<400> SEQUENCE: 15

Met Ala Ser Phe Ala Arg Leu Gly Thr Val Ala Gly Leu Phe Leu Leu
1               5                   10                  15

Ala Gln Ala Ala Pro Ala Ser Leu Arg Arg Asp Val Ser Ser Ser Leu
            20                  25                  30

Leu Asn Asn Leu Asp Leu Phe Ala Gln Tyr Ser Ala Ala Ala Tyr Cys
        35                  40                  45

Asp Glu Asn Leu Asn Ser Thr Gly Thr Lys Leu Thr Cys Ser Val Gly
    50                  55                  60

Asn Cys Pro Leu Val Glu Ala Ala Ser Thr Gln Ser Leu Asp Glu Phe
65                  70                  75                  80

Asn Glu Ser Ser Ser Tyr Gly Asn Pro Ala Gly Tyr Leu Ala Ala Asp
                85                  90                  95

Glu Thr Asn Lys Leu Leu Val Leu Ser Phe Arg Gly Ser Ala Asp Leu
            100                 105                 110

Ala Asn Trp Val Ala Asn Leu Asn Phe Gly Leu Glu Asp Ala Ser Asp
        115                 120                 125

Leu Cys Ser Gly Cys Glu Val His Ser Gly Phe Trp Lys Ala Trp Ser
    130                 135                 140

Glu Ile Ala Asp Thr Ile Thr Ser Lys Val Glu Ser Ala Leu Ser Asp
145                 150                 155                 160

His Ser Asp Tyr Ser Leu Val Leu Thr Gly His Ser Tyr Gly Ala Ala
                165                 170                 175

Leu Ala Ala Leu Ala Ala Thr Ala Leu Arg Asn Ser Gly His Ser Val
            180                 185                 190

Glu Leu Tyr Asn Tyr Gly Gln Pro Arg Leu Gly Asn Glu Ala Leu Ala
        195                 200                 205

Thr Tyr Ile Thr Asp Gln Asn Lys Gly Gly Asn Tyr Arg Val Thr His
    210                 215                 220
```

```
Thr Asn Asp Ile Val Pro Lys Leu Pro Pro Thr Leu Leu Gly Tyr His
225                 230                 235                 240

His Phe Ser Pro Glu Tyr Tyr Ile Ser Ser Ala Asp Glu Ala Thr Val
            245                 250                 255

Thr Thr Thr Asp Val Thr Glu Val Thr Gly Ile Asp Ala Thr Gly Gly
        260                 265                 270

Asn Asp Gly Thr Asp Gly Thr Ser Ile Asp Ala His Arg Trp Tyr Phe
    275                 280                 285

Ile Tyr Ile Ser Glu Cys Ser
    290                 295
```

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      consensus translational initiator oligonucleotide

<400> SEQUENCE: 16 mwchkycamv                                                          10

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      consensus translational initiator oligonucleotide

<400> SEQUENCE: 17 mwchkycaaa                                                          10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      consensus translational initiator oligonucleotide

<400> SEQUENCE: 18 mwchkycaca                                                          10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      consensus translational initiator oligonucleotide

<400> SEQUENCE: 19 mwchkycaag                                                          10

<210> SEQ ID NO 20
<211> LENGTH: 9
<212> TYPE: DNA
<213> ORGANISM: Artificial Sequence
<220> FEATURE:
<223> OTHER INFORMATION: Description of Artificial Sequence: Synthetic
      consensus translational initiator oligonucleotide
<220> FEATURE:
<221> NAME/KEY: modified_base
<222> LOCATION: (4)..(4)
<223> OTHER INFORMATION: a, c, t or g -continued

<400> SEQUENCE: 20 gctnccyyc                                                                 9

<210> SEQ ID NO 21
<211> LENGTH: 9
<212> TYPE: DNA
<213> ORGANISM: Artificial Sequence
<220> FEATURE:
<223> OTHER INFORMATION: Description of Artificial Sequence: Synthetic
      translational initiator coding oligonucleotide

<400> SEQUENCE: 21 gcttccttc                                                                 9

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Synthetic
      translational initiator oligonucleotide

<400> SEQUENCE: 22
caccgtcaaa                                                               10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      translational initiator oligonucleotide

<400> SEQUENCE: 23
cgcagtcaag                                                               10

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      translational initiator region oligonucleotide

<400> SEQUENCE: 24
caccgtcaaa atggcttcct tc                                                 22

<210> SEQ ID NO 25
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Fragment of promoter with modified
      translational initiator sequence
<220> FEATURE:
<221> NAME/KEY: misc_feature
<222> LOCATION: (195)..(204)
<223> OTHER INFORMATION: translational initiator sequence

<400> SEQUENCE: 25
gaattcaagc tagatgctaa gcgatattgc atggcaatat gtgttgatgc atgtgcttct        60
tccttcagct tcccctcgtg cagatgaggt ttggctataa attgaagtgg ttggtcgggg       120
ttccgtgagg ggctgaagtg cttcctccct tttagacgca actgagagcc tgagcttcat    180
ccccagcatc attacaccgt caaaatg                                        207

<210> SEQ ID NO 26
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Fragment of promoter with modified
      translational initiator sequence
<220> FEATURE:
<221> NAME/KEY: misc_feature
<222> LOCATION: (195)..(204)
<223> OTHER INFORMATION: translational initiator sequence

<400> SEQUENCE: 26
gaattcaagc tagatgctaa gcgatattgc atggcaatat gtgttgatgc atgtgcttct     60
tccttcagct tcccctcgtg cagatgaggt ttggctataa attgaagtgg ttggtcgggg    120
ttccgtgagg ggctgaagtg cttcctccct tttagacgca actgagagcc tgagcttcat    180
ccccagcatc attacgcagt caagatg                                        207

<210> SEQ ID NO 27
<211> LENGTH: 216
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Fragment of promoter with modified
      translational initiator region sequence
<220> FEATURE:
<221> NAME/KEY: misc_feature
<222> LOCATION: (195)..(216)
<223> OTHER INFORMATION: translational initiator region sequence

<400> SEQUENCE: 27
gaattcaagc tagatgctaa gcgatattgc atggcaatat gtgttgatgc atgtgcttct     60
tccttcagct tcccctcgtg cagatgaggt ttggctataa attgaagtgg ttggtcgggg    120
ttccgtgagg ggctgaagtg cttcctccct tttagacgca actgagagcc tgagcttcat    180
ccccagcatc attacaccgt caaaatggct tccttc                              216

<210> SEQ ID NO 28
<211> LENGTH: 3965
<212> TYPE: DNA
<213> ORGANISM: Aspergillus niger

<400> SEQUENCE: 28
gtttgacgcg tttgcagtgt agaagcttcc agctaccgta gattactgat acaaactcaa     60
tacactattt ctataacctt actgttcaat acagtacgat caaaatttcc ggaatattaa    120
tgttacggtt accttccata tgtagactag cgcacttggc attagggttc gaaatacgat    180
caaagagtat tgggggggggt gacagcagta atgactccaa ctgtaaatcg gcttctaggc    240
gcgctccatc taaatgttct ggctgtggt  tacaggggca taaattacg cactacccga    300 atcgatagaa ctactcattt ttatatagaa gtcagaattc atggtgtttt gatcatttta    360 aattttata tggcgggtgg tggcaactc gcttgcgcgg gcaactcgct taccgattac    420
gttagggctg atatttacgt aaaaatcgtc aagggatgca agaccaaagt actaaaaccc    480

```
cggagtcaac agcatccaag cccaagtcct tcacggagaa accccagcgt ccacatcacg    540
agcgaaggac cacctctagg catcggacgc accatccaat tagaagcagc aaagcgaaac    600
agcccaagaa aaaggtcggc ccgtcggcct tttctgcaac gctgatcacg ggcagcgatc    660
caaccaacac cctccagagt gactaggggc ggaaatttat cgggattaat ttccactcaa    720
ccacaaatca cagtcgtccc cggtattgtc ctgcagaatg caatttaaac tcttctgcga    780
atcgcttgga ttccccgccc ctggccgtag agcttaaagt atgtcccttg tcgatgcgat    840
gtatcacaac atataaatac tagcaaggga tgccatgctt ggaggatagc aaccgacaac    900
atcacatcaa gctctccctt ctctgaacaa taaaccccac agaaggcatt tatgatggtc    960
gcgtggtggt ctctatttct gtacggcctt caggtcgcgg cacctgcttt ggctgcaacg   1020
cctgcggact ggcgatcgca atccatttat ttccttctca cggatcgatt tgcaaggacg   1080
gatgggtcga cgactgcgac ttgtaatact gcggatcagg tgtgttgtta cctactagct   1140
ttcagaaaga ggaatgtaaa ctgacttgat atagaaatac tgtggtggaa catggcaggg   1200
catcatcgac aaggtaaatt gccccttttat caaaaaaaaa agaaggaaaa gcagaagaaa   1260
aataaaataa aaagaactct agtcctaacc atcacatagt tggactatat ccagggaatg   1320
ggcttcacag ccatctggat cacccccgtt acagcccagc tgcccagac caccgcatat    1380 ggagatgcct accatggcta ctggcagcag gatatgtaag tcgatttctt taaatatcta   1440
cctgtcatct tttacatcaa tatgaactaa cttgatggtt ttagatactc tctgaacgaa   1500
aactacggca ctgcagatga cttgaaggcg ctctcttcgg cccttcatga gaggggatg     1560 tatcttatgg tcgatgtggt tgctaaccat atggttcgtg gtccttttgca actgacttcg   1620 cggatatggt tcatttcagt actgacaatg agtaatatca gggctatgat ggagcgggta   1680
gctcagtcga ttacagtgtg tttaaaccgt tcagttccca agactacttc cacccgttct   1740
gtttcattca aaactatgaa gatcagactc aggttgagga ttgctggcta ggagataaca   1800
ctgtctcctt gcctgatctc gataccacca aggatgtggt caagaatgaa tggtacgact   1860
gggtgggatc attggtatcg aactactcca gtaagatatt tctccctcat tctacaactt   1920
ggctgatcga tgatacttac gaaatcagtt gacggcctcc gtatcgacac agtaaaacac   1980
gtccagaagg acttctggcc cgggtacaac aaagccgcag gcgtgtactg tatcggcgag   2040
gtgctcgacg gtgatccggc ctacacttgt ccctaccaga acgtcatgga cggcgtactg   2100
aactatccca tgtatggttc ctccaaccat gagccttctt gcaagtctca tctcctaacg   2160
aaacggctaa aaccagttac tatccactcc tcaacgcctt caagtcaacc tccggcagca   2220
tggacgacct ctacaacatg atcaacaccg tcaaatccga ctgtccagac tcaacactcc   2280
tgggcacatt cgtcgagaac cacgacaacc cacggttcgc ttcgtaagtc ttcccttta    2340 ttttccgttc ccaatttcca cacagaaccc cacctaacaa gagcaaagtt acaccaacga   2400
catagccctc gccaagaacg tcgcagcatt catcatcctc aacgacggaa tccccatcat   2460
ctacgccggc caagaacagc actacgccgg cggaaacgac cccgcgaacc gcgaagcaac   2520
ctggctctcg ggctacccga ccgacagcga gctgtacaag ttaattgcct ccgcgaacgc   2580
aatccggaac tatgccatta gcaaagatac aggattcgtg acctacaagg taagcacaac   2640
ctctaagcat accctaatgg cctatcttca gagtatctga cacaagagac taatcactgg   2700
caatacagaa ctggcccatc tacaaagacg acacaacgat cgccatgcgc aagggcacag   2760
atgggtcgca gatcgtgact atcttgtcca acaagggtgc ttcgggtgat tcgtataccc   2820
```

-continued

```
tctccttgag tggtgcgggt tacacagccg ccagcaatt gacggaggtc attggctgca      2880
cgaccgtgac ggttggttcg gatggaaatg tgcctgttcc tatggcaggt gggctaccta      2940
gggtattgta tccgactgag aagttggcag gtagcaagat ctgtagtagc tcgtgaaggg      3000
tggagagtat atgatggtac tgctattcaa tctggcattg gacagtgagt ttgagtttga      3060
tgtacataac caaggttgtg tctgtataat atatacatgt aagatacatg agcttcggtg      3120
atataataca gaagtaccat acagtaccgc gttatgaaaa cacattaatc cggatccttt      3180
cctataatag actagcgtgc ttggcattag ggttcgaaaa acaatcgaag agtataaggg      3240
gatgacagca gtaacgactc caactgtagc ccacatcttg agttcggcaa ctactgttgg      3300
cacgtgaccc tgtgccttgt ggtagctcct taactttgtc atcattcgaa gaattttcgt      3360
cccttcccag gtaccatcca aaagacaagc atccgtcgct tcactctgag atcagatgag      3420
agtaatattg ttgactgcgt ttgtgatgcg ggtgatgtcc tctgcgatcg gccgcaagct      3480
gtttagtttg ccccggatct tctgtgccga cggttgctcc ccgaattttc ttagctagtg      3540
taatcacgct attcagaaag gcttccaaga attaggccgg tagttcggcg cgtttggtgt      3600
cgtcaagctc cagcagtgct ggggcctcgg ctatgatatg gttagaatgc tcggggtggg      3660
tcacggcagg acacccgaca ctgcaacgtc taccacattt gagcgttatt ggcagacttg      3720
cggcgagata acgaccgcta gcttgtatca accaaatcca actgaaatta ttgctttgcc      3780
atcccaacag tggatttcgg aggagggagg ggggaagata tacgatgaac ggaagactgg      3840
acaagatacg ttcataaaag cagtactact tgtttcaaac tgtgtacaca ccagggctct      3900
cgcttcagcg gagagtgtcg aaagattcag taaaacatcg ccagggtgga tggaaagggg      3960
ttaag                                                                   3965
```

<210> SEQ ID NO 29
<211> LENGTH: 1497
<212> TYPE: DNA
<213> ORGANISM: Aspergillus niger
<220> FEATURE:
<221> NAME/KEY: CDS
<222> LOCATION: (1)..(1497)

<400> SEQUENCE: 29

```
atg gtc gcg tgg tgg tct cta ttt ctg tac ggc ctt cag gtc gcg gca       48
Met Val Ala Trp Trp Ser Leu Phe Leu Tyr Gly Leu Gln Val Ala Ala
1               5                   10                  15 cct gct ttg gct gca acg cct gcg gac tgg cga tcg caa tcc att tat       96
Pro Ala Leu Ala Ala Thr Pro Ala Asp Trp Arg Ser Gln Ser Ile Tyr
            20                  25                  30 ttc ctt ctc acg gat cga ttt gca agg acg gat ggg tcg acg act gcg      144
Phe Leu Leu Thr Asp Arg Phe Ala Arg Thr Asp Gly Ser Thr Thr Ala
        35                  40                  45 act tgt aat act gcg gat cag aaa tac tgt ggt gga aca tgg cag ggc      192
Thr Cys Asn Thr Ala Asp Gln Lys Tyr Cys Gly Gly Thr Trp Gln Gly
    50                  55                  60 atc atc gac aag ttg gac tat atc cag gga atg ggc ttc aca gcc atc      240
Ile Ile Asp Lys Leu Asp Tyr Ile Gln Gly Met Gly Phe Thr Ala Ile
65                  70                  75                  80 tgg atc acc ccc gtt aca gcc cag ctg ccc cag acc acc gca tat gga      288
Trp Ile Thr Pro Val Thr Ala Gln Leu Pro Gln Thr Thr Ala Tyr Gly
                85                  90                  95 gat gcc tac cat ggc tac tgg cag cag gat ata tac tct ctg aac gaa      336
Asp Ala Tyr His Gly Tyr Trp Gln Gln Asp Ile Tyr Ser Leu Asn Glu
            100                 105                 110
```

|   |   |   |   |   |   |   |   |   |   |   |   |   |   |   |   |   |
|---|---|---|---|---|---|---|---|---|---|---|---|---|---|---|---|---|
| aac | tac | ggc | act | gca | gat | gac | ttg | aag | gcg | ctc | tct | tcg | gcc | ctt | cat | 384 |
| Asn | Tyr | Gly | Thr | Ala | Asp | Asp | Leu | Lys | Ala | Leu | Ser | Ser | Ala | Leu | His | |
|   |   | 115 |   |   |   | 120 |   |   |   | 125 |   |   |   |   |   |   |

| gag | agg | ggg | atg | tat | ctt | atg | gtc | gat | gtg | gtt | gct | aac | cat | atg | ggc | 432 |
|---|---|---|---|---|---|---|---|---|---|---|---|---|---|---|---|---|
| Glu | Arg | Gly | Met | Tyr | Leu | Met | Val | Asp | Val | Val | Ala | Asn | His | Met | Gly | |
|   | 130 |   |   |   |   | 135 |   |   |   |   | 140 |   |   |   |   |   |

| tat | gat | gga | gcg | ggt | agc | tca | gtc | gat | tac | agt | gtg | ttt | aaa | ccg | ttc | 480 |
|---|---|---|---|---|---|---|---|---|---|---|---|---|---|---|---|---|
| Tyr | Asp | Gly | Ala | Gly | Ser | Ser | Val | Asp | Tyr | Ser | Val | Phe | Lys | Pro | Phe | |
| 145 |   |   |   |   | 150 |   |   |   |   | 155 |   |   |   |   | 160 |   |

| agt | tcc | caa | gac | tac | ttc | cac | ccg | ttc | tgt | ttc | att | caa | aac | tat | gaa | 528 |
|---|---|---|---|---|---|---|---|---|---|---|---|---|---|---|---|---|
| Ser | Ser | Gln | Asp | Tyr | Phe | His | Pro | Phe | Cys | Phe | Ile | Gln | Asn | Tyr | Glu | |
|   |   |   |   | 165 |   |   |   |   | 170 |   |   |   |   | 175 |   |   |

| gat | cag | act | cag | gtt | gag | gat | tgc | tgg | cta | gga | gat | aac | act | gtc | tcc | 576 |
|---|---|---|---|---|---|---|---|---|---|---|---|---|---|---|---|---|
| Asp | Gln | Thr | Gln | Val | Glu | Asp | Cys | Trp | Leu | Gly | Asp | Asn | Thr | Val | Ser | |
|   |   | 180 |   |   |   |   | 185 |   |   |   |   | 190 |   |   |   |   |

| ttg | cct | gat | ctc | gat | acc | acc | aag | gat | gtg | gtc | aag | aat | gaa | tgg | tac | 624 |
|---|---|---|---|---|---|---|---|---|---|---|---|---|---|---|---|---|
| Leu | Pro | Asp | Leu | Asp | Thr | Thr | Lys | Asp | Val | Val | Lys | Asn | Glu | Trp | Tyr | |
|   | 195 |   |   |   |   | 200 |   |   |   |   | 205 |   |   |   |   |   |

| gac | tgg | gtg | gga | tca | ttg | gta | tcg | aac | tac | tcc | att | gac | ggc | ctc | cgt | 672 |
|---|---|---|---|---|---|---|---|---|---|---|---|---|---|---|---|---|
| Asp | Trp | Val | Gly | Ser | Leu | Val | Ser | Asn | Tyr | Ser | Ile | Asp | Gly | Leu | Arg | |
| 210 |   |   |   |   | 215 |   |   |   |   | 220 |   |   |   |   |   |   |

| atc | gac | aca | gta | aaa | cac | gtc | cag | aag | gac | ttc | tgg | ccc | ggg | tac | aac | 720 |
|---|---|---|---|---|---|---|---|---|---|---|---|---|---|---|---|---|
| Ile | Asp | Thr | Val | Lys | His | Val | Gln | Lys | Asp | Phe | Trp | Pro | Gly | Tyr | Asn | |
| 225 |   |   |   |   | 230 |   |   |   |   | 235 |   |   |   |   | 240 |   |

| aaa | gcc | gca | ggc | gtg | tac | tgt | atc | ggc | gag | gtg | ctc | gac | ggt | gat | ccg | 768 |
|---|---|---|---|---|---|---|---|---|---|---|---|---|---|---|---|---|
| Lys | Ala | Ala | Gly | Val | Tyr | Cys | Ile | Gly | Glu | Val | Leu | Asp | Gly | Asp | Pro | |
|   |   |   |   | 245 |   |   |   |   | 250 |   |   |   |   | 255 |   |   |

| gcc | tac | act | tgt | ccc | tac | cag | aac | gtc | atg | gac | ggc | gta | ctg | aac | tat | 816 |
|---|---|---|---|---|---|---|---|---|---|---|---|---|---|---|---|---|
| Ala | Tyr | Thr | Cys | Pro | Tyr | Gln | Asn | Val | Met | Asp | Gly | Val | Leu | Asn | Tyr | |
|   |   | 260 |   |   |   |   | 265 |   |   |   |   | 270 |   |   |   |   |

| ccc | att | tac | tat | cca | ctc | ctc | aac | gcc | ttc | aag | tca | acc | tcc | ggc | agc | 864 |
|---|---|---|---|---|---|---|---|---|---|---|---|---|---|---|---|---|
| Pro | Ile | Tyr | Tyr | Pro | Leu | Leu | Asn | Ala | Phe | Lys | Ser | Thr | Ser | Gly | Ser | |
|   | 275 |   |   |   |   | 280 |   |   |   |   | 285 |   |   |   |   |   |

| atg | gac | gac | ctc | tac | aac | atg | atc | aac | acc | gtc | aaa | tcc | gac | tgt | cca | 912 |
|---|---|---|---|---|---|---|---|---|---|---|---|---|---|---|---|---|
| Met | Asp | Asp | Leu | Tyr | Asn | Met | Ile | Asn | Thr | Val | Lys | Ser | Asp | Cys | Pro | |
| 290 |   |   |   |   | 295 |   |   |   |   | 300 |   |   |   |   |   |   |

| gac | tca | aca | ctc | ctg | ggc | aca | ttc | gtc | gag | aac | cac | gac | aac | cca | cgg | 960 |
|---|---|---|---|---|---|---|---|---|---|---|---|---|---|---|---|---|
| Asp | Ser | Thr | Leu | Leu | Gly | Thr | Phe | Val | Glu | Asn | His | Asp | Asn | Pro | Arg | |
| 305 |   |   |   |   | 310 |   |   |   |   | 315 |   |   |   |   | 320 |   |

| ttc | gct | tct | tac | acc | aac | gac | ata | gcc | ctc | gcc | aag | aac | gtc | gca | gca | 1008 |
|---|---|---|---|---|---|---|---|---|---|---|---|---|---|---|---|---|
| Phe | Ala | Ser | Tyr | Thr | Asn | Asp | Ile | Ala | Leu | Ala | Lys | Asn | Val | Ala | Ala | |
|   |   |   |   | 325 |   |   |   |   | 330 |   |   |   |   | 335 |   |   |

| ttc | atc | atc | ctc | aac | gac | gga | atc | ccc | atc | atc | tac | gcc | ggc | caa | gaa | 1056 |
|---|---|---|---|---|---|---|---|---|---|---|---|---|---|---|---|---|
| Phe | Ile | Ile | Leu | Asn | Asp | Gly | Ile | Pro | Ile | Ile | Tyr | Ala | Gly | Gln | Glu | |
|   |   |   | 340 |   |   |   |   | 345 |   |   |   |   | 350 |   |   |   |

| cag | cac | tac | gcc | ggc | gga | aac | gac | ccc | gcg | aac | cgc | gaa | gca | acc | tgg | 1104 |
|---|---|---|---|---|---|---|---|---|---|---|---|---|---|---|---|---|
| Gln | His | Tyr | Ala | Gly | Gly | Asn | Asp | Pro | Ala | Asn | Arg | Glu | Ala | Thr | Trp | |
|   |   | 355 |   |   |   |   | 360 |   |   |   |   | 365 |   |   |   |   |

| ctc | tcg | ggc | tac | ccg | acc | gac | agc | gag | ctg | tac | aag | tta | att | gcc | tcc | 1152 |
|---|---|---|---|---|---|---|---|---|---|---|---|---|---|---|---|---|
| Leu | Ser | Gly | Tyr | Pro | Thr | Asp | Ser | Glu | Leu | Tyr | Lys | Leu | Ile | Ala | Ser | |
| 370 |   |   |   |   | 375 |   |   |   |   | 380 |   |   |   |   |   |   |

| gcg | aac | gca | atc | cgg | aac | tat | gcc | att | agc | aaa | gat | aca | gga | ttc | gtg | 1200 |
|---|---|---|---|---|---|---|---|---|---|---|---|---|---|---|---|---|
| Ala | Asn | Ala | Ile | Arg | Asn | Tyr | Ala | Ile | Ser | Lys | Asp | Thr | Gly | Phe | Val | |
| 385 |   |   |   |   | 390 |   |   |   |   | 395 |   |   |   |   | 400 |   |

| acc | tac | aag | aac | tgg | ccc | atc | tac | aaa | gac | gac | aca | acg | atc | gcc | atg | 1248 |
|---|---|---|---|---|---|---|---|---|---|---|---|---|---|---|---|---|
| Thr | Tyr | Lys | Asn | Trp | Pro | Ile | Tyr | Lys | Asp | Asp | Thr | Thr | Ile | Ala | Met | |
|   |   |   | 405 |   |   |   |   | 410 |   |   |   |   | 415 |   |   |   |

| cgc | aag | ggc | aca | gat | ggg | tcg | cag | atc | gtg | act | atc | ttg | tcc | aac | aag | 1296 |
|---|---|---|---|---|---|---|---|---|---|---|---|---|---|---|---|---|
| Arg | Lys | Gly | Thr | Asp | Gly | Ser | Gln | Ile | Val | Thr | Ile | Leu | Ser | Asn | Lys | |
|   | 420 |   |   |   |   | 425 |   |   |   |   | 430 |   |   |   |   |   |

```
ggt gct tcg ggt gat tcg tat acc ctc tcc ttg agt ggt gcg ggt tac    1344
Gly Ala Ser Gly Asp Ser Tyr Thr Leu Ser Leu Ser Gly Ala Gly Tyr
        435                 440                 445 aca gcc ggc cag caa ttg acg gag gtc att ggc tgc acg acc gtg acg    1392
Thr Ala Gly Gln Gln Leu Thr Glu Val Ile Gly Cys Thr Thr Val Thr
    450                 455                 460 gtt ggt tcg gat gga aat gtg cct gtt cct atg gca ggt ggg cta cct    1440
Val Gly Ser Asp Gly Asn Val Pro Val Pro Met Ala Gly Gly Leu Pro
465                 470                 475                 480 agg gta ttg tat ccg act gag aag ttg gca ggt agc aag atc tgt agt    1488
Arg Val Leu Tyr Pro Thr Glu Lys Leu Ala Gly Ser Lys Ile Cys Ser
                485                 490                 495 agc tcg tga                                                        1497
Ser Ser

<210> SEQ ID NO 30
<211> LENGTH: 498
<212> TYPE: PRT
<213> ORGANISM: Aspergillus niger

<400> SEQUENCE: 30

Met Val Ala Trp Trp Ser Leu Phe Leu Tyr Gly Leu Gln Val Ala Ala
1               5                   10                  15

Pro Ala Leu Ala Ala Thr Pro Ala Asp Trp Arg Ser Gln Ser Ile Tyr
            20                  25                  30

Phe Leu Leu Thr Asp Arg Phe Ala Arg Thr Asp Gly Ser Thr Thr Ala
        35                  40                  45

Thr Cys Asn Thr Ala Asp Gln Lys Tyr Cys Gly Gly Thr Trp Gln Gly
    50                  55                  60

Ile Ile Asp Lys Leu Asp Tyr Ile Gln Gly Met Gly Phe Thr Ala Ile
65                  70                  75                  80

Trp Ile Thr Pro Val Thr Ala Gln Leu Pro Gln Thr Thr Ala Tyr Gly
                85                  90                  95

Asp Ala Tyr His Gly Tyr Trp Gln Gln Asp Ile Tyr Ser Leu Asn Glu
            100                 105                 110

Asn Tyr Gly Thr Ala Asp Asp Leu Lys Ala Leu Ser Ser Ala Leu His
        115                 120                 125

Glu Arg Gly Met Tyr Leu Met Val Asp Val Val Ala Asn His Met Gly
    130                 135                 140

Tyr Asp Gly Ala Gly Ser Ser Val Asp Tyr Ser Val Phe Lys Pro Phe
145                 150                 155                 160

Ser Ser Gln Asp Tyr Phe His Pro Phe Cys Phe Ile Gln Asn Tyr Glu
                165                 170                 175

Asp Gln Thr Gln Val Glu Asp Cys Trp Leu Gly Asp Asn Thr Val Ser
            180                 185                 190

Leu Pro Asp Leu Asp Thr Thr Lys Asp Val Val Lys Asn Glu Trp Tyr
        195                 200                 205

Asp Trp Val Gly Ser Leu Val Ser Asn Tyr Ser Ile Asp Gly Leu Arg
    210                 215                 220

Ile Asp Thr Val Lys His Val Gln Lys Asp Phe Trp Pro Gly Tyr Asn
225                 230                 235                 240

Lys Ala Ala Gly Val Tyr Cys Ile Gly Glu Val Leu Asp Gly Asp Pro
                245                 250                 255

Ala Tyr Thr Cys Pro Tyr Gln Asn Val Met Asp Gly Val Leu Asn Tyr
            260                 265                 270
```

```
Pro Ile Tyr Tyr Pro Leu Leu Asn Ala Phe Lys Ser Thr Ser Gly Ser
            275                 280                 285

Met Asp Asp Leu Tyr Asn Met Ile Asn Thr Val Lys Ser Asp Cys Pro
            290                 295                 300

Asp Ser Thr Leu Leu Gly Thr Phe Val Glu Asn His Asp Asn Pro Arg
305                 310                 315                 320

Phe Ala Ser Tyr Thr Asn Asp Ile Ala Leu Ala Lys Asn Val Ala Ala
                325                 330                 335

Phe Ile Ile Leu Asn Asp Gly Ile Pro Ile Ile Tyr Ala Gly Gln Glu
            340                 345                 350

Gln His Tyr Ala Gly Gly Asn Asp Pro Ala Asn Arg Glu Ala Thr Trp
            355                 360                 365

Leu Ser Gly Tyr Pro Thr Asp Ser Glu Leu Tyr Lys Leu Ile Ala Ser
            370                 375                 380

Ala Asn Ala Ile Arg Asn Tyr Ala Ile Ser Lys Asp Thr Gly Phe Val
385                 390                 395                 400

Thr Tyr Lys Asn Trp Pro Ile Tyr Lys Asp Asp Thr Thr Ile Ala Met
                405                 410                 415

Arg Lys Gly Thr Asp Gly Ser Gln Ile Val Thr Ile Leu Ser Asn Lys
            420                 425                 430

Gly Ala Ser Gly Asp Ser Tyr Thr Leu Ser Leu Ser Gly Ala Gly Tyr
            435                 440                 445

Thr Ala Gly Gln Gln Leu Thr Glu Val Ile Gly Cys Thr Thr Val Thr
            450                 455                 460

Val Gly Ser Asp Gly Asn Val Pro Val Pro Met Ala Gly Gly Leu Pro
465                 470                 475                 480

Arg Val Leu Tyr Pro Thr Glu Lys Leu Ala Gly Ser Lys Ile Cys Ser
                485                 490                 495

Ser Ser

<210> SEQ ID NO 31
<211> LENGTH: 3494
<212> TYPE: DNA
<213> ORGANISM: Aspergillus niger

<400> SEQUENCE: 31
ctcgagggac aacgcatcgt ttgatacact tcccgccaat atggacgttg tccagaagcc      60
tgttcagcat cgatctgggc gtctcgttct gtaagcattc tcctagttac tgatgacttt     120
cctctcttat ctgtattccg tgaaagagga gggccactgt cctctatata gtttatggat     180
ataaaaagtt tgagcttctt gccaatatga aacagatttc cccacattaa gagctgtttc     240
tctataggtt tccaatcaat attagtgccg tcaaaacgtt tgttcagatc agattgtcca     300
cgttcgttta cagatactct gactgtagta tcatctgatc tcacacgttg gttgtgacgt     360 attttttcgac gcataacatt ttcagcatcc tgtgttatct tcgcccagtg tgaactgggt     420
gctacagcca agtcctgttc agtgtccttt gacacagttc ggttgttcag agttaccttc     480
cactcaatag tataatgaat acaaggcttt cctctatgtt gcctcgtagt ccttctcttcg     540 ggctcctgga agaaacccag atgattgggc tgggattgat gcaagggagt ataaggttca     600
tcaagtacat gttcaggtga tgggcaaaat acgatggcg tacgatctct accgaagtca      660
ccaggggtgg gggcatacga tggagtttgt atccacggat caggtggctg aagctgagag     720
gcatcgtcat cgtagtaagg actaaacgtc atccccctcaa ggcagtagat gccactgaga     780
agcctagtgt tgggatcatc atatgttagc ctacaccata tgggtgtccc agcaagagtg     840
```

-continued

```
tccgtgaggg aagaggtgca gctaacaaaa ccagtaaaat gatcaggttc atggacaatg    900
aactaagaca ggtacagtat tgtagcccta cccgtcttgg ttaacctggt aaggtcaaaa    960
aggatcgaac cgtggctcag tacaaacaaa aggaatgtta acagtttgcg ggagatgcaa   1020
ggcacatgct ttgtcatgtt tgacgcgttt gcagtgtaga agcttccagc taccgtagat   1080
tactgataca aactcaatac actatttcta taaccttact gttcaataca gtacgatcaa   1140
aatttccgga atattaatgt tacggttacc ttccatatgt agactagcgc acttggcatt   1200
agggttcgaa atacgatcaa agagtattgg gggggtgac agcagtaatg actccaactg    1260
taaatcggct tctaggcgcg ctccatctaa atgttctggc tgtggtgtac aggggcataa   1320
aattacgcac tacccgaatc gatagaacta ctcattttta tatagaagtc agaattcatg   1380
gtgttttgat cattttaaat ttttatatgg cgggtggtgg gcaactcgct tgcgcgggca   1440
actcgcttac cgattacgtt agggctgata tttacgtaaa aatcgtcaag ggatgcaaga   1500
ccaaagtact aaaaccccgg agtcaacagc atccaagccc aagtccttca cggagaaacc   1560
ccagcgtcca catcacgagc gaaggaccac ctctaggcat cggacgcacc atccaattag   1620
aagcagcaaa gcgaaacagc ccaagaaaaa ggtcggcccg tcggcttttt ctgcaacgct   1680
gatcacgggc agcgatccaa ccaacaccct ccagagtgac taggggcgga aatttatcgg   1740
gattaatttc cactcaacca caaatcacag tcgtccccgg tattgtcctg cagaatgcaa   1800
tttaaactct tctgcgaatc gcttggattc cccgcccctg ccgtagagc ttaaagtatg    1860
tcccttgtcg atgcgatgta tcacaacata taaatactag caagggatgc catgcttgga   1920
ggatagcaac cgacaacatc acatcaagct ctcccttctc tgaacaataa accccacaga   1980
aggcatttat ggtcgcgtgg tggtctctat ttctgtacgg ccttcaggtc gcggcacctg   2040
ctttggctgc aacgcctgcg gactggcgat cgcaatccat ttatttcctt ctcacggatc   2100
gatttgcaag gacggatggg tcgacgactg cgacttgtaa tactgcggat cagaaatact   2160
gtggtggaac atggcagggc atcatcgaca agttggacta tatccaggga atgggcttca   2220
cagccatctg gatcaccccc gttacagccc agctgcccca gaccaccgca tatggagatg   2280
cctaccatgg ctactggcag caggatatat actctctgaa cgaaaactac ggcactgcag   2340
atgacttgaa ggcgctctct tcggcccttc atgagagggg gatgtatctt atggtcgatg   2400
tggttgctaa ccatatgggc tatgatggag cgggtagctc agtcgattac agtgtgttta   2460
aaccgttcag ttcccaagac tacttccacc cgttctgttt cattcaaaac tatgaagatc   2520
agactcaggt tgaggattgc tggctaggag ataacactgt ctccttgcct gatctcgata   2580
ccaccaagga tgtggtcaag aatgaatggt acgactgggt gggatcattg gtatcgaact   2640
actccattga cggcctccgt atcgacacag taaaacacgt ccagaaggac ttctggcccg   2700
ggtacaacaa agccgcaggc gtgtactgta tcggcgaggt gctcgacggt gatccggcct   2760
acacttgtcc ctaccagaac gtcatggacg gcgtactgaa ctatcccatt tactatccac   2820
tcctcaacgc cttcaagtca acctccggca gcatggacga cctctacaac atgatcaaca   2880
ccgtcaaatc cgactgtcca gactcaacac tcctgggcac attcgtcgag aaccacgaca   2940
acccacggtt cgcttcttac accaacgaca tagcccctcgc caagaacgtc gcagcattca   3000
tcatcctcaa cgacggaatc cccatcatct acgccggcca agaacagcac tacgccggcg   3060
gaaacgaccc cgcgaaccgc gaagcaacct ggctctcggg ctaccgacc acagcgagc    3120
tgtacaagtt aattgcctcc gcgaacgcaa tccggaacta tgccattagc aaagatacag   3180
```

-continued

```
gattcgtgac ctacaagaac tggcccatct acaaagacga cacaacgatc gccatgcgca    3240
agggcacaga tgggtcgcag atcgtgacta tcttgtccaa caagggtgct tcgggtgatt    3300
cgtataccct ctccttgagt ggtgcgggtt acacagccgg ccagcaattg acggaggtca    3360
ttggctgcac gaccgtgacg gttggttcgg atggaaatgt gcctgttcct atggcaggtg    3420
ggctacctag ggtattgtat ccgactgaga agttggcagg tagcaagatc tgtagtagct    3480
cgtaaattaa ttaa                                                     3494
```

<210> SEQ ID NO 32
<211> LENGTH: 1498
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide coding sequence of alpha amylase of
      Aspergillus niger with optimized coding frequency
<220> FEATURE:
<221> NAME/KEY: gene
<222> LOCATION: (1)..(494)
<220> FEATURE:
<221> NAME/KEY: misc_feature
<222> LOCATION: (1495)..(1498)
<223> OTHER INFORMATION: translational terminator sequence

<400> SEQUENCE: 32

```
atggtcgcct ggtggtccct gttcctctac ggacttcagg tggctgcccc cgctctcgcc      60 gcgaccccg ccgattggcg tagccagtcg atttacttct tgcttactga ccgcttcgct     120
cgcaccgacg gttccaccac cgccacctgc aacactgcgg accagaagta ctgcggcggc     180
acttggcagg gtatcatcga caagctggat tacatccagg gtatgggatt caccgctatc     240
tggattactc ctgttaccgc tcagctcccc cagaccaccg cctacggcga tgcctaccac     300
ggttactgga gcaggacat ctactctctg aacgaaaact acgtaccgc tgacgatctc      360 aaggccttgt cttccgccct ccacgagcgt ggcatgtacc tgatggtcga cgtcgtggct     420
aaccacatgg gttacgacgg tgcgggcagc tctgtcgatt actcggtttt caagcctttc     480
tcctcccagg attacttcca ccccttctgc ttcatccaga actacgagga ccagacccag     540
gtcgaggact gctggctggg agacaacact gtttcgcttc ccgatctcga cactaccaag     600
gacgtcgtta agaacgagtg gtacgattgg gtgggtagct tggtctccaa ctacagcatt     660
gacggcctcc gcatcgacac cgtcaagcac gtccagaagg atttctggcc tggatacaac     720
aaggccgccg gtgtgtactg catcggcgaa gttctggacg gtgaccctgc ttacacctgc     780
ccctaccaga acgtcatgga tggtgtcctg aactacccca tctactaccc ccttctcaac     840
gctttcaagt ctacctccgg ctccatggac gacctctaca catgattaa cactgttaag     900 agcgattgcc ctgactcgac cctgttgggc accttcgtgg agaaccacga taaccccgt     960 ttcgcctcct acactaacga catcgccctt gcgaagaacg tcgctgcctt catcatcctc    1020
aacgacggta ttcctatcat ctacgctggt caggagcagc actacgccgg cggaaacgat    1080
cccgctaacc gcgaagccac ctggctgtcc ggttacccca ccgactctga gctctacaag    1140
ctgatcgcta cgccaacgc gattcgtaac tacgccatct ccaaggacac tggcttcgtc    1200
acctacaaga actggcctat ctacaaggat gacaccacta tcgctatgcg taagggtacc    1260
gacggttctc agatcgttac catttttgtcc aacaagggag ccagcggtga ttcctacacc    1320
ctctctctgt ccggcgctgg ctacactgcc ggtcagcagc ttaccgaggt catcggatgc    1380
```

<210> SEQ ID NO 33
<211> LENGTH: 3494
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleotide sequence with the Aspergillus niger alpha amylase promoter with modified translational initiator sequence and the alpha amylase nucleotide coding sequence with modified translational terminator sequence
<220> FEATURE:
<221> NAME/KEY: promoter
<222> LOCATION: (1)..(1988)
<223> OTHER INFORMATION: alpha amylase promoter of Aspergillus niger
<220> FEATURE:
<221> NAME/KEY: misc_feature
<222> LOCATION: (1979)..(1988)
<223> OTHER INFORMATION: translational initiator sequence
<220> FEATURE:
<221> NAME/KEY: gene
<222> LOCATION: (1989)..(3494)

<400> SEQUENCE: 33

```
ctcgagggac aacgcatcgt ttgatacact tcccgccaat atggacgttg tccagaagcc     60
tgttcagcat cgatctgggc gtctcgttct gtaagcattc tcctagttac tgatgacttt    120
cctctcttat ctgtattccg tgaaagagga gggccactgt cctctatata gtttatggat    180
ataaaaagtt tgagcttctt gccaatatga aacagatttc cccacattaa gagctgtttc    240
tctataggtt tccaatcaat attagtgccg tcaaaacgtt tgttcagatc agattgtcca    300
cgttcgttta cagatactct gactgtagta tcatctgatc tcacacgttg gttgtgacgt    360 attttcgac gcataacatt ttcagcatcc tgtgttatct tcgcccagtg tgaactgggt    420
gctacagcca agtcctgttc agtgtccttt gacacagttc ggttgttcag agttaccttc    480
cactcaatag tataatgaat acaaggcttt cctctatgtt gcctcgtagt cctttcttcg    540
ggctcctgga agaaacccag atgattgggc tgggattgat gcaagggagt ataaggttca    600
tcaagtacat gttcaggtga tgggcaaaat acgatggcg tacgatctct accgaagtca    660
ccaggggtgg gggcatacga tggagtttgt atccacggat caggtggctg aagctgagag    720
gcatcgtcat cgtagtaagg actaaacgtc atcccctcaa ggcagtagat gccactgaga    780
agcctagtgt tgggatcatc atatgttagc ctacaccata tgggtgtccc agcaagagtg    840
tccgtgaggg aagaggtgca gctaacaaaa ccagtaaaat gatcaggttc atggacaatg    900
aactaagaca ggtacagtat tgtagcccta cccgtcttgg ttaacctggt aaggtcaaaa    960
aggatcgaac cgtggctcag tacaaacaaa ggaatgttta acagtttgcg ggagatgcaa   1020
ggcacatgct ttgtcatgtt tgacgcgttt gcagtgtaga agcttccagc taccgtagat   1080
tactgataca aactcaatac actatttcta taaccttact gttcaataca gtacgatcaa   1140
aatttccgga atattaatgt tacggttacc ttccatatgt agactagcgc acttggcatt   1200
agggttcgaa atacgatcaa agagtattgg gggggtgac agcagtaatg actccaactg   1260
taaatcggct tctaggcgcg ctccatctaa atgttctggc tgtggtgtac aggggcataa   1320
aattacgcac tacccgaatc gatagaacta ctcattttta tatagaagtc agaattcatg   1380
gtgttttgat cattttaaat ttttatatgg cgggtggtgg gcaactcgct tgcgcgggca   1440
```

```
actcgcttac cgattacgtt agggctgata tttacgtaaa aatcgtcaag ggatgcaaga    1500
ccaaagtact aaaaccccgg agtcaacagc atccaagccc aagtccttca cggagaaacc    1560
ccagcgtcca catcacgagc gaaggaccac ctctaggcat cggacgcacc atccaattag    1620
aagcagcaaa gcgaaacagc ccaagaaaaa ggtcggcccg tcggcctttt ctgcaacgct    1680
gatcacgggc agcgatccaa ccaacaccct ccagagtgac tagggcgga aatttatcgg     1740 gattaatttc cactcaacca caaatcacag tcgtccccgg tattgtcctg cagaatgcaa    1800
tttaaactct tctgcgaatc gcttggattc cccgcccctg gccgtagagc ttaaagtatg    1860
tcccttgtcg atgcgatgta tcacaacata taaatactag caagggatgc catgcttgga    1920
ggatagcaac cgacaacatc acatcaagct ctcccttctc tgaacaataa accccacaca    1980
ccgtcaaaat ggtcgcgtgg tggtctctat ttctgtacgg ccttcaggtc gcggcacctg    2040
ctttggctgc aacgcctgcg gactggcgat cgcaatccat ttatttcctt ctcacggatc    2100
gatttgcaag gacggatggg tcgacgactg cgacttgtaa tactgcggat cagaaatact    2160
gtggtggaac atggcagggc atcatcgaca agttggacta tatccaggga atgggcttca    2220
cagccatctg gatcaccccc gttacagccc agctgcccca gaccaccgca tatggagatg    2280
cctaccatgg ctactggcag caggatatat actctctgaa cgaaaactac ggcactgcag    2340
atgacttgaa ggcgctctct tcggcccttc atgagagggg gatgtatctt atggtcgatg    2400
tggttgctaa ccatatgggc tatgatggag cgggtagctc agtcgattac agtgtgttta    2460
aaccgttcag ttcccaagac tacttccacc cgttctgttt cattcaaaac tatgaagatc    2520
agactcaggt tgaggattgc tggctaggag ataacactgt ctccttgcct gatctcgata    2580
ccaccaagga tgtggtcaag aatgaatggt acgactgggg gggatcattg gtatcgaact    2640
actccattga cggcctccgt atcgacacag taaaacacgt ccagaaggac ttctggcccg    2700
ggtacaacaa agccgcaggc gtgtactgta tcggcgaggt gctcgacggt gatccggcct    2760
acacttgtcc ctaccagaac gtcatggacg gcgtactgaa ctatcccatt tactatccac    2820
tcctcaacgc cttcaagtca acctccggca gcatggacga cctctacaac atgatcaaca    2880
ccgtcaaatc cgactgtcca gactcaacac tcctgggcac attcgtcgag aaccacgaca    2940
acccacggtt cgcttcttac accaacgaca tagccctcgc caagaacgtc gcagcattca    3000
tcatcctcaa cgacggaatc cccatcatct acgccggcca agaacagcac tacgccggcg    3060
gaaacgaccc cgcgaaccgc gaagcaacct ggctctcggg ctacccgacc gacagcgagc    3120
tgtacaagtt aattgcctcc gcgaacgcaa tccggaacta tgccattagc aaagatacag    3180
gattcgtgac ctacaagaac tggcccatct acaaagacga cacaacgatc gccatgcgca    3240
agggcacaga tgggtcgcag atcgtgacta tcttgtccaa caagggtgct tcgggtgatt    3300 cgtatacct ctccttgagt ggtgcgggtt acacagccgg ccagcaattg acggaggtca     3360
ttggctgcac gaccgtgacg gttggttcgg atggaaatgt gcctgttcct atggcaggtg    3420
ggctacctag ggtattgtat ccgactgaga agttggcagg tagcaagatc tgtagtagct    3480
cgtaaattaa ttaa                                                      3494
```

<210> SEQ ID NO 34
<211> LENGTH: 3494
<212> TYPE: DNA
<213> ORGANISM: Artificial Sequence
<220> FEATURE:
<223> OTHER INFORMATION: Description of Artificial Sequence: Synthetic polynucleotide
<220> FEATURE:

```
<223> OTHER INFORMATION: Nucleotide seq with the Aspergillus niger alpha
      amylase promoter with optimized codon frequency and modified
      translational initiator seq and the alpha amylase nucleotide
      coding seq with modified translational terminator sequence
<220> FEATURE:
<221> NAME/KEY: promoter
<222> LOCATION: (1)..(1988)
<220> FEATURE:
<221> NAME/KEY: misc_feature
<222> LOCATION: (1979)..(1988)
<223> OTHER INFORMATION: translational initiator sequence
<220> FEATURE:
<221> NAME/KEY: gene
<222> LOCATION: (1989)..(3494)

<400> SEQUENCE: 34
ctcgagggac aacgcatcgt ttgatacact tcccgccaat atggacgttg tccagaagcc      60
tgttcagcat cgatctgggc gtctcgttct gtaagcattc tcctagttac tgatgacttt     120
cctctcttat ctgtattccg tgaaagagga gggccactgt cctctatata gtttatggat     180
ataaaaagtt tgagcttctt gccaatatga aacagatttc cccacattaa gagctgtttc     240
tctataggtt tccaatcaat attagtgccg tcaaaacgtt tgttcagatc agattgtcca     300
cgttcgttta cagatactct gactgtagta tcatctgatc tcacacgttg gttgtgacgt     360
atttttcgac gcataacatt ttcagcatcc tgtgttatct tcgcccagtg tgaactgggt     420
gctacagcca agtcctgttc agtgtccttt gacacagttc ggttgttcag agttaccttc     480
cactcaatag tataatgaat acaaggcttt cctctatgtt gcctcgtagt cctttcttcg     540
ggctcctgga agaaacccag atgattgggc tgggattgat gcaagggagt ataaggttca     600
tcaagtacat gttcaggtga tgggcaaaat acggatggcg tacgatctct accgaagtca     660
ccaggggtgg gggcatacga tggagtttgt atccacggat caggtggctg aagctgagag     720
gcatcgtcat cgtagtaagg actaaacgtc atcccctcaa ggcagtagat gccactgaga     780
agcctagtgt tgggatcatc atatgttagc ctacaccata tgggtgtccc agcaagagtg     840
tccgtgaggg aagaggtgca gctaacaaaa ccagtaaaat gatcaggttc atggacaatg     900
aactaagaca ggtacagtat tgtagcccta cccgtcttgg ttaacctggt aaggtcaaaa     960
aggatcgaac cgtggctcag tacaaacaaa aggaatgtta acagtttgcg ggagatgcaa    1020
ggcacatgct ttgtcatgtt tgacgcgttt gcagtgtaga agcttccagc taccgtagat    1080
tactgataca aactcaatac actatttcta taaccttact gttcaataca gtacgatcaa    1140
aatttccgga atattaatgt tacggttacc ttccatatgt agactagcgc acttggcatt    1200
agggttcgaa atacgatcaa agagtattgg gggggtgac agcagtaatg actccaactg    1260
taaatcggct tctaggcgcg ctccatctaa atgttctggc tgtggtgtac aggggcataa    1320
aattacgcac tacccgaatc gatagaacta ctcattttta tatagaagtc agaattcatg    1380
gtgttttgat cattttaaat ttttatatgg cgggtggtgg gcaactcgct tgcgcgggca    1440
actcgcttac cgattacgtt agggctgata tttacgtaaa aatcgtcaag ggatgcaaga    1500
ccaaagtact aaaacccccgg agtcaacagc atccaagccc aagtccttca cggagaaacc    1560
ccagcgtcca catcacgagc gaaggaccac ctctaggcat cggacgcacc atccaattag    1620
aagcagcaaa gcgaaacagc ccaagaaaaa ggtcggcccg tcggcctttt ctgcaacgct    1680
gatcacgggc agcgatccaa ccaacaccct ccagagtgac taggggcgga aatttatcgg    1740
gattaatttc cactcaacca caaatcacag tcgtccccgg tattgtcctg cagaatgcaa    1800
tttaaactct tctgcgaatc gcttggattc cccgccctg gccgtagagc ttaaagtatg    1860
```

-continued

```
tcccttgtcg atgcgatgta tcacaacata taaatactag caagggatgc catgcttgga    1920
ggatagcaac cgacaacatc acatcaagct ctcccttctc tgaacaataa accccacaca    1980
ccgtcaaaat ggtcgcctgg tggtccctgt tcctctacgg acttcaggtg gctgccccc    2040 ctctcgccgc gaccccgcc gattggcgta gccagtcgat ttacttcttg cttactgacc    2100
gcttcgctcg caccgacggt tccaccaccg ccacctgcaa cactgcggac cagaagtact    2160
gcggcggcac ttggcagggt atcatcgaca agctggatta catccagggt atgggattca    2220
ccgctatctg gattactcct gttaccgctc agctccccca gaccaccgcc tacggcgatg    2280
cctaccacgg ttactggcag caggacatct actctctgaa cgaaaactac ggtaccgctg    2340
acgatctcaa ggccttgtct tccgccctcc acgagcgtgg catgtacctg atggtcgacg    2400
tcgtggctaa ccacatgggt tacgacggtg cgggcagctc tgtcgattac tcggttttca    2460
agcctttctc ctcccaggat tacttccacc ccttctgctt catccagaac tacgaggacc    2520
agacccaggt cgaggactgc tggctgggag acaacactgt ttcgcttccc gatctcgaca    2580
ctaccaagga cgtcgttaag aacgagtggt acgattgggt gggtagcttg gtctccaact    2640
acagcattga cggcctccgc atcgacaccg tcaagcacgc ccagaaggat ttctggcctg    2700
gatacaacaa ggccgccggt gtgtactgca tcggcgaagt tctggacggt gaccctgctt    2760
acacctgccc ctaccagaac gtcatggatg gtgtcctgaa ctaccccatc tactaccccc    2820
ttctcaacgc tttcaagtct acctccggct ccatggacga cctctacaac atgattaaca    2880
ctgttaagag cgattgccct gactcgaccc tgttgggcac cttcgtggag aaccacgata    2940
accccgtttt cgcctcctac actaacgaca tcgcccttgc gaagaacgtc gctgccttca    3000
tcatcctcaa cgacggtatt cctatcatct acgctggtca ggagcagcac tacgccggcg    3060
gaaacgatcc cgctaaccgc gaagccacct ggctgtccgg ttaccccacc gactctgagc    3120
tctacaagct gatcgctagc gccaacgcga ttcgtaacta cgccatctcc aaggacactg    3180
gcttcgtcac ctacaagaac tggcctatct acaaggatga caccactatc gctatgcgta    3240
agggtaccga cggttctcag atcgttacca ttttgtccaa caagggagcc agcggtgatt    3300
cctacaccct ctctctgtcc ggcgctggct acactgccgg tcagcagctt accgaggtca    3360
tcggatgcac cactgtcacc gtgggttcgg acggcaacgt tcccgtcccc atggctggtg    3420
gcctccctcg cgtcctgtac cccaccgaga agctcgccgg ttctaagatc tgctccagct    3480
cctaaattaa ttaa                                                      3494
```

<210> SEQ ID NO 35
<211> LENGTH: 1265
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Recombinant fusion construct, generated by PCR, of a promoter fragment and a gene fragment
<220> FEATURE:
<221> NAME/KEY: promoter
<222> LOCATION: (1)..(205)
<220> FEATURE:
<221> NAME/KEY: gene
<222> LOCATION: (206) . . . (1265)

<400> SEQUENCE: 35

```
ggaattcaag ctagatgcta agcgatattg catggcaata tgtgttgatg catgtgcttc      60
ttccttcagc ttcccctcgt gcagatgagg tttggctata aattgaagtg gttggtcggg     120
```

```
gttccgtgag gggctgaagt gcttcctccc ttttagacgc aactgagagc ctgagcttca    180
tccccagcat cattactcct tcaccatgtt ctctctcgcc cgccttggta ccgtcgctgg    240
tctcttcctt ctcgctcagg ctgccccgc ttccctgcgc cgtggtatgt ttattttctc    300
cacaacttgt aacacagcat tcgcttgagc cagactgacg gatttagacg tctcctcttc    360
ccttctcaac aacctggacc tcttcgctca gtacagcgcc gccgcttact gcgatgagaa    420
cctgaactct accggtacca agttgacctg ctctgttggc aactgccctc ttgtcgaggc    480
ggcctctacc cagtccttgg atgagttcaa cgagtaagtc accgcaaata tacaattcta    540
gttcataagc aactactgac aactcagatc gtcctcctac ggcaaccccg ccggttacct    600
cgccgctgac gagactaaca agctcctcgt cctgtccttc cgtggtagcg ctgaccttgc    660
caactgggtc gccaacctga acttcggtct cgaggacgcc agcgatctgt gctctggttg    720
cgaagtccac tccggcttct ggaaggcttg gtctgagatc gccgacacca tcacttccaa    780
ggtggaatcc gctttgtcgg atcactccga ttactccctc gtcttgaccg gtcactcgta    840
cggcgctgcg ctggccgccc tcgccgcgac tgctctgcgt aactccggcc actcggttga    900
gctggtaagt tatcctcatt ttgtaagtga cggtgcgcca aatctgacca aatagtacaa    960
ctacggtcag cctcgccttg gcaacgaggc cctcgccacc tacatcaccg accagaacaa   1020
gggtggcaac taccgcgtta cccacactaa cgacatcgtc cctaagctgc ccccaccct   1080 gctcggttac caccacttca gccccgagta ctacatcagc agcgccgacg aggccaccgt   1140
gaccaccact gacgtgactg aggttaccgg aatcgatgct accggcggta acgatggaac   1200
cgacggaact agcatcgacg ctcaccgttg gtacttcatt tacatttccg aatgctccta   1260
aatac                                                              1265
```

<210> SEQ ID NO 36
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (4)..(5)
<223> OTHER INFORMATION: a, c, t, g, unknown or other

<400> SEQUENCE: 36
nycnnhcacc atg                                                       13

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cccgccgccr ccatgg                                                    16

<210> SEQ ID NO 38
<211> LENGTH: 10
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 38
aacagccaaa                                                          10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
aacagtcaaa                                                          10

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aacatccaaa                                                          10

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
aacattcaaa                                                          10

<210> SEQ ID NO 42
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aaccgccaaa                                                          10

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aaccgtcaaa                                                          10

<210> SEQ ID NO 44
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 44
aacctccaaa                                                            10

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aaccttcaaa                                                            10

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aactgccaaa                                                            10

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aactgtcaaa                                                            10

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aacttccaaa                                                            10

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aactttcaaa                                                            10

<210> SEQ ID NO 50
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 50
atcagccaaa                                                              10

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
atcagtcaaa                                                              10

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
atcatccaaa                                                              10

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
atcattcaaa                                                              10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
atccgccaaa                                                              10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
atccgtcaaa                                                              10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Synthetic
```

```
                                   oligonucleotide

<400> SEQUENCE: 56
atcctccaaa                                                                 10

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
atccttcaaa                                                                 10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
atctgccaaa                                                                 10

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
atctgtcaaa                                                                 10

<210> SEQ ID NO 60
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
atcttccaaa                                                                 10

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
atctttcaaa                                                                 10

<210> SEQ ID NO 62
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 62
cacagccaaa                                                             10

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cacagtcaaa                                                             10

<210> SEQ ID NO 64
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cacatccaaa                                                             10

<210> SEQ ID NO 65
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cacattcaaa                                                             10

<210> SEQ ID NO 66
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
caccgccaaa                                                             10

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cacctccaaa                                                             10

<210> SEQ ID NO 68
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 68
caccttcaaa                                                          10

<210> SEQ ID NO 69
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cactgccaaa                                                          10

<210> SEQ ID NO 70
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cactgtcaaa                                                          10

<210> SEQ ID NO 71
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cacttccaaa                                                          10

<210> SEQ ID NO 72
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cactttcaaa                                                          10

<210> SEQ ID NO 73
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ctcagccaaa                                                          10

<210> SEQ ID NO 74
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
```
ctcagtcaaa                                                          10

<210> SEQ ID NO 75
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctcatccaaa                                                          10

<210> SEQ ID NO 76
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ctcattcaaa                                                          10

<210> SEQ ID NO 77
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ctccgccaaa                                                          10

<210> SEQ ID NO 78
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ctccgtcaaa                                                          10

<210> SEQ ID NO 79
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ctcctccaaa                                                          10

<210> SEQ ID NO 80
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80

```
ctccttcaaa                                                          10

<210> SEQ ID NO 81
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ctctgccaaa                                                          10

<210> SEQ ID NO 82
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ctctgtcaaa                                                          10

<210> SEQ ID NO 83
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ctcttccaaa                                                          10

<210> SEQ ID NO 84
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ctctttcaaa                                                          10

<210> SEQ ID NO 85
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aacagccaca                                                          10

<210> SEQ ID NO 86
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aacagtcaca                                                          10
```

<210> SEQ ID NO 87
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aacatccaca                                                          10

<210> SEQ ID NO 88
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
aacattcaca                                                          10

<210> SEQ ID NO 89
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
aaccgccaca                                                          10

<210> SEQ ID NO 90
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
aaccgtcaca                                                          10

<210> SEQ ID NO 91
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
aacctccaca                                                          10

<210> SEQ ID NO 92
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
aaccttcaca                                                          10

<210> SEQ ID NO 93
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
aactgccaca                                                            10

<210> SEQ ID NO 94
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
aactgtcaca                                                            10

<210> SEQ ID NO 95
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aacttccaca                                                            10

<210> SEQ ID NO 96
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
aactttcaca                                                            10

<210> SEQ ID NO 97
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
atcagccaca                                                            10

<210> SEQ ID NO 98
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
atcagtcaca                                                            10

```
<210> SEQ ID NO 99
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
atcatccaca                                                              10

<210> SEQ ID NO 100
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
atcattcaca                                                              10

<210> SEQ ID NO 101
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
atccgccaca                                                              10

<210> SEQ ID NO 102
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
atccgtcaca                                                              10

<210> SEQ ID NO 103
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
atcctccaca                                                              10

<210> SEQ ID NO 104
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
atccttcaca                                                              10

<210> SEQ ID NO 105
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
atctgccaca                                                                10

<210> SEQ ID NO 106
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
atctgtcaca                                                                10

<210> SEQ ID NO 107
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
atcttccaca                                                                10

<210> SEQ ID NO 108
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
atctttcaca                                                                10

<210> SEQ ID NO 109
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
cacagccaca                                                                10

<210> SEQ ID NO 110
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cacagtcaca                                                                10

<210> SEQ ID NO 111
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cacatccaca                                                                10

<210> SEQ ID NO 112
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
cacattcaca                                                                10

<210> SEQ ID NO 113
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
caccgccaca                                                                10

<210> SEQ ID NO 114
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
caccgtcaca                                                                10

<210> SEQ ID NO 115
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cacctccaca                                                                10

<210> SEQ ID NO 116
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
caccttcaca                                                                10

<210> SEQ ID NO 117
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 117
cactgccaca                                                              10

<210> SEQ ID NO 118
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
cactgtcaca                                                              10

<210> SEQ ID NO 119
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
cacttccaca                                                              10

<210> SEQ ID NO 120
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cactttcaca                                                              10

<210> SEQ ID NO 121
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ctcagccaca                                                              10

<210> SEQ ID NO 122
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ctcagtcaca                                                              10

<210> SEQ ID NO 123
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 123
ctcatccaca                                                                10

<210> SEQ ID NO 124
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ctcattcaca                                                                10

<210> SEQ ID NO 125
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ctccgccaca                                                                10

<210> SEQ ID NO 126
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ctccgtcaca                                                                10

<210> SEQ ID NO 127
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ctcctccaca                                                                10

<210> SEQ ID NO 128
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ctccttcaca                                                                10

<210> SEQ ID NO 129
<211> LENGTH: 10
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 129
ctctgccaca                                                             10

<210> SEQ ID NO 130
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ctctgtcaca                                                             10

<210> SEQ ID NO 131
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ctcttccaca                                                             10

<210> SEQ ID NO 132
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ctctttcaca                                                             10

<210> SEQ ID NO 133
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
aacagccaag                                                             10

<210> SEQ ID NO 134
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
aacagtcaag                                                             10

<210> SEQ ID NO 135
<211> LENGTH: 10
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 135
aacatccaag                                                                10

<210> SEQ ID NO 136
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
aacattcaag                                                                10

<210> SEQ ID NO 137
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
aaccgccaag                                                                10

<210> SEQ ID NO 138
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
aaccgtcaag                                                                10

<210> SEQ ID NO 139
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
aacctccaag                                                                10

<210> SEQ ID NO 140
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
aaccttcaag                                                                10

<210> SEQ ID NO 141
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 141
aactgccaag                                                                10

<210> SEQ ID NO 142
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
aactgtcaag                                                                10

<210> SEQ ID NO 143
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
aacttccaag                                                                10

<210> SEQ ID NO 144
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
aactttcaag                                                                10

<210> SEQ ID NO 145
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
atcagccaag                                                                10

<210> SEQ ID NO 146
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
atcagtcaag                                                                10

<210> SEQ ID NO 147
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 147
atcatccaag                                                          10

<210> SEQ ID NO 148
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
atcattcaag                                                          10

<210> SEQ ID NO 149
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
atccgccaag                                                          10

<210> SEQ ID NO 150
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
atccgtcaag                                                          10

<210> SEQ ID NO 151
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
atcctccaag                                                          10

<210> SEQ ID NO 152
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152 atcctttcaag                                                         10

<210> SEQ ID NO 153
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
```
atctgccaag                                                           10

<210> SEQ ID NO 154
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
atctgtcaag                                                           10

<210> SEQ ID NO 155
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
atcttccaag                                                           10

<210> SEQ ID NO 156
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
atcttTcaag                                                           10

<210> SEQ ID NO 157
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
cacagccaag                                                           10

<210> SEQ ID NO 158
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cacagtcaag                                                           10

<210> SEQ ID NO 159
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159

-continued cacatccaag 10

<210> SEQ ID NO 160
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cacattcaag 10

<210> SEQ ID NO 161
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
caccgccaag 10

<210> SEQ ID NO 162
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
caccgtcaag 10

<210> SEQ ID NO 163
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
cacctccaag 10

<210> SEQ ID NO 164
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
caccttcaag 10

<210> SEQ ID NO 165
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
cactgccaag 10

<210> SEQ ID NO 166
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cactgtcaag                                                          10

<210> SEQ ID NO 167
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cacttccaag                                                          10

<210> SEQ ID NO 168
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
cactttcaag                                                          10

<210> SEQ ID NO 169
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ctcagccaag                                                          10

<210> SEQ ID NO 170
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ctcagtcaag                                                          10

<210> SEQ ID NO 171
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ctcatccaag                                                          10

```
<210> SEQ ID NO 172
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ctcattcaag                                                          10

<210> SEQ ID NO 173
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ctccgccaag                                                          10

<210> SEQ ID NO 174
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ctccgtcaag                                                          10

<210> SEQ ID NO 175
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ctcctccaag                                                          10

<210> SEQ ID NO 176
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ctccttcaag                                                          10

<210> SEQ ID NO 177
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
ctctgccaag                                                          10
```

<210> SEQ ID NO 178
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ctctgtcaag                                                          10

<210> SEQ ID NO 179
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ctcttccaag                                                          10

<210> SEQ ID NO 180
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
ctctttcaag                                                          10

<210> SEQ ID NO 181
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
cacctcagca atg                                                      13

<210> SEQ ID NO 182
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
atggcttcct tc                                                       12

<210> SEQ ID NO 183
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ggcatttatg atg                                                      13

<210> SEQ ID NO 184

```
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gaaggcattt atg                                                          13

<210> SEQ ID NO 185
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
caccgtcaaa atg                                                          13

<210> SEQ ID NO 186
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cacctcagca atgtttagtc tc                                                22

<210> SEQ ID NO 187
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
caccgtcaaa atgtttagtc tc                                                22

<210> SEQ ID NO 188
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cgcagtcaag atgtttagtc tc                                                22

<210> SEQ ID NO 189
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cacctcagca atgttctctc tc                                                22

<210> SEQ ID NO 190
<211> LENGTH: 22
```

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 190
caccgtcaaa atgttctctc tc    22

<210> SEQ ID NO 191
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 191
cgcagtcaag atgttctctc tc    22

<210> SEQ ID NO 192
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 192
ctccttcacc atgttctctc tc    22

<210> SEQ ID NO 193
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 193
cacctcagca    10

<210> SEQ ID NO 194
<211> LENGTH: 888
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 194

```
atgttctctc tcgcccgcct tggtaccgtc gctggtctct tccttctcgc tcaggctgcc      60
cccgcttccc tgcgccgtga cgtctcctct tcccttctca caacctggac cctcttcgct     120
cagtacagcg ccgccgctta ctgcgatgag aacctgaact ctaccggtac caagttgacc     180
tgctctgttg gcaactgccc tcttgtcgag gcggcctcta cccagtcctt ggatgagttc     240
aacgaatcgt cctcctacgg caaccccgcc ggttacctcg ccgctgacga gactaacaag     300
ctcctcgtcc tgtccttccg tggtagcgct gaccttgcca actgggtcgc caacctgaac     360
ttcggtctcg aggacgccag cgatctgtgc tctggttgcg aagtccactc cggcttctgg     420
aaggcttggt ctgagatcgc cgacaccatc acttccaagg tggaatccgc tttgtcggat     480
cactccgatt actccctcgt cttgaccggt cactcgtacg gcgctgcgct ggccgccctc     540
gccgcgactg ctctgcgtaa ctccggccac tcggttgagc tgtacaacta cggtcagcct     600
```

-continued

```
cgccttggca acgaggccct cgccacctac atcaccgacc agaacaaggg tggcaactac      660
cgcgttaccc acactaacga catcgtccct aagctgcccc ccaccctgct cggttaccac      720
cacttcagcc ccgagtacta catcagcagc gccgacgagg ccaccgtgac caccactgac      780
gtgactgagg ttaccggaat cgatgctacc ggcggtaacg atggaaccga cggaactagc      840
atcgacgctc accgttggta cttcatttac atttccgaat gctcctaa                  888
```

METHOD FOR PRODUCING A COMPOUND OF INTEREST IN A FILAMENTOUS FUNGAL CELL

This application is a U.S. national stage of International Patent Application No. PCT/EP2006/050398, filed 24 Jan. 2006, which designated the U.S. and claims priority benefit of EP 05100408.3, filed 24 Jan. 2005; the entire contents of each of which are hereby incorporated by reference.

FIELD OF THE INVENTION

The present invention relates to a method for producing a compound of interest in a filamentous fungal cell, wherein the nucleotide sequence encoding the compound of interest and/or control nucleotide sequences operatively associated thereto have been modified to get improved expression of the nucleotide sequence encoding the compound of interest and/or improved production of the compound of interest.

BACKGROUND OF THE INVENTION

The present invention relates to improved methods for producing a compound of interest. Numerous approaches have been applied to date in generating strains for protein over-expression and/or production. This includes, but is not limited to, making strains with multi-copies of the gene encoding the compound of interest and applying strong promoter sequences.

Each specific amino acid is encoded by a minimum of one codon and a maximum of six codons. Prior research has shown that codon usage in genes encoding the cell's polypeptides is biased among species (Kanaya, S, Y. Yamada, Y. Kudo and T. Ikemura (1999) Studies of codon usage and tRNA genes at 18 unicellular organisms and quantification of *Bacillus subtilis* tRNAs: gene expression level and species-specific diversity of codon usage based on multivariate analysis. *Gene* 238:143-155). Prior publications disclose optimization of codon use in a given host cell to improve polypeptide production (as example see WO 97/11086). More specifically, WO 03/70957 describes optimized codon use in filamentous fungi for producing plant polypeptides. In all these cases of 'classic' codon optimization, a native codon has been substituted by the most frequent codon from a reference set of genes, whereas the rate of codon translation for each amino acid is designed to be high (optimized). However, this 'classic' codon optimization neglects the other codons for which tRNAs are still available.

Recently, in WO 03/85114 a harmonization of codon use was described which takes into effect the distribution of optimal and non-optimal codons in genes, assuming that these effect protein folding. Using this method of harmonization of codon use for a gene results in the substitution of good (bad) codons in the donor organism by good (bad) ones in the host organism. However, this method of codon harmonization (WO 03/085114) neglects non-optimal codons since they are not replaced by more optimal ones. Additionally, the method cannot be applied to homologous genes. Another publication describes an additional way to improve polypeptide production in a host cell by using an improved consensus translational initiator sequence (U.S. Pat. No. 6,461,837 B1); the consensus sequence 5'-nyCnnhCACC(ATG)-3' (SEQ ID NO: 36) is claimed.

There is still a need for improved methods for producing a polypeptide in a filamentous fungal cell.

DESCRIPTION OF THE FIGURES

FIG. 2 depicts a plasmid map of expression vector pGBFINPLA-1a. FIG. 2 also provides a representative map for plasmid pGBFINPLA-1b and pGBFINPLA-1c. Indicated are the glaA flanking regions relative to the glaA promoter and the *A. oryzae* genomic pla1 gene encoding phospholipase A1. The *E. coli* DNA can be removed by digestion with restriction enzyme NotI, prior to transformation of the *A. niger* strains.

FIG. 4 also provides a representative map for plasmid pGBFINFUA-2 and pGBFINFUA-3. All clones originate from the pGBFIN-12 (described in WO99/32617) expression vector. Indicated are the glaA flanking regions relative to the variant sequences of the amyA promoter and the *A. niger* amyA cDNA sequence encoding alpha-amylase. The *E. coli* DNA can be removed by digestion with restriction enzyme NotI, prior to transformation of the *A. niger* strains.

DETAILED DESCRIPTION OF THE INVENTION

Figure 1:
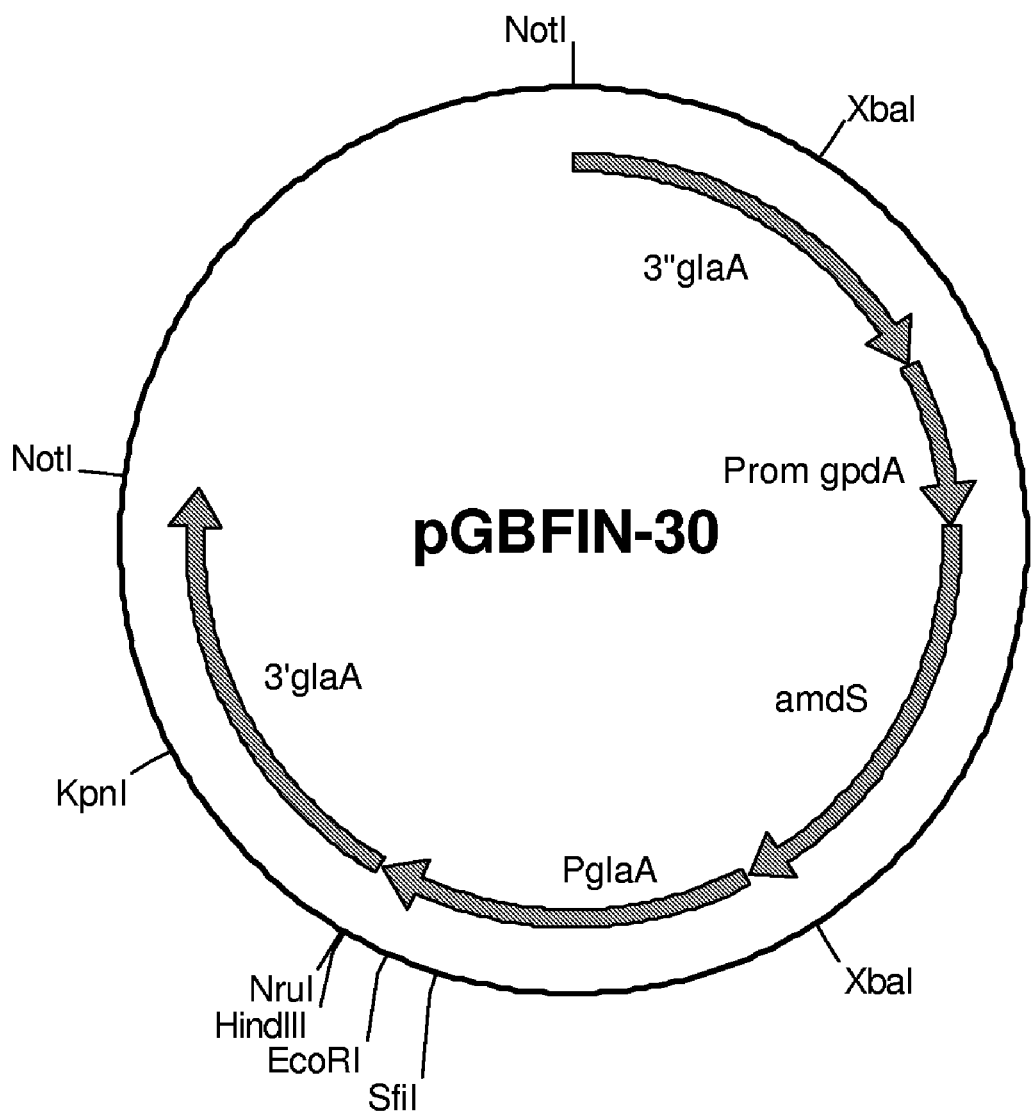
FIG. 1 depicts a plasmid map of expression vector pGBFIN-30. Indicated are the glaA flanking regions relative to the glaA promoter with the unique SfiI and EcoRI cloning sites in the glucoamylase promoter followed by the HindIII and NruI cloning sites. The pGBFIN-30 vector is originating from pGBFIN-23 (which construction is described in WO99/32617), with the AscI-XhoI sites replaced by a single NruI restriction site. The *E. coli* DNA can be removed by digestion with restriction enzyme NotI, prior to transformation of the *A. niger* strains.

A new approach to improve production of a compound of interest in a filamentous fungal cell is proposed based on modification of the protein encoding or coding sequence and optionally the associated 'non-coding' or control sequences that might have impact on translation efficiency and/or efficiency of production of the compound of interest.

Nucleotide Sequences

According to a first aspect of the invention, there is provided a nucleotide sequence comprising:

a synonymous nucleotide coding sequence with optimized codon frequency such that a native codon has been exchanged with a synonymous codon, said synonymous codon encoding the same amino acid as the native codon and having a higher frequency in codon usage as defined in Table 1 than the native codon; and optionally said nucleotide sequence comprising control sequences such as:

one translational termination sequence orientated in 5' towards 3' direction selected from the following list of sequences: TAAG, TAGA and TAAA, preferably TAAA, and/or one translational initiator coding sequence orientated in 5' towards 3' direction selected from the following list of sequences: GCTACCCCC; GCTACCTCC; GCTAC-CCTC; GCTACCTTC; GCTCCCCCC; GCTCCCTCC; GCTCCCCTC; GCTCCCTTC; GCTGCCCCC; GCT-GCCTCC; GCTGCCCTC; GCTGCCTTC; GCTTC-CCCC; GCTTCCTCC; GCTTCCCTC; and GCTTC-CTTC (SEQ ID NO: 21), preferably GCT TCC TTC (SEQ ID NO: 21).

TABLE 1

Optimal filamentous fungal codon frequency for synonymous codons in %

| | .T. | .C. | .A. | .G. | |
|---|---|---|---|---|---|
| T.. | Phe | Ser | Tyr | Cys | ..T |
| | 0 | 21 | 0 | 0 | |
| T.. | Phe | Ser | Tyr | Cys | ..C |
| | 100 | 44 | 100 | 100 | |
| T.. | Leu | Ser | Stop | Stop | ..A |
| | 0 | 0 | 100 | 0 | |
| T.. | Leu | Ser | Stop | Trp | ..G |
| | 13 | 14 | 0 | 100 | |
| C.. | Leu | Pro | His | Arg | ..T |
| | 17 | 36 | 0 | 49 | |
| C.. | Leu | Pro | His | Arg | ..C |
| | 38 | 64 | 100 | 51 | |
| C.. | Leu | Pro | Gln | Arg | ..A |
| | 0 | 0 | 0 | 0 | |
| C.. | Leu | Pro | Gln | Arg | ..G |
| | 32 | 0 | 100 | 0 | |
| A.. | Ile | Thr | Asn | Ser | ..T |
| | 27 | 30 | 0 | 0 | |
| A.. | Ile | Thr | Asn | Ser | ..C |
| | 73 | 70 | 100 | 21 | |
| A.. | Ile | Thr | Lys | Arg | ..A |
| | 0 | 0 | 0 | 0 | |
| A.. | Met | Thr | Lys | Arg | ..G |
| | 100 | 0 | 100 | 0 | |
| G.. | Val | Ala | Asp | Gly | ..T |
| | 27 | 38 | 36 | 49 | |
| G.. | Val | Ala | Asp | Gly | ..C |
| | 54 | 51 | 64 | 35 | |
| G.. | Val | Ala | Glu | Gly | ..A |
| | 0 | 0 | 26 | 16 | |
| G.. | Val | Ala | Glu | Gly | ..G |
| | 19 | 11 | 74 | 0 | |

According to a preferred embodiment, said nucleotide sequence is a sequence wherein the optimized codon frequency of said synonymous nucleotide coding sequence comprised in said nucleotide sequence is such that at least one native codon, preferably at least two native codons, more preferably at least three native codons, more preferably at least four native codons, more preferably at least five native codons, more preferably at least 1%, 2%, 3%, 4%, 5%, 10%, 15%, 20%, 25%, 50%, 75%, 80%, 85%, 90%, and most preferably at least 95% of the native codons have been exchanged with a synonymous codon, said synonymous codon encoding the same amino acid as the native codon and having a higher frequency in codon usage as defined in Table 1 than the native codon.

According to a more preferred embodiment, said nucleotide sequence is a sequence wherein the optimized codon frequency of said synonymous nucleotide coding sequence comprised in said nucleotide sequence is such that at least one native codon, preferably at least two native codons, more preferably at least three native codons, more preferably at least four native codons, more preferably at least five native codons, more preferably at least 1%, 2%, 3%, 4%, 5%, 10%, 15%, 20%, 25%, 50%, 75%, 80%, 85%, 90%, and most preferably at least 95% of the native codons have been exchanged with a synonymous codon, the synonymous codon changing the codon frequency such that the value of the absolute difference between the percentage for said synonymous codon in said frequency and the listed optimal percentage becomes smaller after modification, applying the following list of optimal percentages: cysteine by TGC (100%); phenylalanine by TTC (100%); histidine by CAC (100%); lysine by AAG (100%); asparagine by AAC (100%); glutamine by CAG (100%); tyrosine by TAC (100%); alanine is encoded by GCT (38%), GCC (51%), or GCG (11%); aspartate by GAC (64%); glutamate by GAG (74%); glycine by GGT (49%), GGC (35%), GGA (16%); isoleucine by ATT (27%), ATC (73%); leucine by TTG (13%), CTT (17%), CTC (38%), CTG (32%); proline by CCT (36%), CCC (64%); arginine by CGT (49%), CGC (51%); serine by TCT (21%), TCC (44%), TCG (14%), AGC (21%); threonine by ACT (30%), ACC (70%) and/or valine by GTT (27%), GTC (54%), GTG (19%).

According to an even more preferred embodiment, said nucleotide sequence is a sequence wherein the codon fitness of said synonymous nucleotide coding sequence with optimized codon frequency comprised in said nucleotide sequence has a fitness value that is at least 70%, 80%, 90%, 95%, preferably 96%, 97%, 98%, and most preferable >98%, where the codon fitness is the calculated by means of the following function:

$$fit_c(g) = 100 - \frac{1}{|g|} \cdot \sum_{k=1}^{|g|} |r_c^{target}(c(k)) - r_c^g(c(k))| \cdot 100$$

where g symbolizes a nucleotide coding sequence, |g| its length, g(k) its k-th codon, $r_c^{target}(c(k))$ is a desired ratio of codon c(k) and $r_c^g(c(k))$ an actual ratio in the nucleotide coding sequence g.

In the context of the invention, both nucleotide coding sequence and control sequence are herein named native or wild type when one refers to these sequences before the method of the invention has been applied to. Once having been modified by the invention, they would be named modified or synonymous sequences. Consequently, synonymous sequences would generally be recognized as recombinant sequences. Incidentally, a sequence occurring in nature may be identical to the synonymous sequence.

In the context of the invention, a nucleotide coding sequence and a synonymous nucleotide coding sequence may directly encode a compound of interest to be produced. The term compound of interest is defined later in the section "Production of a compound of interest". An example of a compound of interest that is directly encoded by a (synonymous) nucleotide coding sequence is a polypeptide, preferably, the polypeptide is an enzyme, more preferably an enzyme that is secreted outside the cell. Alternatively, the compound encoded by the (synonymous) nucleotide coding sequence may not be the compound of interest per se, but may inter alia be involved in the production of the compound of interest. In this case, the compound encoded by the (synonymous) nucleotide coding sequence can be, but is not limited to, an intracellular enzyme involved in the production of a metabolite, a transporter, a transcription factor, a structural protein, a chaperone or the product of a housekeeping gene.

In the context of the invention the term "codon" generally refers to a nucleotide triplet, which codes for an amino acid. As used herein "synonymous codon" refers to a codon which does not have the identical nucleotide sequence, but which encodes the identical amino acid (AA). The term "codon frequency", "codon bias", or "codon usage" is defined as the frequency at which the different corresponding codons are used in a coding sequence. Codon usage is based on the fact that several codons in a coding sequence encode the same amino acid, but that the frequency of the different codons encoding said amino acid may vary between various coding sequences.

A nucleotide coding sequence (encoding a polypeptide) that is homologous or heterologous to the host cell used for production may originate for example from a virus, a prokaryote, a fungus, a filamentous fungus, other eukaryotes and higher eukaryotes, like mammals, human and plants. This (native) nucleotide coding sequence is modified according to the optimal codon frequency as described in Table 1 (and further disclosed in paragraph "Calculation of "optimized codon frequency" or "optimized codon usage" using Table 1"), generating a synonymous nucleotide sequence. The native, coding sequence may be selected from the group of:
- a wild-type nucleotide sequence coding for a predetermined amino acid sequence,
- a back-translation of a natural occurring amino acid sequence using random choice for the codons,
- a non-naturally occurring amino acid sequence, displaying homology to a known amino acid sequence, e.g. a shuffled sequence,
- part of the sequences mentioned her above, e.g. to be used in fusion sequences.

The synonymous nucleotide coding sequence with optimized codon usage, is preferably expressed in an *Aspergillus*, *Trichoderma*, *Fusarium*, *Chrysosporum* or *Penicillium* host cell. More preferably the synonymous nucleotide coding sequence is expressed in an *Aspergillus niger*, *Aspergillus oryzae*, *Aspergillus sojae*, *Aspergillus terreus*, *Trichoderma reesei*, *Chrysosporum lucknowense* or *Penicillium chrysogenum* host cell. A most preferred *Aspergillus niger* host cell is CBS513.88 or derivatives thereof. Preferably, the expression of the product encoded by the synonymous coding sequence present is enhanced as compared to the production of the corresponding native coding sequence, said corresponding nucleic acid construct being present in the same copy number in a corresponding filamentous fungal host cell. Preferably, the modification of the nucleotide coding sequence, (resulting in a synonymous nucleotide coding sequence of the invention) results in an increase of at least 1%, 5%, 10%, 25%, 50%, 100%, 200%, 300%, 400% more preferably at least 500% of the yield of the compound of interest produced by the filamentous fungal host cell of the invention comprising a given copy number of the synonymous nucleotide coding sequence, as compared to the production of the native nucleotide coding sequences being present in the same copy number in a corresponding filamentous fungal host cell.

The increase in yield of the compound of interest to be produced may be determined by measuring the amount of compound produced by the filamentous fungal host cell of the invention and comparing it to the compound of interest produced by the corresponding filamentous fungal host cell. Determining the yield of compound of interest produced may be performed by measuring inter alia the amount of mRNA transcribed from the (synonymous) nucleotide coding sequence, the amount of polypeptide encoded by the mRNA, or the amount of compound (e.g. metabolite) in which' production the polypeptide encoded by the synonymous nucleotide coding sequence is involved with. Examples of methods known to the skilled person to determine the amount of mRNA include, but are not limited to Northern blot, Quantitative PCR, Real Time PCR, and micro-array analyses. The amount of polypeptide can inter alia be determined using protein measurement assays known to the skilled person. When the polypeptide is an enzyme, the amount of polypeptide can be measured using an activity assay specific for the concerned enzyme. The skilled person will know which assay to select for a specific enzyme. A preferred assay to determine the yield of the compound of interest to be produced is an activity assay specific for the concerned enzyme.

Considering the optimal codon usage as defined in Table 1 and codon bias between the genes of an organism, a native coding nucleotide sequence encoding a homologous polypeptide may also be considered subject to codon optimization and provide a higher yield for the homologous polypeptide than would the expression of the native nucleotide sequence in the same host.

In the context of this invention, a nucleotide coding sequence or coding sequence is defined as a nucleotide sequence encoding a polypeptide. The boundaries of the nucleotide coding sequence are generally determined by the ATG start codon located at the beginning of the open reading frame at the 5' end of the mRNA and a stop codon located just downstream of the open reading frame at the 3' end of the mRNA. A nucleotide coding sequence can include, but is not limited to, DNA, cDNA, RNA, and recombinant nucleic acid (DNA, cDNA, RNA) sequences. If the coding sequence is intended for expression in a eukaryotic cell, a polyadenylation signal and transcription termination sequence will usually be located 3' to the coding sequence. A nucleotide coding sequence comprises a translational initiator coding sequence, and optionally a signal sequence.

In order to attain expression of the nucleotide coding sequence, the nucleotide coding sequence is preferably combined with a control sequence. In the context of the invention, a control sequence is defined as a nucleotide sequence necessary or advantageous for expression of the nucleotide sequence encoding a polypeptide. When present together, the control sequence is operatively associated to the nucleotide coding sequence. The term "control sequence" includes all genetic elements necessary or advantageous for expression of a nucleotide coding sequence. Each control sequence may be native or foreign to the nucleotide coding sequence. Control sequences include, but are not limited to, a leader sequence, a polyadenylation sequence, a propeptide sequence, a promoter, a translational initiator sequence, a translational initiator coding sequence, a translational transcription terminator and a transcription terminator sequence. The control sequences may be provided with linkers, e.g., for the purpose of introducing specific restriction sites facilitating ligation of the control sequences with the coding region of the nucleotide sequence encoding a polypeptide.

The term "operatively associated" is defined herein as a configuration in which a control sequence is appropriately placed at a position relative to a (synonymous) nucleotide coding sequence such that the control sequence directs the expression of the (synonymous) nucleotide coding sequence.

In the context of this invention, the term "translational initiator coding sequence" is defined as the nine nucleotides immediately downstream of the initiator or start codon of the open reading frame of a DNA coding sequence. The initiator or start codon encodes for the AA methionine. The initiator codon is typically ATG, but may also be any functional start codon such as GTG. The term "consensus translational initiator coding sequence" is defined herein as the nine nucleotides immediately downstream of the initiator codon of the open reading frame of a DNA coding sequence and having the following DNA sequence: 5'-GCTnCCyyC-3' (i.e. SEQ ID NO. 20), using ambiguity codes for nucleotides y (C/T) and n (A/C/G/T). This leads to 16 variants for the translational initiator coding sequence: GCTACCCCC; GCTACCTCC; GCTACCCTC; GCTACCTTC; GCTCCCCCC; GCTCCCTCC; GCTCCCCTC; GCTCCCTTC; GCTGCCCCC; GCTGCCTCC; GCTGCCCTC; GCTGCCTTC; GCTTCCCCC; GCTTCCTCC; GCTTCCCTC; GCTTCCTTC (SEQ ID NO: 21). Preferably, the translational initiator coding sequence has the nucleic acid sequence: 5'-GCT TCC TTC-3' (i.e. SEQ ID NO. 21).

In the context of this invention, the term "translational termination sequence" is defined as the four nucleotides starting from the translational stop codon at the 3' end of the open reading frame or nucleotide coding sequence and oriented in 5' towards 3' direction. Preferably, the translational termination sequence is selected from the following list of sequences: 5'-TAAG-3', 5'-TAGA-3' and 5'-TAAA-3'. More preferably, the translational termination sequence is: 5'-TAAA-3'.

The term "optimized codon frequency" or "optimized codon usage" as used herein refers to a native nucleotide coding sequence, which has been modified wholly or partly to give a synonymous nucleotide coding sequence according to the codon usage as described in Table 1 (and further disclosed in paragraph "Calculation of "optimized codon frequency" or "optimized codon usage" using Table 1"). Optimizing codon frequency can be used to improve any coding sequence for any given polypeptide to be produced in any filamentous fungal species as host cell. Preferably, the filamentous fungal host cell is an *Aspergillus, Trichoderma, Fusarium, Chrysosporum* or *Penicillium* host cell. More preferably the filamentous fungal host cell is an *Aspergillus niger, Aspergillus oryzae, Aspergillus sojae, Aspergillus terreus, Trichoderma reesei, Chrysosporum lucknowense* or *Penicillium chrysogenum* host cell. A most preferred *Aspergillus niger* host cell is CBS513.88 or derivatives thereof. A more exhaustive list of the preferred host cells is given under the section "Host cells".

When the amino acid sequence of a polypeptide sequence has been determined, a nucleotide sequence encoding the polypeptide with optimized codon frequency for expression in the host cell or synonymous nucleotide coding sequence can be synthesized in which one or more of the native codons have been exchanged with a synonymous codon encoding the same amino acid, said synonymous codon having a higher frequency in the codon usage as defined in Table 1 (and further disclosed in paragraph "Method for producing a nucleotide sequence; calculation of the optimized codon frequency" using Table 1").

A nucleotide sequence encoding a polypeptide or synonymous coding sequence is considered to have an optimized codon frequency when at least one native codon, at least two native codons, at least three native codons, at least four native codons, at least five native codons or at least 1%, 2%, 3%, 4%, 5%, 10%, 15%, 20%, 25%, 50%, 75%, 80%, 85%, 90%, or preferably at least 95% of the native codons have been exchanged with a synonymous codon, the synonymous codon encoding the same amino acid as the native codon and having a higher frequency in the codon usage as defined in Table 1 than the native codon.

A nucleotide sequence encoding a polypeptide or synonymous coding sequence is considered to have an optimized codon frequency when at least one native codon, at least two native codons, at least three native codons, at least four native codons, at least five native codons or at least 1%, 2%, 3%, 4%, 5%, 10%, 15%, 20%, 25%, 50%, 75%, 80%, 85%, 90%, or preferably at least 95% of the native codons have been exchanged with a synonymous codon, the synonymous codon changing the codon frequency such that the value of the absolute difference between the percentage for said codon in said frequency and listed optimal percentage becomes smaller after modification, applying the following list of optimal percentages: cysteine by TGC (100%); phenylalanine by TTC (100%); histidine by CAC (100%); lysine by MG (100%); asparagine by AAC (100%); glutamine by CAG (100%); tyrosine by TAC (100%); alanine is encoded by GCT (38%), GCC (51%), or GCG (11%); aspartate by GAC (64%); glutamate by GAG (74%); glycine by GGT (49%), GGC (35%), GGA (16%); isoleucine by ATT (27%), ATC (73%); leucine by TTG (13%), CTT (17%), CTC (38%), CTG (32%); proline by CCT (36%), CCC (64%); arginine by CGT (49%), CGC (51%); serine by TCT (21%), TCC (44%), TCG (14%), AGC (21%); threonine by ACT (30%), ACC (70%) and/or valine by GTT (27%), GTC (54%), GTG (19%).

Codon fitness is defined to be the difference of the actual codon ratios in the gene and the target codon ratios, normalized for the number of occurrences of every codon. Let $r_{sc}^{target}(c(k))$ be the desired ratio (or frequency) of codon $c_k$ and $r_{sc}^{g}(c(k))$ as before the actual ratio in the gene g, then the single codon fitness is defined as:

$$fit_c(g) = 100 - \frac{1}{|g|} \cdot \sum_{k=1}^{|g|} |r_c^{target}(c(k)) - r_c^g(c(k))| \cdot 100$$

Thus, codon fitness $\{fit_c(g)\}$ can reach values between 0 and 100% with the optimal sequence being close to 100%. Consequently, a synonymous nucleotide coding sequence is considered to have an optimized codon frequency when the codon fitness value of the synonymous coding sequence is at least 70%, 80%, 90%, 95%, preferably 96%, 97%, 98%, and most preferable >98%.

The nucleotide sequence of the invention may be a synthetic nucleotide sequence. As used herein, the term "synthetic" gene, DNA construct, nucleic acid, polynucleotide, primer, or the like means a nucleotide sequence that is not found in nature; in other words, not merely a heterologous sequence to a particular organism, but one which is heterologous in the sense that it has been designed and/or created in a laboratory, and has been altered in some way that it does not have an identical nucleotide (or possibly AA) sequence to the one of its naturally occurring source, template or homologue. A synthetic nucleic acid or AA sequence as used herein can refer to a theoretical sequence or a tangibly, physically created embodiment. It is intended that synthetic sequences according to the invention are included in the invention in any form, e.g. paper or computer readable and physically created nucleic acid sequences, proteins, peptides, fused peptides or multi-peptides.

Alternative, a naturally occurring nucleotide sequence may display the features of the invention. The use of such sequence is considered to be encompassed within the invention.

The term "synthetic nucleotide construct" or "synthetic nucleic acid" can include nucleic acids derived or designed from wholly artificial amino acid sequences or nucleic acid sequences with single or multiple nucleotide changes compared to the naturally occurring sequence. These "synthetic DNA constructs" can be created by random or directed mutagenesis, DNA shuffling methods, DNA reassembly methods, gene synthesis, or by any means known to one skilled in the art (see for example Young and Dong, (2004), Nucleic Acids Research 32, (7) electronic access nar.oupjournals.org/cgi/reprint/32/7/e59 or Gupta et al. (1968), Proc. Natl. Acad. Sci USA, 60: 1338-1344; Scarpulla et al. (1982), Anal. Biochem. 121: 356-365; Stemmer et al. (1995), Gene 164: 49-53).

Alternatively, a synthetic nucleotide sequence may be designed from an amino acid sequence (see example 2). Using this reverse engineering method there is no need for a naturally occurring nucleotide sequence, which may not be available. A back-translation may first be performed using random choice for the codons. Subsequently, the resulting nucleotide sequence can be optimized for codon usage.

According to another preferred embodiment, a synonymous nucleotide coding sequence with optimized codon frequency according to the invention is a reverse engineered nucleotide coding sequence, wherein the optimized codon frequency is such that at least one codon, at least two codons, at least three codons, at least four codons, at least five codons or at least 1%, 2%, 3%, 4%, 5%, 10%, 15%, 20%, 25%, 50%, 75%, 80%, 85%, 90%, or preferably at least 95% of the codons have a higher frequency in the codon usage as defined in Table 1 than the codon usage that is predicted by the arithmetic average (i.e., 100% in case of 1 codon, 50% in case of two codons, 33.3% in case of 3 codons, 25% in case of 4 codons, and 16.7% in case of 6 codons).

According to a more preferred embodiment, said synonymous nucleotide coding sequence with optimized codon frequency is a reverse engineered nucleotide coding sequence wherein the codon fitness of the nucleotide coding sequence has a fitness value that is at least 70%, 80%, 90%, 95%, preferably 96%, 97%, 98%, and most preferable >98%, where the codon fitness is the calculated by means of the following function:

$$fit_c(g) = 100 - \frac{1}{|g|} \cdot \sum_{k=1}^{|g|} |r_c^{target}(c(k)) - r_c^g(c(k))| \cdot 100$$

where g symbolizes a nucleotide coding sequence, $|g|$ its length, $g(k)$ its k-th codon, $r_c^{target}(c(k))$ is a desired ratio of codon $c(k)$ and $r_c^g(c(k))$ a calculated ratio in the nucleotide coding sequence g.

In addition to the control sequences that may be present in the nucleotide sequence of the invention, the nucleotide coding sequence may comprise a signal sequence, or signal peptide-coding region.

A signal sequence codes for an amino acid sequence linked to the amino terminus of the polypeptide, which can direct the expressed polypeptide into the cell's secretory pathway. The 5'-end of the coding sequence of the nucleotide sequence may inherently contain a signal peptide-coding region naturally linked in translation reading frame with the segment of the coding region that encodes the secreted polypeptide of interest. In that case, the translational initiator coding sequence is part of the signal sequence. Alternatively, the 5'-end of the coding sequence may contain a signal peptide-coding region, which is foreign to that portion of the coding sequence that encodes the secreted protein. A foreign signal peptide-coding region may be required where the coding sequence does not normally contain a signal peptide-coding region. Alternatively, a foreign signal peptide-coding region may simply replace the natural signal peptide-coding region in order to obtain enhanced secretion of the protein(s) relative to the natural signal peptide-coding region normally associated with the coding sequence. The signal peptide-coding region may be obtained from a glucoamylase or an amylase gene from an *Aspergillus* species, a lipase or proteinase gene from a *Rhizomucor* species, the gene for the alpha-factor from *Saccharomyces cerevisiae*, an amylase or a protease gene from a *Bacillus* species, or the calf preprochymosin gene. However, any signal peptide-coding region capable of directing the expressed protein into the secretory pathway of a host cell of choice may be used in the present invention. Preferred signal peptide coding regions for filamentous fungus host cells are the signal peptide coding region obtained from *Aspergillus oryzae* TAKA amylase gene (EP 238 023), *Aspergillus niger* neutral amylase gene, *Aspergillus niger* glucoamylase, the *Rhizomucor miehei* aspartic proteinase gene, the *Humicola lanuginosa* cellulase gene, *Humicola insolens* cellulase, *Humicola insolens* cutinase, the *Candida antactica* lipase B gene or the *Rhizomucor miehei* lipase gene and mutant, truncated, and hybrid signal sequence thereof.

In another preferred embodiment, the synonymous nucleotide coding sequence with optimized coding frequency of the invention comprises a signal sequence. According to a more preferred embodiment, the signal sequence of the invention is a signal sequence with an optimized codon frequency where at least one native codon, or at least 1%, 5%, 10%, 25%, 50%, 75%, 80%, 85%, 90%, or preferably at least 95% of the native codons have been exchanged with a synonymous codon, said synonymous codon encoding the same amino acid as the native codon and having a higher frequency in codon usage than the native codon as defined in Table 1 and further disclosed in paragraph "Calculation of "optimized codon frequency" or "optimized codon usage" using Table 1". More preferably, the signal sequence of the invention comprises a translational initiator coding sequence having the following consensus DNA sequence: 5' GCTnCCyyC-3' (i.e. SEQ ID NO. 20) or even more preferably a translational initiator coding sequence with the nucleic acid sequence: 5' GCT TCC TTC 3 (i.e. SEQ ID NO. 21).

The nucleotide coding sequence may, before a modification of the invention is applied, contain one or more introns that contain nucleotides that are not encoding amino acids in the protein sequence. One of the steps in optimizing the expression of the coding sequence might be to use the synonymous coding sequence without introns. In example 2, the introns present in the native nucleotide sequence were not replaced in the modified constructs.

Alternatively, and according to another preferred embodiment of the invention, in a nucleotide sequence comprising a synonymous nucleotide coding sequence of the invention wherein the unmodified nucleotide coding sequence originally comprised one or more introns, at least one intron has been re-introduced in the nucleotide coding sequence, preferably, but not necessarily, at the original position. In example 1, the introns that are part of the *A. oryzae* pla1 DNA sequence were replaced in the codon-optimized (synonymous) DNA sequence, which was used for expression.

Translational Initiator Sequences

In a second aspect, the invention relates to translational initiator sequences. A translational initiator sequence is the nucleic acid region encoding a protein start and the biological activity of a translational initiator sequence is to initiate the ribosome-mediated production of a polypeptide whose amino acid sequence is specified by the nucleotide sequence in an mRNA. In eukaryotes, the translational initiator consensus sequence (6-12 nucleotides) before the ATG is often called Kozak consensus sequence due to the initial work on this topic (Kozak, M. (1987): an analysis of 5'-noncoding sequences from 699 vertebrate messenger RNAs. *Nucl. Acid Res.* 15(20): 8125-47). The original Kozak consensus sequence CCCGCCGCCrCC(ATG)G (SEQ ID NO: 37), including a +4 nucleotide derived by Kozak is associated with the initiation of translation in higher eukaryotes. In the context of this invention, the term "translational initiator sequence" is defined as the ten nucleotides immediately upstream of the initiator or start codon of the open reading frame of a DNA sequence coding for a polypeptide. The initiator or start codon encodes for the AA methionine. The initiator codon is typically ATG, but may also be any functional start codon such as GTG. It is well known in the art that uracil, U, replaces the deoxynucleotide thymine, T, in RNA.

The biological activity of a transcriptional initiator sequence can be determined in a quantitative way by measuring the amount of transcribed gene-product of the open reading frame immediately downstream of the transcriptional initiator sequence and comparing this amount to the amount measured from the same open reading frame controlled by a reference transcriptional initiator sequence. The amount of gene product may be determined by measuring either the amount of mRNA or the amount of polypeptide encoded by the mRNA. Examples of methods known to the skilled person to determine the amount of mRNA include, but are not limited to Northern blot, Quantitative PCR, Real Time PCR, and micro-array analyses. The amount of polypeptide encoded by the open reading frame immediately downstream of the transcriptional initiator sequence can inter alia be determined using protein measurement assays known to the skilled person. When the polypeptide encoded by the open reading frame immediately downstream of the transcriptional initiator sequence is an enzyme, the amount of polypeptide can be measured using an activity assay specific for the concerned enzyme. The skilled person will know which assay to select for a specific enzyme. A preferred assay to determine the biological activity of the transcriptional initiator sequence is an activity assay specific for a concerned enzyme.

According to a preferred embodiment, a nucleotide sequence, preferably a nucleotide sequence of the first aspect of the invention, comprises a translational initiator sequence, said translational initiator sequence comprises the nucleic acid sequence as defined by the consensus translational initiator sequence: 5'-mwChkyCAmv-3' (i.e. SEQ ID NO. 16), using ambiguity codes for nucleotides: m (A/C); r (A/G); w (MT); s (C/G); y (C/T); k (G/T); v (A/C/G); h (A/C/T); d (A/G/T); b (C/G/T); n (A/C/G/T). More preferably, the consensus translational initiator sequence is one selected from the following list: 5'-mwChkyCAAA-3' (i.e. SEQ ID NO. 17); 5'-mwChkyCACA-3' (i.e. SEQ ID NO. 18) or 5'-mwChkyCAAG-3' (i.e. SEQ ID NO. 19). These more preferred sequences correspond to any one of the following sequences (SEQ ID NOS 38-66, 22 and 67-180, respectively, in order of appearance): AACAGCCAAA; AACAGTCAAA; AACATCCAAA; AACATTCAAA; AACCGCCAAA; AACCGTCAAA; AACCTCCAAA; AACCTTCAAA; AACTGCCAAA; AACTGTCAAA; AACTTCCAAA; AACTTTCAAA; ATCAGCCAAA; ATCAGTCAAA; ATCATCCAAA; ATCATTCAAA; ATCCGCCAAA; ATCCGTCAAA; ATCCTCCAAA; ATCCTTCAAA; ATCTGCCAAA; ATCTGTCAAA; ATCTTCCAAA; ATCTTTCAAA; CACAGCCAAA; CACAGTCAAA; CACATCCAAA; CACATTCAAA; CACCGCCAAA; CACCGTCAAA; CACCTCCAAA; CACCTTCAAA; CACTGCCAAA; CACTGTCAAA; CACTTCCAAA; CACTTTCAAA; CTCAGCCAAA; CTCAGTCAAA; CTCATCCAAA; CTCATTCAAA; CTCCGCCAAA; CTCCGTCAAA; CTCCTCCAAA; CTCCTTCAAA; CTCTGCCAAA; CTCTGTCAAA; CTCTTCCAAA; CTCTTTCAAA; AACAGCCACA; AACAGTCACA; AACATCCACA; AACATTCACA; AACCGCCACA; AACCGTCACA; AACCTCCACA; AACCTTCACA; AACTGCCACA; AACTGTCACA; AACTTCCACA; AACTTTCACA; ATCAGCCACA; ATCAGTCACA; ATCATCCACA; ATCATTCACA; ATCCGCCACA; ATCCGTCACA; ATCCTCCACA; ATCCTTCACA; ATCTGCCACA; ATCTGTCACA; ATCTTCCACA; ATCTTTCACA; CACAGCCACA; CACAGTCACA; CACATCCACA; CACATTCACA; CACCGCCACA; CACCGTCACA; CAC- CTCCACA; CACCTTCACA; CACTGCCACA; CACTGT-CACA; CACTTCCACA; CACTTTCACA; CTCAGC-CACA; CTCAGTCACA; CTCATCCACA; CTCATTCACA; CTCCGCCACA; CTCCGTCACA; CTC-CTCCACA; CTCCTTCACA; CTCTGCCACA; CTCTGT-CACA; CTCTTCCACA; CTCTTTCACA; AACAGC-CAAG; AACAGTCAAG; AACATCCAAG; AACATTCAAG; AACCGCCAAG; AACCGTCAAG; AACCTCCAAG; AACCTTCAAG; AACTGCCAAG; AACTGTCAAG; AACTTCCAAG; AACTTTCAAG; ATCAGCCAAG; ATCAGTCAAG; ATCATCCAAG; ATCATTCAAG; ATCCGCCAAG; ATCCGTCAAG; ATC-CTCCAAG; ATCCTTCAAG; ATCTGCCAAG; ATCTGT-CAAG; ATCTTCCAAG; ATCTTTCAAG; CACAGC-CAAG; CACAGTCAAG; CACATCCAAG; CACATTCAAG; CACCGCCAAG; CACCGTCAAG; CAC-CTCCAAG; CACCTTCAAG; CACTGCCAAG; CACTGT-CAAG; CACTTCCAAG; CACTTTCAAG; CTCAGC-CAAG; CTCAGTCAAG; CTCATCCAAG; CTCATTCAAG; CTCCGCCAAG; CTCCGTCAAG; CTC-CTCCAAG; CTCCTTCAAG; CTCTGCCAAG; CTCTGT-CAAG; CTCTTCCAAG or CTCTTTCAAG.

According to a more preferred embodiment, the translational initiator sequence is 5'-CACCGTCAAA-3' (i.e. SEQ ID NO. 22) or 5'-CGCAGTCAAG-3' (i.e. SEQ ID NO. 23).

The present invention further encompasses isolated translational initiator sequences, variants and subsequences thereof still having the same biological activity as the isolated translational initiator sequence.

The consensus translational initiator sequence of the invention is preferably comprised in a nucleotide sequence of the first aspect of the invention. Alternatively, the consensus translational initiator sequence of the invention may be comprised in any nucleotide sequence comprising a nucleotide coding sequence encoding a compound of interest. The nucleotide coding sequence may be any coding sequence. Preferably, the nucleotide coding sequence is a synonymous coding sequence as defined previously.

Furthermore, and according to another aspect of the invention, there is provided a nucleic acid construct or expression vector as defined in the section "Nucleic acid constructs", said nucleic acid construct or expression vector comprising the consensus translational initiator sequence of the invention.

The consensus translational initiator sequence of the invention can be used in any filamentous fungal cell for expressing any nucleic acid sequence encoding any compound to be produced in said cell. Filamentous fungal cells are defined in the section "Host cells".

In the present invention, the consensus translational initiator sequence is preferably foreign to the nucleic acid sequence encoding the polypeptide to be produced, but the consensus translational initiator sequence may be native to the fungal host cell.

The skilled person will understand that the invention relates to several distinct embodiments, which can be used separately or in combination:
  a synonymous nucleotide coding sequence by using optimal codon frequency and/or modification of control sequences such as:
  a translational termination sequence orientated in 5' towards 3' direction selected from the list of sequences: TAAG, TAGA and TAAA, preferably TAAA, and/or
  a translational initiator coding sequence orientated in 5' towards 3' direction selected from the list of sequences: GCTACCCCC; GCTACCTCC; GCTACCCTC; GCTACCTTC; GCTCCCCCC; GCTCCCTCC; GCTCCCCTC; GCTCCCTTC; GCTGCCCCC; GCT-GCCTCC; GCTGCCCTC; GCTGCCTTC; GCTTC-CCCC; GCTTCCTCC; GCTTCCCTC; and GCTTC-CTTC (SEQ ID NO: 21), preferably GCT TCC TTC (SEQ ID NO: 21), and/or
a translational initiator sequence, said translational initiator sequence comprising the nucleic acid sequence as defined by the consensus translational initiator sequence: 5'-mwChkyCAmv-3' (SEQ ID NO: 16), using ambiguity codes for nucleotides: m (A/C); r (A/G); w (A/T); s (C/G); y (C/T); k (G/T); v (A/C/G); h (A/C/T); d (A/G/T); b (C/G/T); n (A/C/G/T), preferably the translational initiator sequence is one selected from the following list: 5'-mwChkyCAAA-3' (SEQ ID NO: 17), 5'-mwChkyCACA-3' (SEQ ID NO: 18), and 5'-mwChkyCAAG-3' (SEQ ID NO: 19), more preferably, the translational initiator sequence is 5'-CACCGTCAAA-3' (SEQ ID NO: 22) or 5'-CGCAGTCAAG-3' (SEQ ID NO: 23).

The skilled person will understand that the invention relates to several distinct embodiments, which can be used separately or in various distinct combinations, several of these combinations are disclosed below.

Preferably, the nucleotide sequence of the invention comprises a synonymous coding sequence, which has an optimized codon frequency according the invention as disclosed herein.

According to a more preferred embodiment, the nucleotide sequence of the invention comprises a synonymous coding sequence, which has an optimized codon frequency according the invention as disclosed herein, said synonymous coding sequence being associated with a control sequence comprising one translational termination sequence orientated in 5' towards 3' direction selected from the following list: 5'-TAAG-3', 5'-TAGA-3' and 5'-TAAA-3'. More preferably, the nucleotide sequence of the invention comprises a synonymous coding sequence, which has an optimized codon frequency according the invention as disclosed herein, said synonymous coding sequence being associated with a control sequence comprising the following translational termination sequence 5'-TAAA-3'.

According to an even more preferred embodiment, the nucleotide sequence of the invention comprises a synonymous coding sequence, which has an optimized codon frequency according the invention as disclosed herein, said synonymous coding sequence being associated with a control sequence comprising one translational initiator sequence selected from the following list: 5'-mwChkyCAAA-3' (SEQ ID NO: 17), 5'-mwChkyCACA-3' (SEQ ID NO: 18), and 5'-mwChkyCAAG-3' (SEQ ID NO: 19) (the ambiguity codes of m, w have already been earlier disclosed). More preferably, the nucleotide sequence comprises a synonymous coding sequence, which has an optimized codon frequency according the invention as disclosed herein, said synonymous coding sequence being associated with a control sequence comprising one translational initiator sequence selected from the following list: 5'-CACCGTCAAA-3' (SEQ ID NO: 22) and 5'-CGCAGTCAAG-3' (SEQ ID NO: 23). Even more preferably, the nucleotide sequence comprises a synonymous coding sequence, which has an optimized codon frequency according the invention as disclosed herein, said synonymous coding sequence being associated with the following translational initiator sequence 5'-CGCAGTCAAG-3' (SEQ ID NO: 23). Most preferably, the nucleotide sequence comprises a synonymous coding sequence, which has an optimized codon frequency according the invention as disclosed herein, said synonymous coding sequence being associated with the following translational initiator sequence 5'-CACCGTCAAA-3' (SEQ ID NO: 22).

According to a yet even more preferred embodiment, the nucleotide sequence comprises a synonymous coding sequence, which has an optimized codon frequency according the invention as disclosed herein; said synonymous coding sequence being associated with a control sequence comprising one translational initiator sequence selected from the following list: 5'-mwChkyCAAA-3' (SEQ ID NO: 17), 5'-mwChkyCACA-3' (SEQ ID NO: 18), and 5'-mwChkyCAAG-3' (SEQ ID NO: 19) (the ambiguity codes of m, w have already been earlier disclosed) and/or one translational termination sequence orientated in 5' towards 3' direction selected from the following list: 5'-TAAG-3', 5'-TAGA-3' and 5'-TAAA-3'. More preferably, the nucleotide sequence comprises a synonymous coding sequence, which has an optimized codon frequency according the invention as disclosed herein; said synonymous coding sequence being associated with a control sequence comprising one translational initiator sequence selected from the following list: 5'-mwChkyCAAA-3' (SEQ ID NO: 17) and 5'-mwChkyCACA-3' (SEQ ID NO: 18), and 5'-mwChkyCAAG-3' (SEQ ID NO: 19) (the ambiguity codes of m, w have already been earlier disclosed) and/or the following translational termination sequence 5'-TAAA-3'. Even more preferably, the nucleotide sequence comprises a synonymous coding sequence, which has an optimized codon frequency according the invention as disclosed herein; said synonymous coding sequence being associated with a control sequence comprising one translational initiator sequence selected from the following list: 5'-CACCGTCAAA-3' SEQ ID NO: 22) and 5'-CGCAGTCAAG-3' (SEQ ID NO: 23) and/or one translational termination sequence orientated in 5' towards 3' direction selected from the following list: 5'-TAAG-3', 5'-TAGA-3' and 5'-TAAA-3'. Yet even more preferably, the nucleotide sequence comprises a synonymous coding sequence, which has an optimized codon frequency according the invention as disclosed herein; said synonymous coding sequence being associated with a control sequence comprising one translational initiator sequence selected from the following list: 5'-CACCGTCAAA-3' (SEQ ID NO: 22) and 5'-CGCAGTCAAG-3' (SEQ ID NO: 23) and/or the following translational termination sequence 5'-TAAA-3'. Yet even more preferably, the nucleotide sequence comprises a synonymous coding sequence, which has an optimized codon frequency according the invention as disclosed herein; said synonymous coding sequence being associated with the following translational initiator sequence 5'-CGCAGTCAAG-3' (SEQ ID NO: 23) and/or the following translational termination sequence 5'-TAAA-3'. Most preferably, the nucleotide sequence comprises a synonymous coding sequence, which has an optimized codon frequency according the invention as disclosed herein; said synonymous coding sequence being associated with the following translational initiator sequence 5'-CACCGTCAAA-3' (SEQ ID NO: 22) and/or the following translational termination sequence 5'-TAAA-3'.

According to a most preferred embodiment, the nucleotide sequence of the invention comprises a synonymous coding sequence, which has an optimized codon frequency according the invention as disclosed herein and/or comprises the following translational initiator coding sequence 5'-GCTTCCTTC-3' (SEQ ID NO: 21); said synonymous coding sequence being associated with a control sequence comprising one translational initiator sequence selected from the following list: 5'-mwChkyCAAA-3' (SEQ ID NO: 17), 5'-mwChkyCACA-3' (SEQ ID NO: 18), and 5'-mwChkyCAAG-3' (SEQ ID NO: 19) (the ambiguity codes of m, w have already been earlier disclosed) and/or one translational termination sequence orientated in 5' towards 3' direction selected from the following list: 5'-TAAG-3', 5'-TAGA-3' and 5'-TAAA-3'. More preferably, the nucleotide sequence comprises a synonymous coding sequence, which has an optimized codon frequency according the invention as disclosed herein and/or comprises the following translational initiator coding sequence 5'-GCTTCCTTC-3' (SEQ ID NO: 21); said synonymous coding sequence being associated with a control sequence comprising one translational initiator sequence selected from the following list: 5'-mwChkyCAAA-3' (SEQ ID NO: 17) and 5'-mwChkyCACA-3' (SEQ ID NO: 18), and 5'-mwChkyCAAG-3' (SEQ ID NO: 19) (the ambiguity codes of m, w have already been earlier disclosed) and/or the following translational termination sequence 5'-TAAA-3'. Even more preferably, the nucleotide sequence comprises a synonymous coding sequence, which has an optimized codon frequency according the invention as disclosed herein and/or comprises the following translational initiator coding sequence 5'-GCTTCCTTC-3' (SEQ ID NO: 21); said synonymous coding sequence being associated with a control sequence comprising one translational initiator sequence selected from the following list: 5'-CACCGTCAAA-3' (SEQ ID NO: 22) and 5'-CGCAGTCAAG-3' (SEQ ID NO: 23) and/or one translational termination sequence orientated in 5' towards 3' direction selected from the following list: 5'-TAAG-3', 5'-TAGA-3' and 5'-TAAA-3'. Yet even more preferably, the nucleotide sequence comprises a synonymous coding sequence, which has an optimized codon frequency according the invention as disclosed herein and/or comprises the following translational initiator coding sequence 5'-GCTCCTTC-3' (SEQ ID NO: 21); said synonymous coding sequence being associated with a control sequence comprising a translational initiator sequence selected from of the following list: 5'-CACCGTCAAA-3' (SEQ ID NO: 22) and 5'-CGCAGTCAAG-3' (SEQ ID NO: 23) and/or the following translational termination sequence 5'-TAAA-3'. Yet even more preferably, the nucleotide sequence comprises a synonymous coding sequence, which has an optimized codon frequency according the invention as disclosed herein and/or comprises the following translational initiator coding sequence 5'-GCTTCCTTC-3' (SEQ ID NO: 21); said synonymous coding sequence being associated with the following translational initiator sequence 5'-CGCAGTCAAG-3' (SEQ ID NO: 23) and/or the following translational termination sequence 5'-TAAA-3'. Most preferably, the nucleotide sequence comprises a synonymous coding sequence, which has an optimized codon frequency according the invention as disclosed herein and/or comprises the following translational initiator coding sequence 5'-GCTTCCTTC-3' (SEQ ID NO: 21); said synonymous coding sequence being associated with the following translational initiator sequence 5'-CACCGTCAAA-3' (SEQ ID NO: 22) and/or the following translational termination sequence 5'-TAAA-3'.

Alternatively and according to another preferred embodiment of the invention, the nucleotide sequence of the invention comprises a coding sequence, said coding sequence being associated with a control sequence comprising one translational initiator sequence selected from the following list: 5'-mwChkyCAAA-3' (SEQ ID NO: 17), 5'-mwChkyCACA-3' (SEQ ID NO: 18), and 5'-mwChkyCAAG-3' (SEQ ID NO: 19) (the ambiguity codes of m, w have already been earlier disclosed). More preferably, the nucleotide sequence comprises a coding sequence, said coding sequence being associated with a control sequence comprising a translational initiator sequence selected from the following list: 5'-CAC- CGTCAAA-3' (SEQ ID NO: 22) and 5'-CGCAGTCAAG-3' (SEQ ID NO: 23). Even more preferably, the nucleotide sequence comprises a coding sequence, said coding sequence being associated with a control sequence comprising the translational initiator sequence 5'-CGCAGTCAAG-3'(SEQ ID NO: 23). Most preferably, the nucleotide sequence comprises a coding sequence, said coding sequence being associated with a control sequence comprising the translational initiator sequence 5'-CACCGTCAAA-3' (SEQ ID NO: 22).

Alternatively and according to another more preferred embodiment of the invention, the nucleotide sequence comprises a coding sequence and/or comprises the following translational initiator coding sequence 5'-GCTTCCTTC-3' (SEQ ID NO: 21), said coding sequence being associated with a control sequence comprising one translational initiator sequence selected from the following list: 5'-mwChkyCAAA-3' (SEQ ID NO: 17), 5'-mwChkyCACA-3' (SEQ ID NO: 18), and 5'-mwChkyCAAG-3' (SEQ ID NO: 19) (the ambiguity codes of m, w have already been earlier disclosed). More preferably, the nucleotide sequence comprises a coding sequence and/or comprises the following translational initiator coding sequence 5'-GCTTCCTTC-3' (SEQ ID NO: 21), said coding sequence being associated with a control sequence comprising one translational initiator sequence selected from the following list: 5'-CACCGTCAAA-3' (SEQ ID NO: 22) and 5'-CGCAGTCAAG-3' (SEQ ID NO: 23). Even more preferably, the nucleotide sequence comprises a coding sequence and/or comprises the following translational initiator coding sequence 5'-GCTTCCTTC-3' (SEQ ID NO: 21), said coding sequence being associated with a control sequence comprising the translational initiator sequence 5'-CGCAGTCAAG-3' (SEQ ID NO: 23). Most preferably, the nucleotide sequence comprises a coding sequence and/or comprises the following translational initiator coding sequence 5'-GCTTCCTTC-3' (SEQ ID NO: 21), said coding sequence being associated with a control sequence comprising the translational initiator sequence 5'-CACCGTCAAA-3' (SEQ ID NO: 22).

Alternatively and according to another more preferred embodiment of the invention, the nucleotide sequence comprises a coding sequence, said coding sequence being associated with a control sequence comprising a translational initiator sequence selected from the following list: 5'-mwChkyCAAA-3' (SEQ ID NO: 17), 5'-mwChkyCACA-3' (SEQ ID NO: 18), and 5'-mwChkyCAAG-3' (SEQ ID NO: 19) (the ambiguity codes of m, w have already been earlier disclosed) and/or one translational termination sequence orientated in 5' towards 3' direction selected from the following list: 5'-TAAG-3', 5'-TAGA-3' and 5'-TAAA-3'. More preferably, the nucleotide sequence comprises a coding sequence, said coding sequence being associated with a control sequence comprising a translational initiator sequence selected from the following list: 5'-mwChkyCAAA-3' (SEQ ID NO: 17), 5'-mwChkyCACA-3' (SEQ ID NO: 18), and 5'-mwChkyCAAG-3' (SEQ ID NO: 19) (the ambiguity codes of m, w have already been earlier disclosed) and/or the following translational termination sequence 5'-TAAA-3'. Even more preferably, the nucleotide sequence comprises a coding sequence, said coding sequence being associated with a control sequence comprising a translational initiator sequence selected from the following list: 5'-CACCGTCAAA-3' (SEQ ID NO: 22) and 5'-CGCAGTCAAG-3' (SEQ ID NO: 23) and/or one translational termination sequence orientated in 5' towards 3' direction selected from the following list: 5'-TAAG-3', 5'-TAGA-3' and 5'-TAAA-3'. Yet even more preferably, the nucleotide sequence comprises a coding sequence, said coding sequence being associated with a control sequence comprising a translational initiator sequence selected from the following list: 5'-CACCGTCAAA-3' (SEQ ID NO: 22) and 5'-CGCAGTCAAG-3' (SEQ ID NO: 23) and/or the following translational termination sequence 5'-TAAA-3'. Yet even more preferably, the nucleotide sequence comprises a coding sequence, said coding sequence being associated with a translational initiator sequence 5'-CGCAGTCAAG-3' (SEQ ID NO: 23) and/or one translational termination sequence orientated in 5' towards 3' direction selected from the following list: 5'-TAAG-3', 5'-TAGA-3' and 5'-TAAA-3'. Yet even more preferably, the nucleotide sequence comprises a coding sequence, said coding sequence being associated with a translational initiator sequence 5'-CGCAGTCAAG-3' (SEQ ID NO: 23) and/or the following translational termination sequence 5'-TAAA-3'. Yet even more preferably, the nucleotide sequence comprises a coding sequence, said coding sequence being associated with a translational initiator sequence 5'-CACCGTCAAA-3' (SEQ ID NO: 22) and/or one translational termination sequence orientated in 5' towards 3' direction selected from the following list: 5'-TAAG-3', 5'-TAGA-3' and 5'-TAAA-3'. Most preferably, the nucleotide sequence comprises a coding sequence, said coding sequence being associated with a translational initiator sequence 5'-CACCGTCAAA-3' (SEQ ID NO: 22) and/or the following translational termination sequence 5'-TAAA-3'.

Alternatively and according to a most preferred embodiment of the invention, the nucleotide sequence comprises a coding sequence and/or comprises the following translational initiator coding sequence 5'-GCTTCCTTC-3' (SEQ ID NO: 21), said coding sequence being associated with a control sequence comprising one translational initiator sequence selected from the following list: 5'-mwChkyCAAA-3' (SEQ ID NO: 17), 5'-mwChkyCACA-3' (SEQ ID NO: 18), and 5'-mwChkyCAAG-3' (SEQ ID NO: 19) (the ambiguity codes of m, w have already been earlier disclosed) and/or one translational termination sequence orientated in 5' towards 3' direction selected from the following list: 5'-TAAG-3', 5'-TAGA-3' and 5'-TAAA-3'. More preferably, the nucleotide sequence comprises a coding sequence and/or comprises the following translational initiator coding sequence 5'-GCTTCCTTC-3' (SEQ ID NO: 21), said coding sequence being associated with a control sequence comprising one translational initiator sequence selected from the following list: 5'-mwChkyCAAA-3' (SEQ ID NO: 17), 5'-mwChkyCACA-3' (SEQ ID NO: 18), and 5'-mwChkyCAAG-3' (SEQ ID NO: 19) (the ambiguity codes of m, w have already been earlier disclosed) and/or the following translational termination sequence 5'-TAAA-3'. Even more preferably, the nucleotide sequence comprises a coding sequence and/or comprises the following translational initiator coding sequence 5'-GCTTCCTTC-3' (SEQ ID NO: 21), said coding sequence being associated with a control sequence comprising one translational initiator sequence selected from the following list: 5'-CACCGTCAAA-3' (SEQ ID NO: 22) and 5'-CGCAGTCAAG-3' (SEQ ID NO: 23) and/or one translational termination sequence orientated in 5' towards 3' direction selected from the following list: 5'-TAAG-3', 5'-TAGA-3' and 5'-TAAA-3'. Yet even more preferably, the nucleotide sequence comprises a coding sequence and/or comprises the following translational initiator coding sequence 5'-GCTTCCTTC-3' (SEQ ID NO: 21), said coding sequence being associated with a control sequence comprising a translational initiator sequence selected from the following list: 5'-CACCGTCAAA-3' (SEQ ID NO: 22) and 5'-CGCAGTCAAG-3' SEQ ID NO: 23) and/or the following translational termination sequence 5'-TAAA-3'. Yet even more preferably, the nucleotide sequence comprises a coding sequence and/or comprises the following translational initiator coding sequence 5'-GCTTC-CTTC-3' (SEQ ID NO: 21), said coding sequence being associated with a translational initiator sequence 5'-CGCAGT-CAAG-3' (SEQ ID NO: 23) and/or one translational termination sequence orientated in 5' towards 3' direction selected from the following list: 5'-TAAG-3', 5'-TAGA-3' and 5'-TAAA-3'. Yet even more preferably, the nucleotide sequence comprises a coding sequence and/or comprises the following translational initiator coding sequence 5'-GCTTC-CTTC-3' (SEQ ID NO: 21), said coding sequence being associated with a translational initiator sequence 5'-CGCAGT-CAAG-3' (SEQ ID NO: 23) and/or the following translational termination sequence 5'-TAAA-3'. Most preferably, the nucleotide sequence comprises a coding sequence and/or comprises the following translational initiator coding sequence 5'-GCTTCCTTC-3' (SEQ ID NO: 21), said coding sequence being associated with a translational initiator sequence 5'-CACCGTCAAA-3' (SEQ ID NO: 22) and/or the following translational termination sequence 5'-TAAA-3'.

Alternatively and according to another preferred embodiment of the invention, the nucleotide sequence of the invention comprises a coding sequence, said coding sequence being associated with a control sequence comprising one translational termination sequence orientated in 5' towards 3' direction selected from the following list: 5'-TAAG-3', 5'-TAGA-3' and 5'-TAAA-3'. More preferably, the nucleotide sequence of the invention comprises a coding sequence, said coding sequence being associated with the following translational termination sequence 5'-TAAA-3'.

Alternatively and according to another preferred embodiment of the invention, the nucleotide sequence of the invention comprises a coding sequence and/or comprises the following translational initiator coding sequence 5'-GCTTCCTTC-3' (SEQ ID NO: 21), said coding sequence being associated with a control sequence comprising one translational termination sequence orientated in 5' towards 3' direction selected from the following list: 5'-TAAG-3', 5'-TAGA-3' and 5'-TAAA-3'. More preferably, the nucleotide sequence comprises a coding sequence and/or comprises the following translational initiator coding sequence 5'-GCTTC-CTTC-3' (SEQ ID NO: 21), said coding sequence being associated with the following translational termination sequence 5'-TAAA-3'.

In addition to the control sequences defined in the first aspect of the invention, other control sequences may be used. Such other control sequence may be an appropriate promoter sequence, a nucleotide sequence, which is recognized by a host cell for expression of the nucleic acid sequence. The promoter sequence contains transcriptional control sequences, which mediate the expression of the polypeptide. The promoter may be any nucleic acid sequence, which shows transcriptional activity in the cell including mutant, truncated, and hybrid promoters, and may be obtained from genes encoding extracellular or intracellular polypeptides either homologous or heterologous to the cell.

The control sequence may also be a suitable transcription terminator sequence, a sequence recognized by a cell to terminate transcription. The terminator sequence is operably linked to the 3' terminus of the nucleic acid sequence encoding the polypeptide. Any terminator, which is functional in the cell, may be used in the present invention.

Preferred terminators for filamentous fungal cells are obtained from the genes encoding *A. oryzae* TAKA amylase, *A. niger* glucoamylase (glaA), *A. nidulans* anthranilate synthase, *A. niger* alpha-glucosidase, trpC gene and *Fusarium oxysporum* trypsin-like protease.

The control sequence may also be a suitable leader sequence, a non-translated region of a mRNA which is important for translation by the cell. The leader sequence is operably linked to the 5' terminus of the nucleic acid sequence encoding the polypeptide. Any leader sequence, which is functional in the cell, may be used in the present invention.

Preferred leaders for filamentous fungal cells are obtained from the genes encoding *A. oryzae* TAKA amylase and *A. nidulans* triose phosphate isomerase and *A. niger* glaA.

Other control sequences may be isolated from the *Penicillium* IPNS gene, or pcbC gene, the beta tubulin gene. All the control sequences cited in WO 01/21779 are herewith incorporated by reference.

The control sequence may also be a polyadenylation sequence, a sequence which is operably linked to the 3' terminus of the nucleic acid sequence and which, when transcribed, is recognized by the cell as a signal to add polyadenosine residues to transcribed mRNA. Any polyadenylation sequence, which is functional in the cell, may be used in the present invention.

Preferred polyadenylation sequences for filamentous fungal cells are obtained from the genes encoding *A. oryzae* TAKA amylase, *A. niger* glucoamylase, *A. nidulans* anthranilate synthase, *Fusarium oxyporum* trypsin-like protease and *A. niger* alpha-glucosidase.

The nucleotide sequence of the invention may be comprised in a nucleic acid construct or expression vector.

Nucleic Acid Constructs

According to a third aspect, the invention relates to a nucleic acid construct or expression vector comprising at least one the nucleotide sequences defined in the former sections:

a synonymous nucleotide coding sequence by using optimal codon frequency and optionally modification of control sequences such as:

one translational termination sequence orientated in 5' towards 3' direction selected from the following list of sequences: TAAG, TAGA and TAAA, preferably TAAA, and/or one translational initiator coding sequence orientated in 5' towards 3' direction selected from the following list of sequences: GCTACCCCC; GCTACCTCC; GCTAC-CCTC; GCTACCTTC; GCTCCCCCC; GCTCCCTCC; GCTCCCCTC; GCTCCCTTC; GCTGCCCCC; GCT-GCCTCC; GCTGCCCTC; GCTGCCTTC; GCTTC-CCCC; GCTTCCTCC; GCTTCCCTC; and GCTTC-CTTC (SEQ ID NO: 21), preferably GCT TCC TTC (SEQ ID NO: 21), and/or a translational initiator sequence, said translational initiator sequence comprising the nucleic acid sequence as defined by the consensus translational initiator sequence: 5'-mwChkyCAmv-3' (SEQ ID NO: 16), using ambiguity codes for nucleotides: m (A/C); r (A/G); w (A/T); s (C/G); y (C/T); k (G/T); v (A/C/G); h (A/C/T); d (A/G/T); b (C/G/T); n (A/C/G/T), preferably the translational initiator sequence is one selected from the following list: 5'-mwChkyCAAA-3' (SEQ ID NO: 17), 5'-mwChkyCACA-3' (SEQ ID NO: 18), and 5'-mwCh-kyCAAG-3' (SEQ ID NO: 19). These preferred sequences correspond to any one of the following sequences (SEQ ID NOS 38-66, 22 and 67-180, respectively, in order of appearance): AACAGCCAAA; AACAGTCAAA; AACATCCAAA; AACATTCAAA; AACCGCCAAA; AACCGTCAAA; AACCTCCAAA; AACCTTCAAA; AACTGCCAAA; AACTGTCAAA; AACTTCAAA; AACTTTCAAA; ATCAGCCAAA; ATCAGTCAAA; ATCATCCAAA; ATCATTCAAA;

ATCCGCCAAA; ATCCGTCAAA; ATCCTCCAAA; ATCCTTCAAA; ATCTGCCAAA; ATCTGTCAAA; ATCTTCCAAA; ATCTTTCAAA; CACAGCCAAA; CACAGTCAAA; CACATCCAAA; CACATTCAAA; CACCGCCAAA; CACCGTCAAA; CACCTCCAAA; CACCTTCAAA; CACTGCCAAA; CACTGTCAAA; CACTTCCAAA; CACTTTCAAA; CTCAGCCAAA; CTCAGTCAAA; CTCATCCAAA; CTCATTCAAA; CTCCGCCAAA; CTCCGTCAAA; CTCCTCCAAA; CTCCTTCAAA; CTCTGCCAAA; CTCTGTCAAA; CTCTTCCAAA; CTCTTTCAAA; AACAGCCACA; AACAGTCACA; AACATCCACA; AACATTCACA; AACCGCCACA; AACCGTCACA; AACCTCCACA; AACCTTCACA; AACTGCCACA; AACTGTCACA; AACTTCCACA; AACTTTCACA; ATCAGCCACA; ATCAGTCACA; ATCATCCACA; ATCATTCACA; ATCCGCCACA; ATCCGTCACA; ATCCTCCACA; ATCCTTCACA; ATCTGCCACA; ATCTGTCACA; ATCTTCCACA; ATCTTTCACA; CACAGCCACA; CACAGTCACA; CACATCCACA; CACATTCACA; CACCGCCACA; CACCGTCACA; CACCTCCACA; CACCTTCACA; CACTGCCACA; CACTGTCACA; CACTTCCACA; CACTTTCACA; CTCAGCCACA; CTCAGTCACA; CTCATCCACA; CTCATTCACA; CTCCGCCACA; CTCCGTCACA; CTCCTCCACA; CTCCTTCACA; CTCTGCCACA; CTCTGTCACA; CTCTTCCACA; CTCTTTCACA; AACAGCCAAG; AACAGTCAAG; AACATCCAAG; AACATTCAAG; AACCGCCAAG; AACCGTCAAG; AACCTCCAAG; AACCTTCAAG; AACTGCCAAG; AACTGTCAAG; AACTTCCAAG; AACTTTCAAG; ATCAGCCAAG; ATCAGTCAAG; ATCATCCAAG; ATCATTCAAG; ATCCGCCAAG; ATCCGTCAAG; ATCCTCCAAG; ATCCTTCAAG; ATCTGCCAAG; ATCTGTCAAG; ATCTTCCAAG; ATCTTTCAAG; CACAGCCAAG; CACAGTCAAG; CACATCCAAG; CACATTCAAG; CACCGCCAAG; CACCGTCAAG; CACCTCCAAG; CACCTTCAAG; CACTGCCAAG; CACTGTCAAG; CACTTCCAAG; CACTTTCAAG; CTCAGCCAAG; CTCAGTCAAG; CTCATCCAAG; CTCATTCAAG; CTCCGCCAAG; CTCCGTCAAG; CTCCTCCAAG; CTCCTTCAAG; CTCTGCCAAG; CTCTGTCAAG; CTCTTCCAAG or CTCTTTCAAG. More preferably, the translational initiator sequence is 5'-CACCGTCAAA-3' (SEQ ID NO: 22) or 5'-CGCAGTCAAG-3' (SEQ ID NO: 23).

According to another preferred embodiment, the nucleic acid construct or expression vector comprises a translational initiator sequence, said translational initiator sequence comprising the nucleic acid sequence as defined by the consensus translational initiator sequence: 5'-mwChkyCAmv-3' (SEQ ID NO: 16), using ambiguity codes for nucleotides: m (A/C); r (A/G); w (A/T); s (C/G); y (C/T); k (G/T); v (A/C/G); h (A/C/T); d (A/G/T); b (C/G/T); n (A/C/G/T), preferably the translational initiator sequence is selected amongst the group consisting of: 5'-mwChkyCAAA-3' (SEQ ID NO: 17), 5'mwChkyCACA-3' (SEQ ID NO: 18), and 5'-mwChkyCAAG-3' (SEQ ID NO: 19). These preferred sequences correspond to any one of the following sequences (SEQ ID NOS 38-66, 22 and 67-180, respectively, in order of appearance): AACAGCCAAA; AACAGTCAAA; AACATCCAAA; AACATTCAAA; AACCGCCAAA; AACCGTCAAA; AACCTCCAAA; AACCTTCAAA; AACTGCCAAA; AACTGTCAAA; AACTTCCAAA; AACTTTCAAA; ATCAGCCAAA; ATCAGTCAAA; ATCATCCAAA; ATCATTCAAA; ATCCGCCAAA; ATCCGTCAAA; ATCCTCCAAA; ATCCTTCAAA; ATCTGCCAAA; ATCTGTCAAA; ATCTTCCAAA; ATCTTTCAAA; CACAGCCAAA; CACAGTCAAA; CACATCCAAA; CACATTCAAA; CACCGCCAAA; CACCGTCAAA; CACCTCCAAA; CACCTTCAAA; CACTGCCAAA; CACTGTCAAA; CACTTCCAAA; CACTTTCAAA; CTCAGCCAAA; CTCAGTCAAA; CTCATCCAAA; CTCATTCAAA; CTCCGCCAAA; CTCCGTCAAA; CTCCTCCAAA; CTCCTTCAAA; CTCTGCCAAA; CTCTGTCAAA; CTCTTCCAAA; CTCTTTCAAA; AACAGCCACA; AACAGTCACA; AACATCCACA; AACATTCACA; AACCGCCACA; AACCGTCACA; AACCTCCACA; AACCTTCACA; AACTGCCACA; AACTGTCACA; AACTTCCACA; AACTTTCACA; ATCAGCCACA; ATCAGTCACA; ATCATCCACA; ATCATTCACA; ATCCGCCACA; ATCCGTCACA; ATCCTCCACA; ATCCTTCACA; ATCTGCCACA; ATCTGTCACA; ATCTTCCACA; ATCTTTCACA; CACAGCCACA; CACAGTCACA; CACATCCACA; CACATTCACA; CACCGCCACA; CACCGTCACA; CACCTCCACA; CACCTTCACA; CACTGCCACA; CACTGTCACA; CACTTCCACA; CACTTTCACA; CTCAGCCACA; CTCAGTCACA; CTCATCCACA; CTCATTCACA; CTCCGCCACA; CTCCGTCACA; CTCCTCCACA; CTCCTTCACA; CTCTGCCACA; CTCTGTCACA; CTCTTCCACA; CTCTTTCACA; AACAGCCAAG; AACAGTCAAG; AACATCCAAG; AACATTCAAG; AACCGCCAAG; AACCGTCAAG; AACCTCCAAG; AACCTTCAAG; AACTGCCAAG; AACTGTCAAG; AACTTCCAAG; AACTTTCAAG; ATCAGCCAAG; ATCAGTCAAG; ATCATCCAAG; ATCATTCAAG; ATCCGCCAAG; ATCCGTCAAG; ATCCTCCAAG; ATCCTTCAAG; ATCTGCCAAG; ATCTGTCAAG; ATCTTCCAAG; ATCTTTCAAG; CACAGCCAAG; CACAGTCAAG; CACATCCAAG; CACATTCAAG; CACCGCCAAG; CACCGTCAAG; CACCTCCAAG; CACCTTCAAG; CACTGCCAAG; CACTGTCAAG; CACTTCCAAG; CACTTTCAAG; CTCAGCCAAG; CTCAGTCAAG; CTCATCCAAG; CTCATTCAAG; CTCCGCCAAG; CTCCGTCAAG; CTCCTCCAAG; CTCCTTCAAG; CTCTGCCAAG; CTCTGTCAAG; CTCTTCCAAG or CTCTTTCAAG. More preferably, the translational initiator sequence is 5'-CACCGTCAAA-3' (SEQ ID NO: 22) or 5'-CGCAGTCAAG-3' (SEQ ID NO: 23).

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette or expression vector when the nucleic acid construct contains all the control sequences required for expression of a coding sequence.

Manipulation of the nucleotide sequence encoding a polypeptide prior to its insertion into a nucleic acid construct or expression vector may be desirable or necessary depending on the nucleic acid construct or expression vector. The techniques for modifying nucleic acid sequences utilizing cloning methods are well known in the art.

The present invention also relates to recombinant expression vectors comprising the nucleotide sequences of the invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites.

Alternatively, the nucleotide sequence encoding the polypeptide may be expressed by inserting the nucleotide sequence or nucleic acid construct comprising the sequence into an appropriate vector for expression. In creating the expression vector, the coding sequence is located in the vector in such a fashion that the coding sequence is operatively associated with the appropriate control sequences for expression, and optional secretion.

The recombinant expression vector may be any vector (e.g., a plasmid or virus), which can be conveniently subjected to recombinant DNA procedures and can confer expression of the nucleic acid sequence encoding the polypeptide. The choice of the vector will typically depend on the compatibility of the vector with the filamentous fungal cell into which the vector is to be introduced. The vectors may be linear or closed circular plasmids. The vector may be an autonomously replicating vector, i.e., a vector, which exists as an extrachromosomal entity, the replication of which is independent of chromosomal replication, e.g., a plasmid, an extrachromosomal element, a minichromosome, or an artificial chromosome. An autonomously maintained cloning vector may comprise the AMA1-sequence (see e.g. Aleksenko and Clutterbuck (1997), Fungal Genet. Biol. 21: 373-397).

Alternatively, the vector may be one which, when introduced into the fungal cell, is integrated into the genome and replicated together with the chromosome (s) into which it has been integrated. The integrative cloning vector may integrate at random or at a predetermined target locus in the chromosomes of the fungal host cell. In a preferred embodiment of the invention, the integrative cloning vector comprises a DNA fragment, which is homologous to a DNA sequence in a predetermined target locus in the genome of the fungal host cell for targeting the integration of the cloning vector to this predetermined locus. In order to promote targeted integration, the cloning vector is preferably linearized prior to transformation of the host cell. Linearization is preferably performed such that at least one but preferably either end of the cloning vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb. Preferably, the DNA sequence in the cloning vector, which is homologous to the target locus is derived from a highly expressed locus meaning that it is derived from a gene, which is capable of high expression level in the filamentous fungal host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l (as described in EP 357 127 B1). A number of preferred highly expressed fungal genes are given by way of example: the amylase, glucoamylase, alcohol dehydrogenase, xylanase, glyceraldehyde-phosphate dehydrogenase or cellobiohydrolase (cbh) genes from *Aspergilli* or *Trichoderma*. Most preferred highly expressed genes for these purposes are a glucoamylase gene, preferably an *A. niger* glucoamylase gene, an *A. oryzae* TAKA-amylase gene, an *A. nidulans* gpdA gene, a *Trichoderma reesei* cbh gene, preferably cbh1. More than one copy of a nucleic acid sequence encoding a polypeptide may be inserted into the host cell to increase production of the gene product. This can be done, preferably by integrating into its genome copies of the DNA sequence, more preferably by targeting the integration of the DNA sequence at one of the highly expressed locus defined in the former paragraph. Alternatively, this can be done by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent. To increase even more the number of copies of the DNA sequence to be over expressed the technique of gene conversion as described in WO98/46772 may be used.

The vector system may be a single vector or plasmid or two or more vectors or plasmids, which together contain the total DNA to be introduced into the genome of the filamentous fungal cell, or a transposon.

The vectors preferably contain one or more selectable markers, which permit easy selection of transformed cells. A selectable marker is a gene the product of which provides for biocide or viral resistance, resistance to heavy metals, prototrophy to auxotrophs, and the like. A selectable marker for use in a filamentous fungal cell may be selected from the group including, but not limited to, amdS (acetamidase), argB (ornithine carbamoyltransferase), bar (phosphinothricinacetyltransferase), bleA (phleomycin binding), hygB (hygromycinphosphotransferase), niaD (nitrate reductase), pyrG (orotidine-5'-phosphate decarboxylase), sC (sulfate adenyltransferase), and trpC (anthranilate synthase), as well as equivalents from other species. Preferred for use in an *Aspergillus* and *Penicillium* cell are the amdS (EP 635574 B1, WO 97/06261) and pyrG genes of *A. nidulans* or *A. oryzae* and the bar gene of *Streptomyces hygroscopicus*. More preferably an amdS gene is used, even more preferably an amdS gene from *A. nidulans* or *A. niger*. A most preferred selection marker gene is the *A. nidulans* amdS coding sequence fused to the *A. nidulans* gpdA promoter (see EP 635574 B1). AmdS genes from other filamentous fungi may also be used (WO 97/06261).

The procedures used to ligate the elements described above to construct the recombinant expression vectors of the present invention are well known to one skilled in the art (see, e.g., Sambrook et al., 1989, supra).

Host Cells

According to a fourth aspect, the invention relates to a filamentous fungal host cell. The filamentous fungal host cell of the invention may be any filamentous fungal host cell host cell known to the skilled person.

"Filamentous fungi" include all filamentous forms of the subdivision Eumycota and Oomycota (as defined by Hawksworth et al., 1995, supra). The filamentous fungi are characterized by a mycelia wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Aspergillus, Aureobasidium, Cryptococcus, Chrysosporum Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, and *Trichoderma* Strains of *Aspergillus* and teleomorphs thereof are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL) *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* ATCC44006 and derivatives thereof.

Preferably, the filamentous fungal host cell of the invention comprises at least one copy of the nucleic acid construct of the third aspect of the invention.

According to a preferred embodiment, the coding and/or control sequences present in the nucleic acid construct are native to the filamentous fungal host cell before modification of the coding and/or control sequences according to the first and second aspect of the invention.

According to another preferred embodiment, the coding and/or control sequences present in the nucleic acid construct are heterologous to the filamentous fungal host cell before modification of the coding and/or control sequences according to the first and second aspect of the invention.

According to a more preferred embodiment, the filamentous fungal host cell of the invention, comprising a given copy number of the nucleic acid construct of the third aspect of the invention is a filamentous fungal cell, wherein the expression of the product encoded by said nucleic acid construct is enhanced as compared to the production of the same product encoded by the corresponding nucleic acid construct comprising the corresponding native nucleotide sequences, said corresponding nucleic acid construct being present in the same copy number in the corresponding filamentous fungal host cell. Preferably, the modification of the nucleotide sequences present in the nucleic acid construct or expression vector of the third aspect of the invention results in an increase by at least 1%, 5%, 10%, 25%, 50%, 100%, 200%, 300%, 400% more preferably at least 500% of the yield of the compound of interest produced by the filamentous fungal host cell of the invention comprising a given copy number of the nucleic acid construct of the third aspect of the invention, as compared to the production of the corresponding nucleic acid construct comprising the corresponding native nucleotide sequences, said corresponding nucleic acid construct being present in the same copy number in the corresponding filamentous fungal host cell.

The increase in yield of the compound of interest to be produced may be determined by measuring the amount of compound produced by the filamentous fungal host cell of the invention and comparing it to the compound of interest produced by the corresponding filamentous fungal host cell. Determining the yield of compound of interest produced may be performed by measuring inter alia the amount of mRNA transcribed from the (synonymous) nucleotide coding sequence, the amount of polypeptide encoded by the mRNA, or the amount of compound (e.g. metabolite) in which' production the polypeptide encoded by the synonymous nucleotide coding sequence is involved with. Examples of methods known to the skilled person to determine the amount of mRNA include, but are not limited to Northern blot, Quantitative PCR, Real Time PCR, and micro-array analyses. The amount of polypeptide can inter alia be determined using protein measurement assays known to the skilled person. When the polypeptide is an enzyme, the amount of polypeptide can be measured using an activity assay specific for the concerned enzyme. The skilled person will know which assay to select for a specific enzyme. A preferred assay to determine the yield of the compound of interest to be produced is an activity assay specific for the concerned enzyme.

According to a more preferred embodiment, the host cell of the present invention is a cell belonging to a species selected from the group consisting of an *Aspergillus*, *Penicillium*, *Fusarium*, *Chrysosporum* or *Trichoderma* species, most preferably a species selected from the group consisting of *Aspergillus niger*, *Aspergillus oryzae*, *Aspergillus sojae*, *Aspergillus terreus*, *Chrysosporum lucknowense*, *Trichoderma reesei* or *Penicillium chrysogenum*. A most preferred *Aspergillus niger* host cell is CBS513.88 or derivatives thereof.

The host cell may be a wild type filamentous fungus host cell or a variant, a mutant or a genetically modified filamentous fungus host cell. In a preferred embodiment of the invention the host cell is a protease deficient or protease minus strain. This may be the protease deficient strain *Aspergillus oryzae* JaL 125 having the alkaline protease gene named "alp" deleted (described in WO 97/35956 or EP 429 490), or the tripeptidyl-aminopeptidases (TPAP) deficient strain of *A. niger*, disclosed in WO 96/14404. Further, also host cell with reduced production of the transcriptional activator (prtT) as described in WO 01/68864 is contemplated according to the invention. Another specifically contemplated host strain is the *Aspergillus oryzae* BECh2, where the three TAKA amylase genes present in the parent strain IF04177 has been inactivated. In addition, two proteases, the alkaline protease and neutral metalloprotease 11 have been destroyed by gene disruption. The ability to form the metabolites cyclopiazonic acid and kojic acid has been destroyed by mutation. BECh2 is described in WO 00/39322 and is derived from JaL228 (described in WO 98/12300), which again was a mutant of IF04177 disclosed in U.S. Pat. No. 5,766,912 as A1560.

Optionally, the filamentous fungal host cell comprises an elevated unfolded protein response (UPR) compared to the wild type cell to enhance production abilities of a polypeptide of interest. UPR may be increased by techniques described in US2004/0186070A1 and/or US2001/0034045A1 and/or WO01/72783A2 and/or WO2005/123763. More specifically, the protein level of HAC1 and/or IRE1 and/or PTC2 has been modulated, and/or the SEC61 protein has been engineered in order to obtain a host cell having an elevated UPR.

Alternatively, or in combination with an elevated UPR, the host cell is genetically modified to obtain a phenotype displaying lower protease expression and/or protease secretion compared to the wild-type cell in order to enhance production abilities of a polypeptide of interest. Such phenotype may be obtained by deletion and/or modification and/or inactivation of a transcriptional regulator of expression of proteases. Such a transcriptional regulator is e.g. prtT. Lowering expression of proteases by modulation of prtT may be performed by techniques described in US2004/0191864A1.

Alternatively, or in combination with an elevated UPR and/or a phenotype displaying lower protease expression and/or protease secretion, the host cell displays an oxalate deficient phenotype in order to enhance the yield of production of a polypeptide of interest. An oxalate deficient phenotype may be obtained by techniques described in WO2004/070022A2.

Alternatively, or in combination with an elevated UPR and/or a phenotype displaying lower protease expression and/or protease secretion and/or oxalate deficiency, the host cell displays a combination of phenotypic differences compared to the wild cell to enhance the yield of production of the polypeptide of interest. These differences may include, but are not limited to, lowered expression of glucoamylase and/or neutral alpha-amylase A and/or neutral alpha-amylase B, alpha-1, 6transglucosidase, protease, and oxalic acid hydrolase. Said phenotypic differences displayed by the host cell may be obtained by genetic modification according to the techniques described in US2004/0191864A1.

Alternatively, or in combination with phenotypes described here above, the efficiency of targeted integration of a nucleic acid construct into the genome of the host cell by homologous recombination, i.e. integration in a predetermined target locus, is preferably increased by augmented homologous recombination abilities of the host cell. Such phenotype of the cell preferably involves a deficient hdfA or hdfB gene as described in WO2005/095624. WO2005/095624 discloses a preferred method to obtain a filamentous fungal cell comprising increased efficiency of targeted integration.

The introduction of an expression vector or a nucleic acid construct into a filamentous fungal cell may involve a process consisting of protoplast formation, transformation of the protoplasts, and regeneration of the cell wall in a manner known per se. Suitable procedures for transformation of Aspergillus cells are described in EP 238 023 and Yelton et al., 1984, Proceedings of the National Academy of Sciences USA 81:1470-1474. A suitable method of transforming Fusarium species is described by Malardier et al., 1989, Gene 78:147156 or in WO 96/00787. The expression vector or nucleic acid construct that can be used were already described under the corresponding sections.

Producing a Compound of Interest

The present invention may be used to produce a compound of interest. The compound of interest is preferably a polypeptide. Alternatively, the compound of interest may be a metabolite. In this case, a nucleotide sequence encoding an enzyme involved in the synthesis of the metabolite is modified according to the invention. The term "metabolite" encompasses both primary and secondary metabolites; the metabolite may be any metabolite. A preferred metabolite is citric acid. Another preferred metabolite is a carotenoid. The metabolite may be encoded by one or more genes, such as in a biosynthetic or metabolic pathway. Primary metabolites are products of primary or general metabolism of a cell, which are concerned with energy metabolism, growth, and structure. Secondary metabolites are products of secondary metabolism (see, for example, R. B. Herbert, The Biosynthesis of Secondary Metabolites, Chapman and Hall, New York, 1981). The primary metabolite may be, but is not limited to, an amino acid, fatty acid, nucleoside, nucleotide, sugar, triglyceride, or vitamin. The secondary metabolite may be, but is not limited to, an alkaloid, coumarin, flavonoid, polyketide, quinine, steroid, peptide, or terpene. The secondary metabolite may be an antibiotic, antifeedant, attractant, bacteriocide, fungicide, hormone, insecticide, or rodenticide. Preferred antibiotics are cephalosporins and beta-lactams.

Alternatively, the compound of interest may also be the product of a selectable marker gene. A selectable marker gene is a gene the product of which provides for biocide or viral resistance, resistance to heavy metals, prototrophy to auxotrophs, and the like. In this case, a nucleotide sequence encoding a selectable marker gene product is modified according to the invention. Selectable markers include, but are not limited to, amdS (acetamidase), argB (ornithinecarbamoyltransferase), bar (phosphinothricinacetyltransferase), hygB (hygromycin phosphotransferase), niaD (nitratereductase), pyrG (orotidine-5'-phosphate decarboxylase), sC (sulfate adenyltransferase), trpC (anthranilate synthase), ble (phleomycin resistance protein), as well as equivalents thereof.

When the compound of interest is a polypeptide, the polypeptide may be any polypeptide whether native or heterologous (or not native) to the cell. As soon as the DNA sequence encoding the polypeptide and the control DNA sequences operatively associated thereto are known, these native or not native DNA sequences are modified according to the invention (see section DNA sequence), cloned into an appropriate DNA construct or expression vector and transformed into a chosen host. The nucleic acid sequence encoding a heterologous polypeptide may be obtained from any prokaryotic, eukaryotic, plant, or other source. For purposes of the present invention, the term "obtained from" as used herein in connection with a given source shall mean that the polypeptide is produced by the source or by a cell in which a gene from the source has been inserted.

The term "heterologous polypeptide" is defined herein as a polypeptide, which is not produced by a wild-type cell (not native). The term "polypeptide" is not meant herein to refer to a specific length of the encoded produce and therefore encompasses peptides, oligopeptides and proteins. The polypeptide may also be a recombinant polypeptide, which is a polypeptide native to a cell, which is encoded by an optimized nucleic acid sequence for example and, which additionally may comprise one or more control sequences, foreign to the nucleic acid sequence, which is involved in the production of the polypeptide. The polypeptide may be a wild-type polypeptide or a variant thereof. The polypeptide may also be a hybrid polypeptide, which contains a combination of partial or complete polypeptide sequences obtained from at least two different polypeptides where one or more of the polypeptides may be heterologous to the cell. Polypeptides further include naturally occurring allelic and engineered variations of the above-mentioned polypeptides.

Preferably, the polypeptide is secreted outside the filamentous fungal host cell. In a preferred embodiment, the polypeptide is an antibody or portions thereof, an antigen, a clotting factor, an enzyme, a hormone or a hormone variant, a receptor or portions thereof, a regulatory protein, a structural protein, a reporter, or a transport protein, intracellular protein, protein involved in secretion process, protein involved in folding process, chaperone, peptide amino acid transporter, glycosylation factor, transcription factor. In a preferred embodiment, the polypeptide is secreted into the extracellular environment.

In a more preferred embodiment, the enzyme is an oxidoreductase, transferase, hydrolase, lyase, isomerase, ligase, catalase, cellulase, chitinase, cutinase, deoxyribonuclease, dextranase, esterase.

In an even more preferred embodiment, the polypeptide is a carbohydrase, e.g., cellulases such as endoglucanases, β-glucanases, cellobiohydrolases or β-glucosidases, hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, proteolytic enzymes, oxidoreductases such as oxidases, transferases, or isomerases. More preferably, the desired gene encodes a phytase. In an even more preferred embodiment, the polypeptide is an aminopeptidase, amylase, carbohydrase, carboxypeptidase, endo-protease, metalloprotease, serine-protease catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, proteolytic enzyme, invertase, laccase, lipase, mannosidase, mutanase, oxidase, pectinolytic enzyme, peroxidase, phospholipase, polyphenoloxidase, ribonuclease, transglutaminase, or glucose oxidase, hexose oxidase, monooxygenase.

In another even more preferred embodiment, the polypeptide is human insulin or an analog thereof, human growth hormone, erythropoietin, tissue plasminogen activator (tPA) or insulinotropin.

The polypeptide may also be an intracellular protein or enzyme such as for example a chaperone, protease or transcription factor. An example of this is described in Appl. Microbiol. Biotechnol. 1998 October; 50(4):447-54 ("Analysis of the role of the gene bipA, encoding the major endoplasmic reticulum chaperone protein in the secretion of homologous and heterologous proteins in black *Aspergilli*. Punt P J, van Gemeren I A, Drint-Kuijvenhoven J, Hessing J G, van Muijlwijk-Harteveld G M, Beijersbergen A, Verrips C T, van den Hondel C A). This can be used for example to improve the efficiency of a host cell as protein producer if this polypeptide, such as a chaperone, protease or transcription factor, was known to be a limiting factor in protein production.

Alternatively, the intracellular polypeptide is an enzyme involved in the production of a given secondary metabolite such as a carotenoid or an antibiotica.

The present invention may also be used for the recombinant production of polypeptides, which are native to the cell. The native polypeptide may be recombinantly produced if one modifies the coding and/or control nucleotide sequences as defined in the corresponding earlier sections. For example, the coding sequence is modified by using the optimized codons frequency as defined earlier to code any amino acid to improve the expression level of the native or naturally occurring nucleotide sequence. Optionally, the synonymous coding sequence obtained may be placed under the control of a different promoter to enhance expression of the polypeptide, to expedite export of a native polypeptide of interest outside the cell by use of a signal sequence of the invention, and to increase the copy number of a gene encoding the polypeptide normally produced by the cell. The present invention also encompasses, within the scope of the term "heterologous polypeptide", such recombinant production of polypeptides native to the cell, to the extent that such expression involves the use of genetic elements not native to the cell, or use of native elements which have been manipulated to function in a manner that do not normally occur in the filamentous fungal cell. The techniques used to isolate or clone a nucleic acid sequence encoding a heterologous polypeptide are known in the art and include isolation from genomic DNA, preparation from cDNA, or a combination thereof.

In the methods of the present invention, heterologous polypeptides may also include a fused or hybrid polypeptide in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the mutant fungal cell. An isolated nucleic acid sequence encoding a heterologous polypeptide of interest may be manipulated in a variety of ways to provide for expression of the polypeptide. Expression will be understood to include any step involved in the production of the polypeptide including, but not limited to, transcription, posttranscriptional modification, translation, post-translational modification, and secretion. Manipulation of the nucleic acid sequence encoding a polypeptide prior to its insertion into a vector may be desirable or necessary depending on the expression vector. The techniques for modifying nucleic acid sequences utilizing cloning methods are well known in the art.

The compound of interest described in the section here above may be produced in a filamentous fungal host cells provided by the invention.

Thus, according to another aspect, the invention relates to methods of producing a compound of interest in a filamentous fungal host cell of the present invention, comprising:

(a) cultivating the filamentous fungal host cell as defined in the former section in a nutrient medium suitable for production of the compound of interest; and (b) recovering the compound of interest from the nutrient medium of the filamentous fungal host cell.

The filamentous fungal host cells of the present invention are cultivated in a nutrient medium suitable for production of the compound of interest using methods known in the art. For example, the cells may be cultivated by shake flask cultivation, small-scale or large-scale fermentation (including continuous, batch, fed-batch, or solid state fermentations) in laboratory or industrial fermentors performed in a suitable medium and under conditions allowing the compound of interest to be expressed and/or isolated. The cultivation takes place in a suitable nutrient medium comprising carbon and nitrogen sources and inorganic salts, using procedures known in the art (see, e.g., Bennett, J. W. and LaSure, L., eds., More Gene Manipulations in Fungi, Academic Press, CA, 1991). Suitable media are available from commercial suppliers or may be prepared using published compositions (e.g., in catalogues of the American Type Culture Collection). If the compound of interest is secreted into the nutrient medium, the polypeptide can be recovered directly from the medium. If the compound of interest is not secreted, it is recovered from cell lysates.

The resulting compound of interest may be isolated by methods known in the art. For example, the polypeptide may be isolated from the nutrient medium by conventional procedures including, but not limited to, centrifugation, filtration, extraction, spray drying, evaporation, or precipitation. The isolated compound of interest may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing, differential solubility (e.g., ammonium sulfate precipitation), or extraction (see, e.g., Protein Purification, J.-C. Janson and Lars Ryden, editors, VCH Publishers, New York, 1989).

The compound of interest may be detected using methods known in the art that are specific for the polypeptide. These detection methods may include use of specific antibodies, formation of an enzyme product, disappearance of an enzyme substrate, or SDS PAGE. For example, an enzyme assay may be used to determine the activity if the compound of interest is an enzyme. Procedures for determining enzyme activity are known in the art for many enzymes.

In the method of the invention, the yield of the compound of interest produced by the filamentous fungal host of the invention comprising a given copy number of the nucleic acid construct of the third aspect of the invention is preferably increased by at least 1%, 5%, 10%, 25%, 50%, 100%, 200%, 300%, 400% more preferably at least 500%, as compared to the production of the corresponding nucleic acid construct comprising the corresponding native nucleotide sequences, said corresponding nucleic acid construct being present in the same copy number in the corresponding filamentous fungal host cell. Preferably, the filamentous fungal host cell of the present invention is an *Aspergillus, Trichoderma, Fusarium, Chrysosporum* or *Penicillium* host cell. More preferably the filamentous fungal host cell is an *Aspergillus niger, Aspergillus oryzae, Aspergillus sojae, Aspergillus terreus, Chrysosporum lucknowense, Trichoderma reesei* or *Penicillium chrysogenum* host cell. A most preferred *Aspergillus niger* host cell is CBS513.88 or derivatives thereof.

In another preferred embodiment, the yield of the compound of interest produced by the filamentous fungal host of the invention comprising a given copy number of the nucleic acid construct of the third aspect of the invention, is preferably 0.1 g per liter, 0.2 g, 0.3 g, 0.4 g, more preferably 0.5 g and even most preferably more than 0.5 g per liter of the compound of interest. The production of the compound of interest can be determined by a specific assay. Preferably, the filamentous fungal host cell of the present invention is an *Aspergillus, Trichoderma, Fusarium, Chrysosporum* or *Penicillium* host cell. More preferably the filamentous fungal host cell is an *Aspergillus niger, Aspergillus oryzae, Aspergillus sojae, Aspergillus terreus, Chrysosporum lucknowense, Trichoderma reesei* or *Penicillium chrysogenum* host cell. A most preferred *Aspergillus niger* host cell is CBS513.88 or derivatives thereof.

Alternatively and according to another preferred embodiment, when the polypeptide is an enzyme involved in the production of a given metabolite such as (beta-lactam) antibiotics or carotenoids, the filamentous fungal host cell of the invention is used for the production of a given metabolite.

According to a further aspect of the invention, there is provided the use of any one of the nucleotide sequences defined in the corresponding section in a method for producing a compound of interest, the use of a nucleic acid construct or expression vector defined in the corresponding section in a method for producing a compound of interest and the use of any one of the filamentous fungal host cells as defined in the corresponding section in a method for producing a compound of interest.

Method for Producing a Nucleotide Sequence; Calculation of the Optimized Codon Frequency.

According to a further aspect of this invention, there is provided a method for producing the nucleotide sequence of the first aspect of the invention, comprising the steps of:
  providing a synonymous nucleotide coding sequence with optimized codon frequency as defined in the first aspect of the invention, and optionally
  operably linking said synonymous nucleotide coding sequence to the control sequences as defined the first aspect of the invention.

To provide a synonymous nucleotide coding sequence with optimized coding frequency, the optimized coding frequency can be calculated by the method provided by the invention. This method is outlined below.

For the amino acids, hereafter called as group 1 amino acids (AA), there is only one possibility. Group 1 consists of methionine that is always encoded by ATG and tryptophane that is always encoded by TGG.

The amino acids, hereafter called as group 2 AA, are subject to optimization according to the extreme frequency of 0% or 100%, the strategy is clear. All codons for a group 2 AA are specifically changed into the codons listed below. More specifically:
  cysteine is always encoded by TGC;
  phenylalanine by TTC;
  histidine by CAC;
  lysine by AAG,
  asparagine by AAC;
  glutamine by CAG;
  tyrosine by TAC.

All other M, hereafter called group 3 M, can be encoded by several codons as indicated in Table 1; each codon being present in a preferred codon frequency:
  alanine is encoded by GCT, GCC, GCA, or GCG;
  aspartate by GAT, GAC;
  glutamate by GAA, GAG;
  glycine by GGT, GGC, GGA, GGG;
  isoleucine by ATT, ATC, ATA;
  leucine by TTA, TTG, CTT, CTC, CTA, CTG;
  proline by CCT, CCC, CCA, CCG;
  arginine by CGT, CGC, CGA, CGG, AGA, AGG;
  serine by TCT, TCC, TCA, TCG, AGT, AGC;
  threonine by ACT, ACC, ACA, ACG;
  valine by GTT, GTC, GTA, GTG.

The following rules apply for calculation of the optimized codon frequency for group 3 AA in a given coding sequence:

For the group 3 AA and their different corresponding codons, the calculation of the optimal occurrence of each possible codon within a given coding sequence is preferably performed according to the following methodology:
  i. sum for each of the respective group 3 AA, the total number of residues encoded in the given sequence,
  ii. for each AA and codon encoding that M, multiply the total number for that AA by the optimal codon distribution in Table 1, resulting in a raw codon distribution, which generally may contain decimal numbers,
  iii. round off the values of the raw codon distribution (ii), by removing the digits, resulting in a rounded off codon distribution,
  iv. sum for each of the AA, the total number of M represented in the rounded off codon distribution (iii),
  v. calculate the total missing number of residues for each of the respective AA in the rounded off codon distribution, by subtracting the total number of residues encoded in the given sequence (i) with the total number of AA represented in the rounded off codon distribution (iv)
  vi. calculate for each codon, the decimal difference between the raw codon distribution (ii) and the rounded off codon distribution (iii) by subtraction
  vii. multiply for each codon, the decimal difference (vi) and the optimal codon distribution in table 1, giving a weight value for each codon,
  viii. for each of the respective AA, select for the amount of missing residues (v), the respective amount of codons that have the highest weight value (vii),
  ix. the calculation of the final optimal codon distribution within a given sequence encoding a polypeptide is calculated by summing the rounded off codon distribution (iii) and the selected amount of missing residues (viii) for each codon.

Subsequently, for codons of which the total number in a given sequence is higher than in the calculated final optimal codon distribution, a selection is made for substitution into a different corresponding codon as calculated. Also for codons that should be increased in frequency, a selection is made from the other different corresponding codon candidates that should be decreased in frequency (see example 1). In another preferred method, one might consider using a computer algorithm for selection and calculation of codon replacements in a given nucleotide sequence. In another preferred embodiment, the selection and calculation of codon replacements may be done according to the calculated codon frequency and criteria for secondary structures and other features like inclusion of certain RNA-tags or restriction sites, and avoiding certain nucleotide sequences. "Secondary structure" refers to regions of a nucleic acid sequence that, when single stranded, have a tendency to form double-stranded hairpin structures or loops. Such structures may impede transcription and translation. In WO 01/55342 possible ways are provided how to evaluate nucleic acids for their likeliness to form secondary structures. Several software programs can predict secondary structures. In a preferred embodiment the secondary structure is determined by the nearest-neighbor method. A description of this method is described by Freier et al (Proc Natl Acad Sci USA 1986, 83, 9373-9377), and uses the energy parameters which refer to RNA:RNA secondary structure. The application of this method can be done in the Clone Manager 7 program (Sci. Ed. Central: Scientific & Educational software, version 7.02).

According to another preferred method, one applies the optimized codon frequency according to Table 1 to a specific part of the coding sequence only. In a more preferred embodiment of the invention, the substitution of codons in a given nucleotide sequence is performed after doing a random selection of candidates for replacement, and a random selection of new corresponding codon candidates, according to the final optimal codon distribution.

According to another preferred method, one applies the calculated optimal codon distribution based on an amino acid sequence only. The amino acid sequence is back-translated into a nucleotide sequence by an appropriate choice of codons according to the calculated optimal codon distribution into a modified coding sequence with optimized codon frequency (example 2). After design of the modified coding sequence, it might be checked for secondary structure features, AT-rich stretches and unwanted restriction sites. In case one observes such aspects, a person skilled in the art knows how to interchange or replace specific codons of the modified coding sequence to circumvent the specific issue without changing the encoded polypeptide. In a preferred embodiment, this can be done by a computer algorithm taking into account specific criteria for secondary structure, avoiding AT-rich regions, avoiding GC-rich regions, introduction of restriction sites, etc. In another embodiment, the back-translation is done by a random choice of position for each codon that needs to be placed in the nucleotide sequence.

To provide the nucleotide sequence with the desired modifications, general molecular biological methods can be applied. These techniques for modifying nucleotide sequences utilizing cloning methods are well known in the art. Such methods include e.g.: random or directed mutagenesis, DNA shuffling methods, DNA reassembly methods, gene synthesis, and other means known to one skilled in the art (see for example Young and Dong, (2004), Nucleic Acids Research 32, (7) electronic access nar.oupjournals.org/cgil-reprint/3217/e59 or Gupta et al. (1968), Proc. Natl. Acad. Sci USA, 60: 1338-1344; Scarpulla et al. (1982), Anal. Biochem. 121: 356-365; Stemmer et al. (1995), Gene 164: 49-53).

According to yet another preferred embodiment, there is provided a method for producing the nucleotide sequence of the second aspect of the invention by providing a nucleotide sequence with a translational initiator sequence according to the second aspect of the invention. The techniques for modifying nucleic acid sequences utilizing cloning methods are well known in the art.

According to a yet another preferred embodiment, there is provided a method for producing a nucleotide sequence comprising a synonymous nucleotide coding sequence displaying the combined features of the first and second aspect of the invention by:

providing the synonymous nucleotide coding sequence with optimized codon frequency as defined in the first aspect of the invention using the method described above, providing the nucleotide sequence with a translational initiator sequence according to the second aspect of the invention using the method described above, and optionally operably linking said synonymous nucleotide coding sequence to the control sequences as defined the first aspect of the invention.

The present invention is further described by the following examples, which should not be construed as limiting the scope of the invention.

EXAMPLES

Experimental Information

Strains

WT 1: This *A. niger* strain is used as a wild-type strain. This strain is deposited at the CBS Institute under the deposit number CBS 513.88.

WT 2: This *A. niger* strain is a WT 1 strain comprising a deletion of the gene encoding glucoamylase (glaA). WT 2 was constructed by using the "MARKER-GENE FREE" approach as described in EP 0 635 574 B1. In this patent it is extensively described how to delete glaA specific DNA sequences in the genome of CBS 513.88. The procedure resulted in a MARKER-GENE FREE? glaA recombinant *A. niger* CBS 513.88 strain, possessing finally no foreign DNA sequences at all.

WT 3: This *A. niger* strain is a WT 2 strain comprising a mutation which results in an oxalate deficient *A. niger* strain. WT 3 was constructed by using the method as described in EP1590444. In this patent application, it is extensively described how to screen for an oxalate deficient *A. niger* strain. Strain WT3 was constructed according to the methods of examples 1 and 2 of EP1590444, strain WT 3 is mutant strain 22 of EP1590444 (designated FINAL in EP1590444).

*A. niger* Shake Flask Fermentations

*A. niger* strains were pre-cultured in 20 ml pre-culture medium as described in the Examples: "*A. niger* shake flask fermentations" section of WO99/32617. After overnight growth, 10 ml of this culture was transferred to fermentation medium 1 (FM1) for alpha-amylase fermentations and fermentation medium 2 (FM2) for phospholipase A1 fermentations. Fermentation is performed in 500 ml flasks with baffle with 100 ml fermentation broth at 34° C. and 170 rpm for the number of days indicated, generally as described in WO99/32617.

This FM1 medium contains per liter: 70 g glucose, 25 g Caseinhydrolysate, 12.5 g Yeast extract, 1 g KH2PO4, 2 g K2SO4, 0.5 g MgSO4.7H2O, 0.03 g ZnCl2, 0.02 g CaCl2, 0.01 g MnSO4.4H2O, 0.3 g FeSO4.7H2O, 10 ml Pen-Strep (Invitrogen, cat. nr. 10378-016), adjusted to pH 5.6 with 4 NH2SO4.

The FM2 medium contains per liter: 82.5 g Glucose.1H$_2$O, 25 g Maldex 15 (Boom Meppel, Netherlands), 2 g Citric acid, 4.5 g NaH2PO4.1H2O, 9 g KH2PO4, 15 g (NH4)2SO4, 0.02 g ZnCl2, 0.1 g MnSO4.1H2O, 0.015 g CuSO4.5H2O, 0.015 g CoCl2.6H2O, 1 g MgSO4.7H2O, 0.1 g CaCl2.2H2O, 0.3 g FeSO4.7H2O, 30 g MES (2-[N-Morpholino]ethanesulfonic acid), pH=6.

PLA1 Phospholipase Activity

To determine phospholipase PLA1 activity (pla1) in *A. niger* culture broth spectrophotometrically, an artificial substrate is used: 1,2-dithiodioctanoyl phophatidylcholine (diC8, substrate). pla1 hydrolyses the sulphide bond at the A1 position, dissociating thio-octanoïc acid. Thio-octanoïc acid reacts with 4,4 dithiopyridine (color reagent, 4-DTDP), forming 4-thiopyridone. 4-Thiopyridone is in tautomeric equilibrium with 4-mercaptopyridine, which absorbs radiation having a wavelength of 334 nm. The extinction change at that wavelength is measured. One unit is the amount of enzyme that liberates of 1 nmol thio-octanoïc acid from 1,2-dithiodioctanoyl phosphatidylcholine per minute at 37° C. and pH 4.0.

The substrate solution is prepared by dissolving 1 g diC8 crystals per 66 ml ethanol and add 264 ml acetate buffer. The acetate buffer comprises 0.1 M Acetate buffer pH 3.85 containing 0.2% Triton-X100. The color reagent is a 11 mM 4,4-dithiodipyridine solution. It was prepared by weighting 5.0 mg 4,4-dithiodipyridine in a 2 ml Eppendorf sample cup and dissolving in 1.00 ml ethanol. 1.00 ml of milli-Q water was added.

Fungal Alpha-Amylase Activity

To determine the alpha-amylase activity in *A. niger* culture broth, the Megazyme cereal alpha-amylase kit is used (Megazyme, CERALPHA alpha amylase assay kit, catalogus. ref. K-CERA, year 2000-2001), according protocol of the supplier. The measured activity is based on hydrolysis of non-reducing-endblocked p-nitrophenyl maltoheptaoside in the presence of excess glucoamylase and α-glucosidase. The amount of formed p-nitrophenol is a measure for alpha-amylase activity present in a sample.

Example 1

Construction of an *Aspergillus* Expression Construct for the pla1 Gene Encoding *A. Oryzae* Phospholipase A1 and the amyA Gene Encoding *A. Niger* Alpha-Amylase The DNA sequence of the pla1 gene encoding the phospholipase A1 protein was disclosed in JP 1998155493-A/1 and also can be retrieved from EMBL Nucleotide Sequence Database (http://www.ebi.ac.uk/embl/index.html) under accession number E16314. The genomic sequence of the native *A. oryzae* pla1 gene is shown as SEQ ID NO: 1. The corresponding coding sequence of pla1 is shown as SEQ ID NO: 2. The translated sequence of SEQ ID NO: 2 is assigned as the SEQ ID NO: 3, representing the *A. oryzae* phospholipase A1.

The DNA sequence of the amyA gene encoding the alpha-amylase protein was disclosed in Curr Genet. 1990 March; 17(3):203-212 (Cloning, characterization, and expression of two alpha-amylase genes from *Aspergillus niger* var. *awamori* by Korman D R, Bayliss F T, Barnett C C, Carmona C L, Kodama K H, Royer T J, Thompson S A, Ward M, Wilson L J, Berka R M) and also can be retrieved from EMBL Nucleotide Sequence Database (http://www.ebi.ac.uk/embl/index.html) under accession number AB109452. The genomic sequence of the native *A. niger* amyA gene is shown as SEQ ID NO. 28. The corresponding coding or cDNA sequence of amyA is shown as SEQ ID NO. 29. The translated sequence of SEQ ID NO. 29 is assigned as the SEQ ID NO. 30, representing the *A. niger* alpha-amylase protein.

Figure 2:
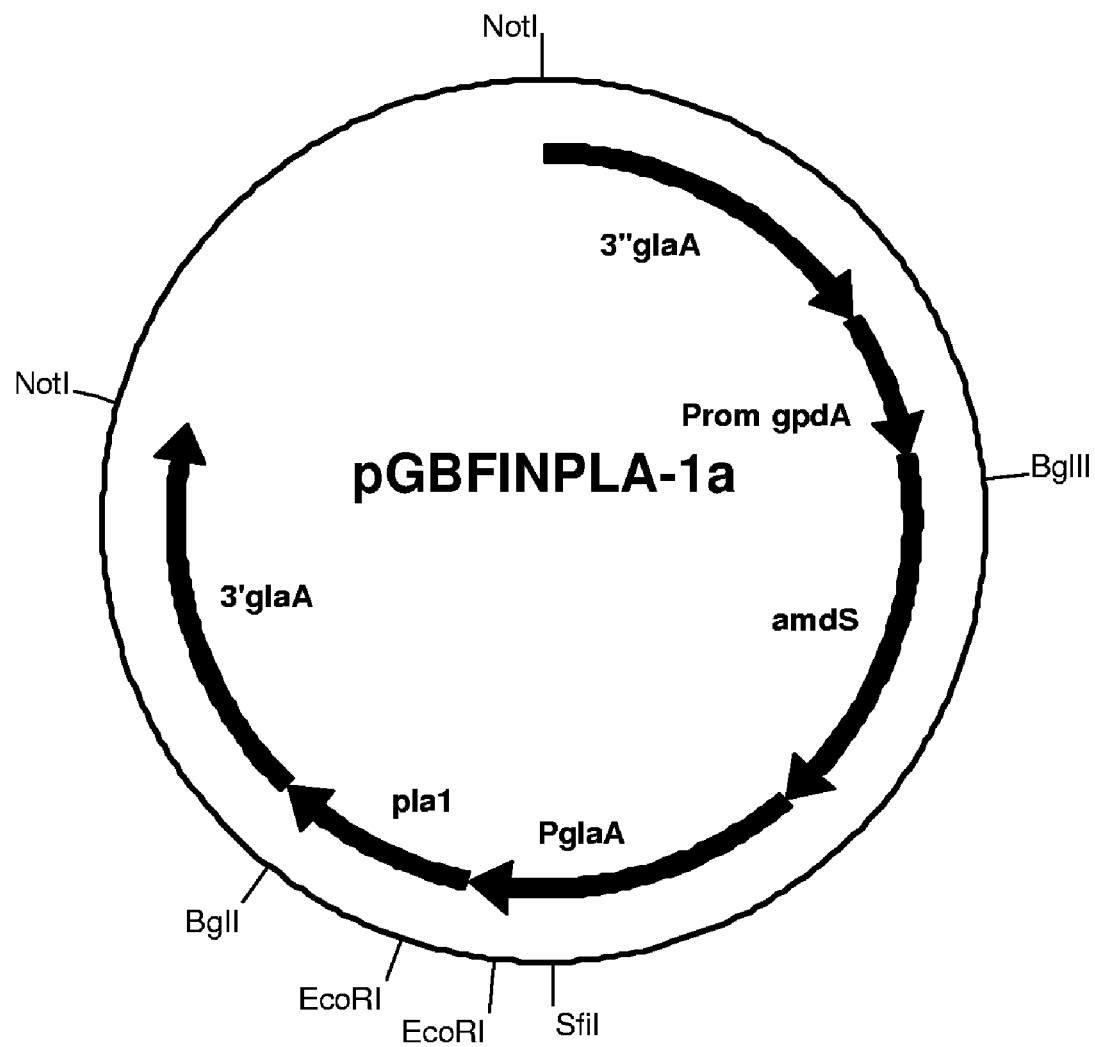
Figure 4:
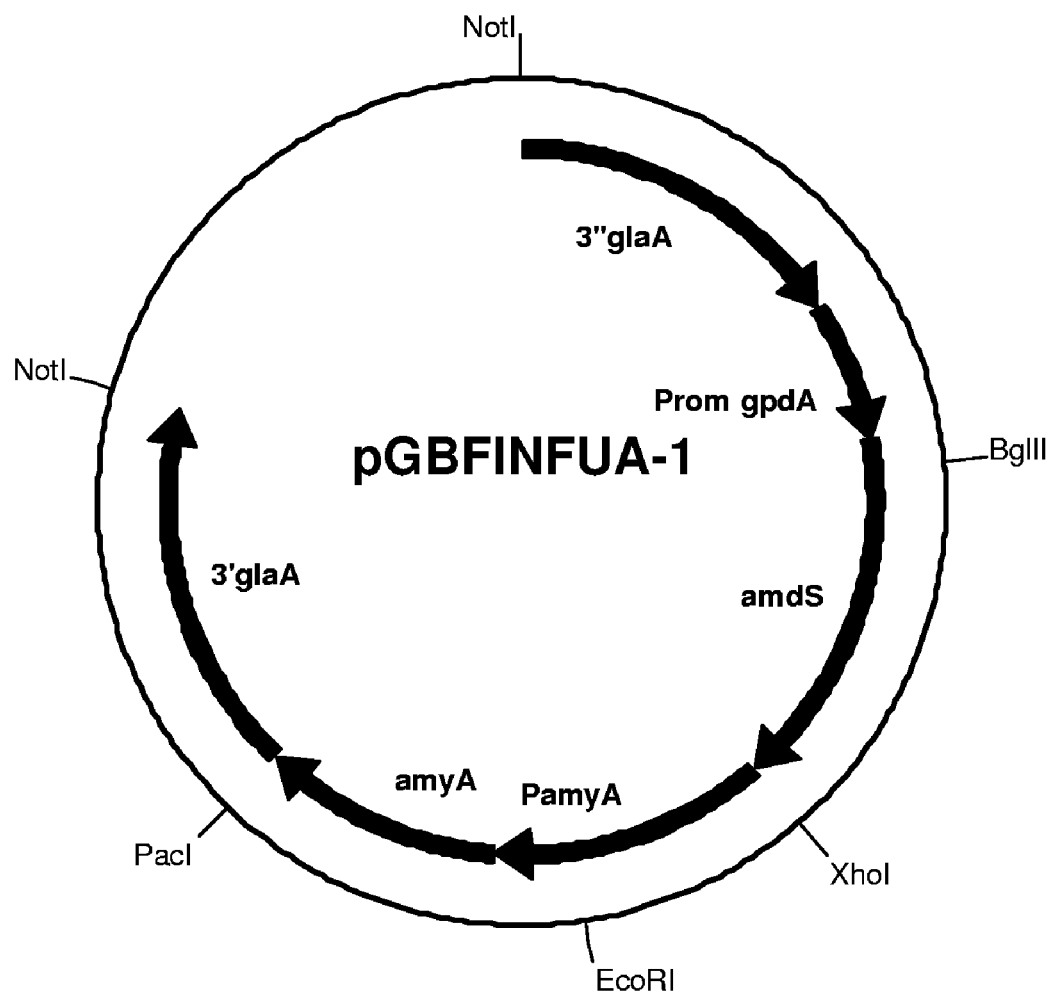
FIG. 4 depicts a plasmid map of expression vector pGBFINFUA-1.

For expression analysis in *Aspergillus* species of pla1 constructs, a fusion of the genomic pla1 gene and the *A. niger* glucoamylase promoter was made at the translation start site accompanied by the introduction of cloning sites. To do so, a PCR was performed for amplification of the genomic pla1 gene using the oligonucleotides identified as SEQ ID NO 4 and SEQ ID NO 5 and the pla1 gene construct cloned in pGBFIN11, described in WO 04/070022, as template, generating a 1.1 kb fragment identified as fragment A. Additionally, a SnaBI cloning site was introduced. A second PCR was performed using the oligonucleotides identified as SEQ ID NO 6 and SEQ ID NO 7 and the pGBFIN-23 vector (described in WO99/32617) as template, generating a 0.4 kb glaA promoter fragment identified as fragment B. Both resulting fragments, A and B, were fused by sequence overlap extension (SOE-PCR, as described in Gene. 1989 Apr. 15; 77(1):51-9. Ho S N, Hunt H D, Horton R M, Pullen J K, Pease L R "Site-directed mutagenesis by overlap extension using the polymerase chain reaction") using PCR, oligonucleotides identified as SEQ ID NO 5 and SEQ ID ND 6 and fragments A and B described above; generating a 1.4 kb fragment C. This fragment C, comprising the genomic pla1 gene and part of the glaA promoter was digested with SfiI and SnaBI and introduced in a SfiI and NruI digested pGBFIN-30 vector (FIG. 1), generating pGBFINPLA-1a (FIG. 2). The sequence of the introduced and digested PCR fragment C was confirmed by sequence analysis and its sequence is given in SEQ ID NO 8. For expression analysis in *Aspergillus* species of *A. niger* amyA constructs, a fragment containing the genomic amyA promoter and the amyA cDNA sequence was amplified and fused using PCR in a similar strategy as described above. Appropriate restriction sites were introduced at both ends to allow cloning in an expression vector. At the 5'-end an XhoI site was introduced and at the 3'-end a PacI site. This fragment comprising the alpha-amylase promoter and cDNA sequence was digested with XhoI and PacI and introduced in an XhoI and PacI digested pGBFIN-12 vector (construction and layout described in WO99/32617), generating pGBFINFUA-1 (FIG. 4). The sequence of the introduced PCR fragment was confirmed by sequence analysis and its sequence is presented in SEQ ID NO. 31.

Example 2

Use of a Method of the Invention for Construction of Improved DNA Sequences for Improving Production of the Phospholipase A1 Enzyme of *Aspergillus oryzae* in *A. niger*

2.1. Improvement of the Codon Frequency or Codon Usage for the *A. Oryzae* Phospholipase A1 Coding Sequence for Expression in *A. Niger*

The method of the invention was below applied to the improvement of codon use of the PLA1 gene of *A. oryzae*. This method can be applied the same way for the improvement of codon use of any nucleotide sequence. The nucleotide coding sequence of pla1 is shown as SEQ ID NO:2.

The codon use of the native *A. oryzae* gene encoding PLA1 and the synthetic optimized variant are given in Table 2 below. For the native and optimized synthetic pla1 gene, the exact numbers for each codon are given as well as the distribution per amino acid. Additionally, the third column provides the proposed optimal distribution, which is the target for optimization.

For the group 1 amino acids, there is only one possibility. Group 1 consists of methionine that is always encoded by ATG and tryptophane that is always encoded by TGG.

The group 2 amino acids are subject to optimization according to the extreme frequency of 0% or 100%, the strategy is clear. All codons for a group 2 AA are specifically changed into the optimal variant of the two possible codons. More specifically for cysteine, a codon, TGT is replaced by TGC; for phenylalanine, TTT by TTC; for histidine, CAT by CAC; for lysine, AAA by MG, for asparagine, MT by AAC; for glutamine, CM by CAG; for tyrosine, TAT by TAC.

The group 3 amino acids can be encoded by several codons as indicated in Table 1; each codon being present in a preferred codon frequency: for alanine GCT, GCC, GCA, GCG; for aspartate, GAT, GAC; for glutamate, GAA, GAG; for glycine, GGT, GGC, GGA, GGG; for isoleucine, ATT, ATC, ATA; for leucine, TTA, TTG, CTT, CTC, CTA, CTG; for proline, CCT, CCC, CCA, CCG; for arginine, CGT, CGC, CGA, CGG, AGA, AGG; for serine, TCT, TCC, TCA, TCG, AGT, AGC; for threonine, ACT, ACC, ACA, ACG; for valine, GTT, GTC, GTA, GTG, are optimized according the following methodology:

For the group 3 amino acids (AA) and their encoding codons, the calculation of the optimal occurrence of each possible codon within a given coding sequence is performed according to the following methodology:

i. sum for each of the respective group 3 AA, the total number of residues encoded in the given sequence, see column A1 (Table 3), ii. for each AA and codon encoding that AA, multiply the total number for that AA by the optimal codon distribution in Table 1, resulting in a raw codon distribution, which generally may contain decimal numbers, see column A2 (Table 4), iii. round off the values of the raw codon distribution (ii), by removing the digits, resulting in a rounded off codon distribution, see column A3 (Table 4), iv. sum for each of the AA, the total number of AA represented in the rounded off codon distribution (iii), see column A4 (Table 3), v. calculate the total missing number of residues for each of the respective AA in the rounded off codon distribution, by subtracting the total number of residues encoded in the given sequence (i) with the total number of AA represented in the rounded off codon distribution (iv), see column A5 (Table 3), vi. calculate for each codon, the decimal difference between the raw codon distribution (ii) and the rounded off codon distribution (iii) by subtraction, see column A6 (Table 4), vii. multiply for each codon, the decimal difference (vi) and the optimal codon distribution in table 1, giving a weight value for each codon, see column A7 (Table 4), viii. for each of the respective AA, select for the amount of missing residues (v), the respective amount of codons that have the highest weight value (vii), see column A8 (Table 4), ix. the calculation of the final optimal codon distribution within a given sequence encoding a polypeptide is calculated by summing the rounded off codon distribution (iii) and the selected amount of missing residues (viii) for each codon, see column A9 (Table 4).

TABLE 2

Codon optimization for PLA1.

| AA | Codon | Optimal codon distribution [%] | PLA1 w.t. [# codons] | PLA1 w.t. [% codons/AA] | PLA1 optimized [# codons] | PLA1 optimized [% codons/AA] |
|---|---|---|---|---|---|---|
| A | Ala_GCT | 38 | 10 | 28.6 | 14 | 40.0 |
|   | Ala_GCC | 51 | 12 | 34.3 | 18 | 51.4 |
|   | Ala_GCA | 0 | 9 | 25.7 | 0 | 0.0 |
|   | Ala_GCG | 11 | 4 | 11.4 | 3 | 8.6 |
| C | Cys_TGT | 0 | 4 | 66.7 | 0 | 0.0 |
|   | Cys_TGC | 100 | 2 | 33.3 | 6 | 100.0 |
| D | Asp_GAT | 36 | 14 | 73.7 | 7 | 36.8 |
|   | Asp_GAC | 64 | 5 | 26.3 | 12 | 63.2 |
| E | Glu_GAA | 26 | 7 | 46.7 | 4 | 26.7 |
|   | Glu_GAG | 74 | 8 | 53.3 | 11 | 73.3 |
| F | Phe_TTT | 0 | 5 | 55.6 | 0 | 0.0 |
|   | Phe_TTC | 100 | 4 | 44.4 | 9 | 100.0 |
| G | Gly_GGT | 49 | 6 | 26.1 | 12 | 52.2 |
|   | Gly_GGC | 35 | 7 | 30.4 | 8 | 34.8 |
|   | Gly_GGA | 16 | 5 | 21.7 | 3 | 13.0 |
|   | Gly_GGG | 0 | 5 | 21.7 | 0 | 0.0 |
| H | His_CAT | 0 | 4 | 50.0 | 0 | 0.0 |
|   | His_CAC | 100 | 4 | 50.0 | 8 | 100.0 |
| I | Ile_ATT | 27 | 3 | 33.3 | 2 | 22.2 |
|   | Ile_ATC | 73 | 6 | 66.7 | 7 | 77.8 |
|   | Ile_ATA | 0 | 0 | 0.0 | 0 | 0.0 |
| K | Lys_AAA | 0 | 2 | 33.3 | 0 | 0.0 |
|   | Lys_AAG | 100 | 4 | 66.7 | 6 | 100.0 |
| L | Leu_TTA | 0 | 1 | 2.9 | 0 | 0.0 |
|   | Leu_TTG | 13 | 9 | 26.5 | 4 | 11.8 |
|   | Leu_CTT | 17 | 2 | 5.9 | 6 | 17.6 |
|   | Leu_CTC | 38 | 8 | 23.5 | 13 | 38.2 |
|   | Leu_CTA | 0 | 2 | 5.9 | 0 | 0.0 |
|   | Leu_CTG | 32 | 12 | 35.3 | 11 | 32.4 |
| M | Met_ATG | 100 | 1 | 100.0 | 1 | 100.0 |
| N | Asn_AAT | 0 | 5 | 27.8 | 0 | 0.0 |
|   | Asn_AAC | 100 | 13 | 72.2 | 18 | 100.0 |
| P | Pro_CCT | 36 | 3 | 37.5 | 3 | 37.5 |
|   | Pro_CCC | 64 | 2 | 25.0 | 5 | 62.5 |

TABLE 2-continued

Codon optimization for PLA1.

| AA | Codon | Optimal codon distribution [%] | PLA1 w.t. [# codons] | PLA1 w.t. [% codons/AA] | PLA1 optimized [# codons] | PLA1 optimized [% codons/AA] |
|---|---|---|---|---|---|---|
|  | Pro_CCA | 0 | 2 | 25.0 | 0 | 0.0 |
|  | Pro_CCG | 0 | 1 | 12.5 | 0 | 0.0 |
| Q | Gln_CAA | 0 | 3 | 60.0 | 0 | 0.0 |
|  | Gln_CAG | 100 | 2 | 40.0 | 5 | 100.0 |
| R | Arg_CGT | 49 | 0 | 0.0 | 4 | 50.0 |
|  | Arg_CGC | 51 | 2 | 25.0 | 4 | 50.0 |
|  | Arg_CGA | 0 | 2 | 25.0 | 0 | 0.0 |
|  | Arg_CGG | 0 | 3 | 37.5 | 0 | 0.0 |
|  | Arg_AGA | 0 | 1 | 12.5 | 0 | 0.0 |
|  | Arg_AGG | 0 | 0 | 0.0 | 0 | 0.0 |
| S | Ser_TCT | 21 | 5 | 15.2 | 7 | 21.2 |
|  | Ser_TCC | 44 | 7 | 21.2 | 15 | 45.5 |
|  | Ser_TCA | 0 | 5 | 15.2 | 0 | 0.0 |
|  | Ser_TCG | 14 | 2 | 6.1 | 4 | 12.1 |
|  | Ser_AGT | 0 | 4 | 12.1 | 0 | 0.0 |
|  | Ser_AGC | 21 | 10 | 30.3 | 7 | 21.2 |
| T | Thr_ACT | 30 | 7 | 29.2 | 7 | 29.2 |
|  | Thr_ACC | 70 | 8 | 33.3 | 17 | 70.8 |
|  | Thr_ACA | 0 | 2 | 8.3 | 0 | 0.0 |
|  | Thr_ACG | 0 | 7 | 29.2 | 0 | 0.0 |
| V | Val_GTT | 27 | 5 | 33.3 | 4 | 26.7 |
|  | Val_GTC | 54 | 4 | 26.7 | 8 | 53.3 |
|  | Val_GTA | 0 | 1 | 6.7 | 0 | 0.0 |
|  | Val_GTG | 19 | 5 | 33.3 | 3 | 20.0 |
| W | Trp_TGG | 100 | 4 | 100.0 | 4 | 100.0 |
| Y | Tyr_TAT | 0 | 6 | 40.0 | 0 | 0.0 |
|  | Tyr_TAC | 100 | 9 | 60.0 | 15 | 100.0 |

TABLE 3

| AA(i) | i | A1 | A4 | A5 |
|---|---|---|---|---|
| Ala | 1 | 35 | 33 | 2 |
| Asp | 2 | 19 | 18 | 1 |
| Glu | 3 | 15 | 14 | 1 |
| Gly | 4 | 23 | 22 | 1 |
| Ile | 5 | 9 | 8 | 1 |
| Leu | 6 | 34 | 31 | 3 |
| Pro | 7 | 8 | 7 | 1 |
| Arg | 8 | 8 | 7 | 1 |
| Ser | 9 | 33 | 30 | 3 |
| Thr | 10 | 24 | 23 | 1 |
| Val | 11 | 15 | 14 | 1 |

TABLE 4

| Codon | A2 | A3 | A6 | A7 | A8 | A9 |
|---|---|---|---|---|---|---|
| Ala_GCT | 13.3 | 13 | 0.3 | 0.114 | 1 | 14 |
| Ala_GCC | 17.85 | 17 | 0.85 | 0.434 | 1 | 18 |
| Ala_GCA | 0 | 0 | 0 | 0.000 | 0 | 0 |
| Ala_GCG | 3.85 | 3 | 0.85 | 0.094 | 0 | 3 |
| Asp_GAT | 6.84 | 6 | 0.84 | 0.302 | 1 | 7 |
| Asp_GAC | 12.16 | 12 | 0.16 | 0.102 | 0 | 12 |
| Glu_GAA | 3.9 | 3 | 0.9 | 0.234 | 1 | 4 |
| Glu_GAG | 11.1 | 11 | 0.1 | 0.074 | 0 | 11 |
| Gly_GGT | 11.27 | 11 | 0.27 | 0.132 | 1 | 12 |
| Gly_GGC | 8.05 | 8 | 0.05 | 0.018 | 0 | 8 |
| Gly_GGA | 3.68 | 3 | 0.68 | 0.109 | 0 | 3 |
| Gly_GGG | 0 | 0 | 0 | 0.000 | 0 | 0 |
| Ile_ATT | 2.43 | 2 | 0.43 | 0.116 | 0 | 2 |
| Ile_ATC | 6.57 | 6 | 0.57 | 0.416 | 1 | 7 |
| Ile_ATA | 0 | 0 | 0 | 0.000 | 0 | 0 |
| Leu_TTA | 0 | 0 | 0 | 0.000 | 0 | 0 |
| Leu_TTG | 4.42 | 4 | 0.42 | 0.055 | 0 | 4 |
| Leu_CTT | 5.78 | 5 | 0.78 | 0.133 | 1 | 6 |
| Leu_CTC | 12.92 | 12 | 0.92 | 0.350 | 1 | 13 |
| Leu_CTA | 0 | 0 | 0 | 0.000 | 0 | 0 |
| Leu_CTG | 10.88 | 10 | 0.88 | 0.282 | 1 | 11 |
| Pro_CCT | 2.88 | 2 | 0.88 | 0.317 | 1 | 3 |
| Pro_CCC | 5.12 | 5 | 0.12 | 0.077 | 0 | 5 |
| Pro_CCA | 0 | 0 | 0 | 0.000 | 0 | 0 |
| Pro_CCG | 0 | 0 | 0 | 0.000 | 0 | 0 |
| Arg_CGT | 3.92 | 3 | 0.92 | 0.451 | 1 | 4 |
| Arg_CGC | 4.08 | 4 | 0.08 | 0.041 | 0 | 4 |
| Arg_CGA | 0 | 0 | 0 | 0.000 | 0 | 0 |
| Arg_CGG | 0 | 0 | 0 | 0.000 | 0 | 0 |
| Arg_AGA | 0 | 0 | 0 | 0.000 | 0 | 0 |
| Arg_AGG | 0 | 0 | 0 | 0.000 | 0 | 0 |
| Ser_TCT | 6.93 | 6 | 0.93 | 0.195 | 1 | 7 |
| Ser_TCC | 14.52 | 14 | 0.52 | 0.229 | 1 | 15 |
| Ser_TCA | 0 | 0 | 0 | 0.000 | 0 | 0 |
| Ser_TCG | 4.62 | 4 | 0.62 | 0.087 | 0 | 4 |
| Ser_AGT | 0 | 0 | 0 | 0.000 | 0 | 0 |
| Ser_AGC | 6.93 | 6 | 0.93 | 0.195 | 1 | 7 |
| Thr_ACT | 7.2 | 7 | 0.2 | 0.060 | 0 | 7 |
| Thr_ACC | 16.8 | 16 | 0.8 | 0.560 | 1 | 17 |
| Thr_ACA | 0 | 0 | 0 | 0.000 | 0 | 0 |
| Thr_ACG | 0 | 0 | 0 | 0.000 | 0 | 0 |
| Val_GTT | 4.05 | 4 | 0.05 | 0.014 | 0 | 4 |
| Val_GTC | 8.1 | 8 | 0.1 | 0.054 | 0 | 8 |
| Val_GTA | 0 | 0 | 0 | 0.000 | 0 | 0 |
| Val_GTG | 2.85 | 2 | 0.85 | 0.162 | 1 | 3 |

Subsequently, for codons of which the total number in the pla1 coding sequence was higher than the calculated final codon distribution, a random selection was made for substitution into a different corresponding codon as calculated. Also for codons that should be increased in the pla1 coding sequence, a random selection was made from the other different corresponding codon candidates that should be decreased in frequency.

Figure 6:
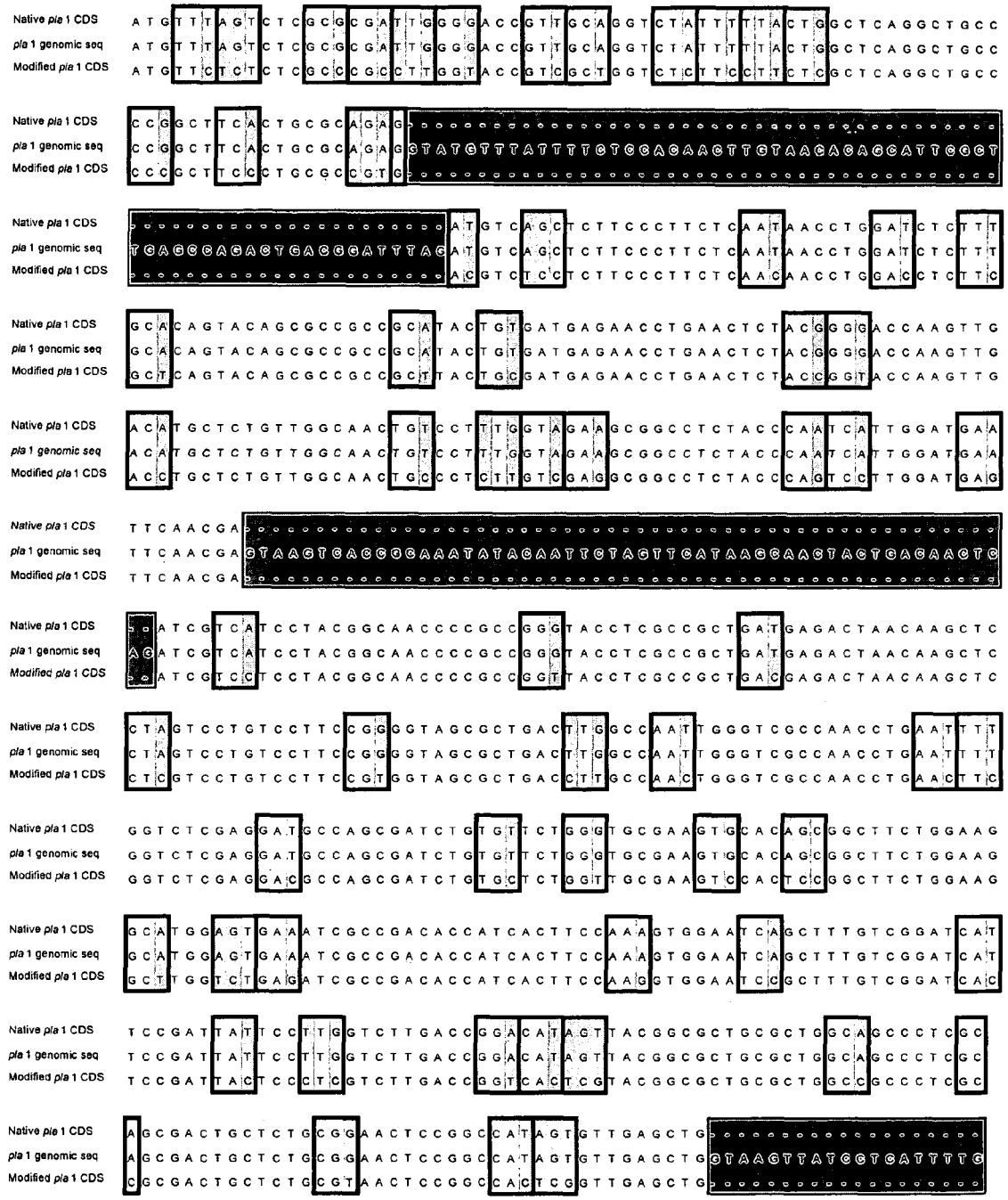
FIG. 6 depicts an alignment of the native pla1 coding sequence (SEQ ID NO: 2), the native pla1 genomic sequence (SEQ ID NO: 1) and a synthetic optimized pla1 coding sequence (SEQ ID NO: 194). The introns in the genomic sequence are indicated in the pla1 genomic sequence. The codons, which have been changed in the modified pla1 coding sequence, are indicated with boxes. The nucleotides, which have been modified, are indicated in gray.

This resulted in a modified coding sequence (or synonymous coding sequence or optimized synthetic sequence) as depicted in Table 2. The optimized synthetic pla1 sequence, resulting from the process described above, is shown in FIG. 6. Here an alignment of the modified coding sequence of the invention with the native and genomic pla1 sequence can be found. In this modified coding sequence, the three introns of the native sequence were placed at their original position (as indicated in SEQ ID NO 1), resulting in the optimized synthetic sequence as shown in the SEQ ID NO 11. Secondary structures in the modified coding sequence were checked using the Clone Manager 7 program (Sci. Ed. Central: Scientific & Educational software, version 7.02) for possible occurrence of harmful secondary structures.

2.2: Choice of a Modified Translational Termination Sequence

The native pla1 gene encoding A. oryzae phospholipase A1 contains a 'TAG' stop codon followed by TACGTA of the introduced SnaBI restriction site. In a number of synthetic constructs, the 5'-TAGT-3' translational termination sequence is replaced by TAAA followed by the same TACGTA of the SnaBI restriction site. This replacement has been done in the sequences of SEQ ID NO. 11, SEQ ID NO. 12, SEQ ID NO. 13, SEQ ID NO. 14, SEQ ID NO. 35. As a result of this, the expression constructs pGBFINPLA-1d, pGBFINPLA-1e, pGBFINPLA-1f, pGBFINPLA-1 g and pGBFINPLA-1h have a modified translational termination sequence according to the invention.

2.3: Choice of a Modified Translational Initiation Sequences

The strong glaA promotor is applied for over-expression of enzymes in A. niger using the pGBFIN expression constructs. The translational initiation sequence including ATG start codon of PgIaA is 5'-CACCTCAGCA ATG-3' (SEQ ID NO: 181). The translational initiation sequence of PgIaA has been modified into 5'-CACCGTCAAA-3' (SEQ ID NO: 22) or 5'-CGCAGTCAAG-3' (SEQ ID NO: 23). This results in a glucoamylase promoter sequence downstream of the EcoRI site as can be identified in SEQ ID NO 25 and 26, respectively.

This replacement was performed in the sequences of SEQ ID NO. 9, SEQ ID NO. 10, SEQ ID NO. 12, SEQ ID NO. 13 and SEQ ID NO. 14. As a result of this, the expression constructs pGBFINPLA-1b, pGBFINPLA-1c, pGBFINPLA-1e, pGBFINPLA-1f and pGBFINPLA-1g have a modified translational initiation sequence according to the invention. The translational initiator sequence as described in U.S. Pat. No. 6,461,837 B1 has been tested in the sequence of SEQ ID NO. 35, resulting in the expression constructs pGBFINPLA-1 h.

2.4: Choice of Modified Translational Initiation Coding Sequence

Modification of the translational initiation coding sequence can be combined with the codon optimization and/or improvement of the translational initiation coding sequence. Substitution of the second codon in the coding sequence is clear because only one codon is optimal, i.e., the codon is replaced by GCT coding alanine. The third codon has 4 options: TCC; CCC; ACC; GCC, encoding serine, proline, threonine, and arginine, respectively. TCC was selected. The fourth codon can either be TTC for phenylalanine, TTC for serine, CTC for leucine, or CCC for proline. TTC was selected. This leads to 5'-ATGGCTTCCTTC-3' (SEQ ID NO: 182) as modified translational initiation coding sequence including start codon. This results in a glucoamylase promoter sequence downstream of the EcoRI site and with translational initiation coding sequence as can be identified in SEQ ID NO 27. This modified sequence is used in SEQ ID NO. 14. As a result of this, the expression construct pGBFINPLA-1g has a modified translational initiation coding sequence according to the invention.

2.5: Combination of at Least One of the Modifications Made in 2.1 to 2.4

Expression of the nucleotide sequence coding for the polypeptide to be produced may be improved by optimizing the codon usage, and/or the consensus translational initiator coding sequence and/or control DNA sequences comprising a consensus translational initiator sequence and/or optimal translational termination sequence. A series of 8 constructs (Table 5) was analysed to test a number of embodiments of the invention.

TABLE 5

Several improved expression constructs using at least one of the modified sequences. Translational initiator sequence variant 1: CACCGTCAAA (SEQ ID NO: 22); variant 2:CGCAGTCAAG (SEQ ID NO: 23).

| SEQ ID NO | Translational initiation sequence | Translational initiation coding sequence | Codon usage | Translation termination sequence |
|---|---|---|---|---|
| 8 | w.t. | w.t. | w.t. | w.t. |
| 9 | variant 1 | w.t. | w.t. | w.t. |
| 10 | variant 2 | w.t. | w.t. | w.t. |
| 11 | w.t. | w.t. | modified | w.t. |
| 12 | variant 1 | w.t. | modified | Modified (TAA ATA) |
| 13 | variant 2 | w.t. | modified | Modified (TAA ATA) |
| 14 | variant 1 | Optimized (ATGGCTTCCTTC (SEQ ID NO: 182)) | modified | Modified (TAA ATA) |

TABLE 5-continued

Several improved expression constructs using at least one of the modified sequences. Translational initiator sequence variant 1: CACCGTCAAA (SEQ ID NO: 22); variant 2:CGCAGTCAAG (SEQ ID NO: 23).

| SEQ ID NO | Translational initiation sequence | Translational initiation coding sequence | Codon usage | Translation termination sequence |
|---|---|---|---|---|
| 35 | U.S. Pat. No. 6,461,837 B1 | w.t. | modified | Modified (TAA ATA) |

Example 3

Use of a Method of the Invention for Construction of Improved DNA Sequences for Improving Production of the Alpha-Amylase Enzyme in *A. Niger*

3.1. Improvement of the Codon Frequency or Codon Usage for the Alpha-Amylase Coding Sequence amyA for Expression in *A. Niger*

The method of the invention is below applied to the improvement of codon use of the amyA gene of *A. niger*. This method can be applied the same way for the improvement of codon use of any nucleotide sequence. The nucleotide coding sequence of the native amyA is shown as SEQ ID NO. 29.

x. The codon use of the native amyA gene of *A. niger* and the synthetic optimized variant are given in Table 6 below. For the native and optimized synthetic amyA gene, the exact numbers for each codon are given as well as the distribution per amino acid. Additionally, the third column provides the proposed optimal distribution, which is the target for optimization.

TABLE 6

Codon optimization for amyA.

| AA | Codon | Optimal codon distribution [%] | amyA w.t. [# codons] | amyA w.t. [% codons/AA] | amyA optimized [# codons] | amyA optimized [% codons/AA] |
|---|---|---|---|---|---|---|
| A | Ala_GCT | 38 | 5 | 11.9 | 16 | 38.1 |
|   | Ala_GCC | 51 | 15 | 35.7 | 21 | 50.0 |
|   | Ala_GCA | 0 | 12 | 28.6 | 0 | 0.0 |
|   | Ala_GCG | 11 | 10 | 23.8 | 5 | 11.9 |
| C | Cys_TGT | 0 | 7 | 77.8 | 0 | 0.0 |
|   | Cys_TGC | 100 | 2 | 22.2 | 9 | 100.0 |
| D | Asp_GAT | 36 | 20 | 47.6 | 15 | 35.7 |
|   | Asp_GAC | 64 | 22 | 52.4 | 27 | 64.3 |
| E | Glu_GAA | 26 | 5 | 41.7 | 3 | 25.0 |
|   | Glu_GAG | 74 | 7 | 58.3 | 9 | 75.0 |
| F | Phe_TTT | 0 | 3 | 20.0 | 0 | 0.0 |
|   | Phe_TTC | 100 | 12 | 80.0 | 15 | 100.0 |
| G | Gly_GGT | 49 | 10 | 23.3 | 21 | 48.8 |
|   | Gly_GGC | 35 | 18 | 41.9 | 15 | 34.9 |
|   | Gly_GGA | 16 | 10 | 23.3 | 7 | 16.3 |
|   | Gly_GGG | 0 | 5 | 11.6 | 0 | 0.0 |
| H | His_CAT | 0 | 3 | 42.9 | 0 | 0.0 |
|   | His_CAC | 100 | 4 | 57.1 | 7 | 100.0 |
| I | Ile_ATT | 27 | 7 | 25.0 | 7 | 25.0 |
|   | Ile_ATC | 73 | 19 | 67.9 | 21 | 75.0 |
|   | Ile_ATA | 0 | 2 | 7.1 | 0 | 0.0 |
| K | Lys_AAA | 0 | 7 | 35.0 | 0 | 0.0 |
|   | Lys_AAG | 100 | 13 | 65.0 | 20 | 100.0 |
| L | Leu_TTA | 0 | 1 | 2.7 | 0 | 0.0 |
|   | Leu_TTG | 13 | 10 | 27.0 | 5 | 13.5 |
|   | Leu_CTT | 17 | 4 | 10.8 | 6 | 16.2 |
|   | Leu_CTC | 38 | 13 | 35.1 | 14 | 37.8 |
|   | Leu_CTA | 0 | 3 | 8.1 | 0 | 0.0 |
|   | Leu_CTG | 32 | 6 | 16.2 | 12 | 32.4 |
| M | Met_ATG | 100 | 10 | 100.0 | 10 | 100.0 |
| N | Asn_AAT | 0 | 3 | 11.5 | 0 | 0.0 |
|   | Asn_AAC | 100 | 23 | 88.5 | 26 | 100.0 |
| P | Pro_CCT | 36 | 6 | 27.3 | 8 | 36.4 |
|   | Pro_CCC | 64 | 8 | 36.4 | 14 | 63.6 |
|   | Pro_CCA | 0 | 3 | 13.6 | 0 | 0.0 |
|   | Pro_CCG | 0 | 5 | 22.7 | 0 | 0.0 |
| Q | Gln_CAA | 0 | 5 | 25.0 | 0 | 0.0 |
|   | Gln_CAG | 100 | 15 | 75.0 | 20 | 100.0 |
| R | Arg_CGT | 49 | 1 | 10.0 | 5 | 50.0 |
|   | Arg_CGC | 51 | 2 | 20.0 | 5 | 50.0 |
|   | Arg_CGA | 0 | 2 | 20.0 | 0 | 0.0 |

TABLE 6-continued

Codon optimization for amyA.

| AA | Codon | Optimal codon distribution [%] | amyA w.t. [# codons] | amyA w.t. [% codons/AA] | amyA optimized [# codons] | amyA optimized [% codons/AA] |
|---|---|---|---|---|---|---|
| | Arg_CGG | 0 | 2 | 20.0 | 0 | 0.0 |
| | Arg_AGA | 0 | 0 | 0.0 | 0 | 0.0 |
| | Arg_AGG | 0 | 3 | 8.1 | 0 | 0.0 |
| S | Ser_TCT | 21 | 4 | 10.8 | 8 | 21.6 |
| | Ser_TCC | 44 | 9 | 24.3 | 16 | 43.2 |
| | Ser_TCA | 0 | 4 | 10.8 | 0 | 0.0 |
| | Ser_TCG | 14 | 10 | 27.0 | 5 | 13.5 |
| | Ser_AGT | 0 | 4 | 10.8 | 0 | 0.0 |
| | Ser_AGC | 21 | 6 | 16.2 | 8 | 21.6 |
| T | Thr_ACT | 30 | 9 | 22.5 | 12 | 30.0 |
| | Thr_ACC | 70 | 13 | 32.5 | 28 | 70.0 |
| | Thr_ACA | 0 | 10 | 25.0 | 0 | 0.0 |
| | Thr_ACG | 0 | 8 | 20.0 | 0 | 0.0 |
| V | Val_GTT | 27 | 5 | 16.1 | 8 | 25.8 |
| | Val_GTC | 54 | 12 | 38.7 | 17 | 54.8 |
| | Val_GTA | 0 | 4 | 12.9 | 0 | 0.0 |
| | Val_GTG | 19 | 10 | 32.3 | 6 | 19.4 |
| W | Trp_TGG | 100 | 12 | 100.0 | 12 | 100.0 |
| Y | Tyr_TAT | 0 | 11 | 31.4 | 0 | 0.0 |
| | Tyr_TAC | 100 | 24 | 68.6 | 35 | 100.0 |

Subsequently, a completely new nucleotide coding sequence is created by random distribution of the proposed number of synonymous codons (Table 6) for each amino acid in the original amyA peptide.

The native amyA gene contains a 'TGA' stop codon. In all amyA constructs made, the 5'-TGA-3' translational termination sequence was replaced by 5'-TAAA-3' followed by the 5'-TTAATTAA-3' of the PacI restriction site.

This resulted in a modified coding sequence (or synonymous coding sequence or optimized synthetic sequence) as depicted in Table 6. The optimized synthetic amyA sequence, resulting from the process described above, is indicated in SEQ ID NO 32. Secondary structures in the modified coding sequence was checked using the Clone Manager 7 program (Sci. Ed. Central: Scientific & Educational software, version 7.02) for possible occurrence of harmful secondary structures.

3.2: Choice of a Modified Translational Initiation Sequences

In this example, the strong amyA promotor is applied for over-expression of the alpha amylase enzyme in *A. niger* using pGBFIN-based expression constructs. The translational initiation sequence including ATG start codon of PamyA is 5'-GGCATTTATG ATG-3' (SEQ ID NO: 183) or 5'-GAAGGCATTT ATG-3' (SEQ ID NO: 184), dependent on which ATG is selected as start codon. The translational initiation sequence of PamyA has been modified into 5'-CAC-CGTCAAA ATG-3' (SEQ ID NO: 185). This replacement has been done in the sequences of SEQ ID NO. 33 and SEQ ID NO. 34. As a result of this, the expression constructs pGBFINFUA-2 and pGBFINFUA-3, have a modified translational initiation sequence according to the invention.

3.3: Combination of at Least One of the Modifications Made in 3.1 and 3.2

Expression of the sequence coding for the polypeptide to be produced may be improved by optimizing the codon usage and/or control DNA sequences comprising a consensus translational initiator sequence and/or optimal translational termination sequence. A series of 3 constructs (Table 7) was constructed to test a number of embodiments of the invention.

TABLE 7

Overview of improved expression constructs using at least one of the modified sequences.

| SEQ ID NO | Translational initiation sequence | Codon usage | Translation termination sequence |
|---|---|---|---|
| 31 | w.t. | w.t. | Modified (TAA ATTAA) |
| 33 | variant 1 (CACCGT-CAAA) (SEQ ID NO: 22) | w.t. | Modified (TAA ATTAA) |
| 34 | variant 1 (CACCGT-CAAA) (SEQ ID NO: 22) | modified | Modified (TAA ATTAA) |

Example 4

Construction of Modified Expression Vectors and Testing them in *A. niger*

4.1. Construction of Modified pla1 Expression Vectors Expressing *A. Oryzae* Phospholipase A1 According Example 2.1-2.5

The DNA sequence of the cloned EcoRI-SnaBI fragment of pGBFINPLA-1a is shown as SEQ ID NO 8. The DNA sequences of EcoRI fragments comprising variants for the translational initiation sequence of the glucoamylase promoter are shown as SEQ ID NO 9 and SEQ ID NO 10. These modified gene fragments were completely synthesized and the sequence was confirmed by sequence analysis.

Figure 3:
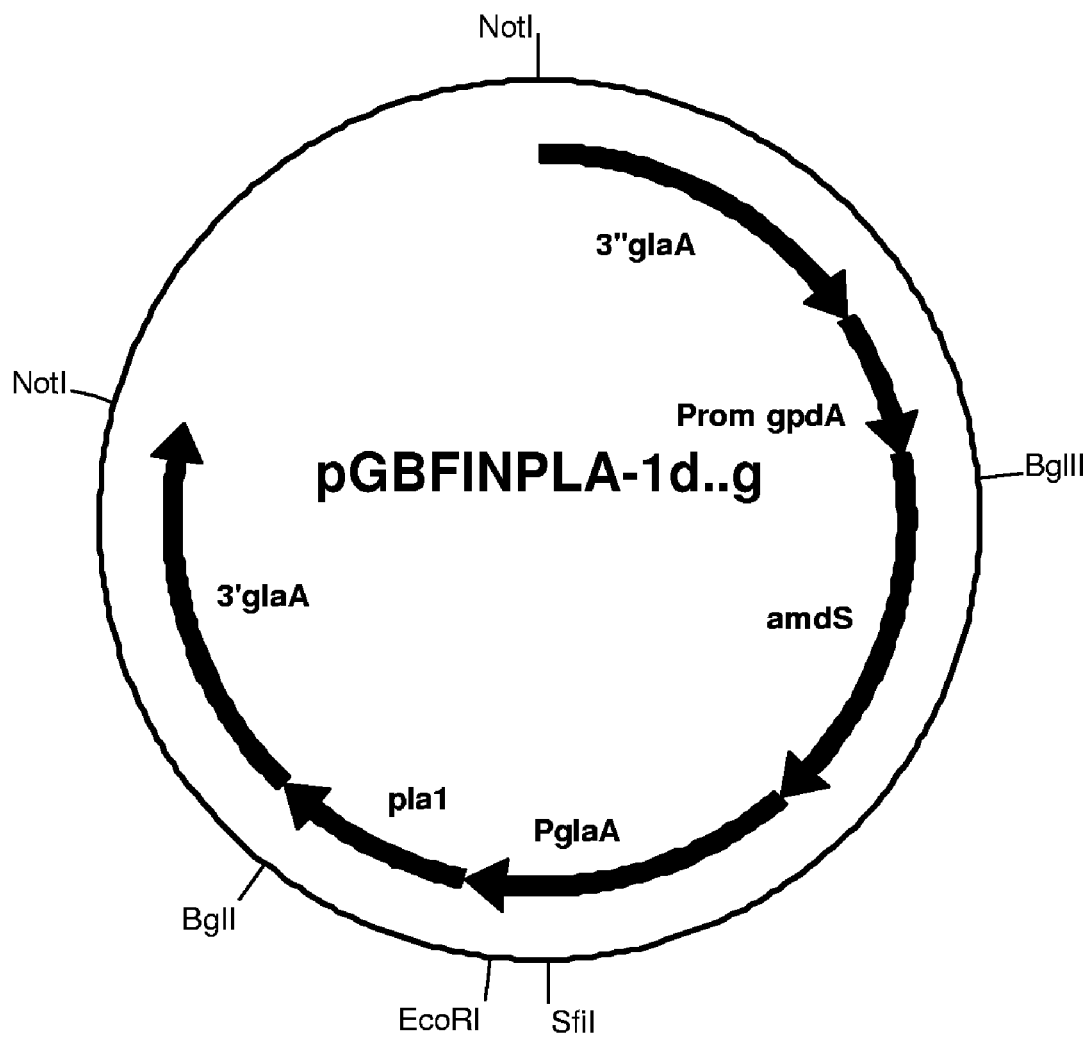
FIG. 3 depicts a plasmid map of expression vectors pGBFINPLA-1d through pGBFINPLA1h. Indicated are the glaA flanking regions relative to the variant sequences of the glaA promoter and the *A. oryzae* genomic pla1 gene encoding phospholipase A1. The *E. coli* DNA can be removed by digestion with restriction enzyme NotI, prior to transformation of the *A. niger* strains.

For cloning these modified sequence variants in an expression vector, all synthetic gene fragments were digested with EcoRI and introduced in the large fragment of an EcoRI digested pGBFINPLA-1a vector (FIG. 2), generating variant expression vectors of pGBFINPLA-1a. After checking for the proper orientation of the EcoRI fragment, the variant expression constructs were named pGBFINPLA1b and pGBFIN-PLA-1c as described below in Table 8. FIG. 3 is also providing a representative map for plasmid pGBFINPLA-1b and pGBFINPLA-1c.

The DNA sequence of 5 other synthetic sequence variants comprising part of the glucoamylase promoter, the pla1 signal sequence, the mature peptide of phospholipase A1 and the translational termination sequence around the stop codon are shown as SEQ ID NO 11 until SEQ ID NO 14 and SEQ ID NO 35. These 5 modified gene fragments were completely synthesized by design and synthesis of overlapping polynucleotides and subsequent assembly of the double-stranded sequence from a number of overlapping polynucleotides. The sequence was confirmed by sequence analysis.

For cloning these modified sequence variants in an expression vector, all synthetic gene fragments were digested with EcoRI and SnaBI and introduced in the large fragment of an EcoRI and NruI digested pGBFINPLA-1a vector (FIG. 2), generating variant expression vectors pGBFINPLA-1d until pGBFINPLA-1h as described below in Table 8. A representative map for the plasmids pGBFINPLA-1d until pGBFINPLA-1h is provided in FIG. 3.

amino acid sequence as identified in SEQ ID NO: 15, representing an *A. oryzae* phospholipase A1 with a modified signal sequence.

4.2. Construction of Modified amyA Expression Vectors Expressing *A. Niger* Alpha-Amylase According Example 3.1-3.3

The DNA sequence of the XhoI-PacI fragment of pGBFINFUA-1 (FIG. 4) is shown as SEQ ID NO 31 and comprises the wild-type amyA promoter and wild-type amyA cDNA sequence with a modified translation stop sequence (TAAA). The DNA sequence comprising a variant for the translational initiation sequence of the alpha-amylase promoter is shown as SEQ ID NO 33. The DNA sequence comprising a variant of the translational initiation sequence of the alpha-amylase promoter combined with a codon optimized coding sequence for alpha-amylase encoding amyA gene is shown as SEQ ID NO 34. These modified gene fragments were completely synthesized in vitro and the sequence was confirmed by sequence analysis.

For cloning these modified sequence variants in an expression vector, all synthetic gene fragments were digested with

TABLE 8

| Plasmid-name | SEQ ID NO | Translation start region | Codon | Translation stop |
|---|---|---|---|---|
| PGBFINPLA-1a | 8 | CACCTCAGCA<br>ATG TTT AGT CTC<br>(SEQ ID NO: 186) | w.t | TAG TAC |
| PGBFINPLA-1b | 9 | CACCGTCAAA<br>ATG TTT AGT CTC<br>(SEQ ID NO: 187) | w.t | TAG TAC |
| PGBFINPLA-1c | 10 | CGCAGTCAAG<br>ATG TTT AGT CTC<br>(SEQ ID NO: 188) | w.t | TAG TAC |
| PGBFINPLA-1d | 11 | CACCTCAGCA<br>ATG TTC TCT CTC<br>(SEQ ID NO: 189) | modified | Modified<br>(TAA ATA) |
| PGBFINPLA-1e | 12 | CACCGTCAAA<br>ATG TTC TCT CTC<br>(SEQ ID NO: 190) | modified | Modified<br>(TAA ATA) |
| PGBFINPLA-1f | 13 | CGCAGTCAAG<br>ATG TTC TCT CTC<br>(SEQ ID NO: 191) | modified | Modified<br>(TAA ATA) |
| PGBFINPLA-1g | 14 | CACCGTCAAA<br>ATG GCT TCC TTC<br>(SEQ ID NO: 24) | modified | Modified<br>(TAA ATA) |
| pGBFINPLA-1h | 35 | CTCCTTCACC<br>ATG TTC TCT CTC<br>(SEQ ID NO: 192) | modified | Modified<br>(TAA ATA) |

The translated sequences of the pla1 coding sequences of plasmid pGBFINPLA-1a until pGBFINPLA-1f and pGBFINPLA-1h are according the amino acid sequence as identified in SEQ ID NO: 3, representing the wild-type *A. oryzae* phospholipase A1. The translated sequence of the pla1 coding sequence of plasmid pGBFINPLA-1g is according the XhoI and PacI and introduced in the large fragment of an XhoI and PacI digested pGBFINFUA-1 vector (FIG. 4), generating variant expression vectors. After checking the integration of the correct fragment, the variant expression constructs were named pGBFINFUA-2 and pGBFINFUA-3 as described below in Table 9.

TABLE 9

Modified expression constructs for alpha-amylase expression in A. niger

| Plasmid-name | SEQ ID NO | Translation start region | Codon | Translation stop |
|---|---|---|---|---|
| pGBFINFUA-1 | 31 | Wild type (GAAGGCATTT ATG) (SEQ ID NO: 184) | w.t | Modified (TAA ATA) |
| pGBFINFUA-2 | 33 | Modified (CACCGTCAAA ATG) (SEQ ID NO: 185) | w.t | Modified (TAA ATA) |
| pGBFINFUA-3 | 34 | Modified (CACCGTCAAA ATG) (SEQ ID NO: 185) | Modified | Modified (TAA ATA) |

The translated sequences of the amyA coding sequences of plasmid pGBFINFUA-1 to pGBFINFUA-3 are according to the amino acid sequence as depicted in SEQ ID NO: 30, representing the wild-type *A. niger* alpha-amylase.

Figure 5:
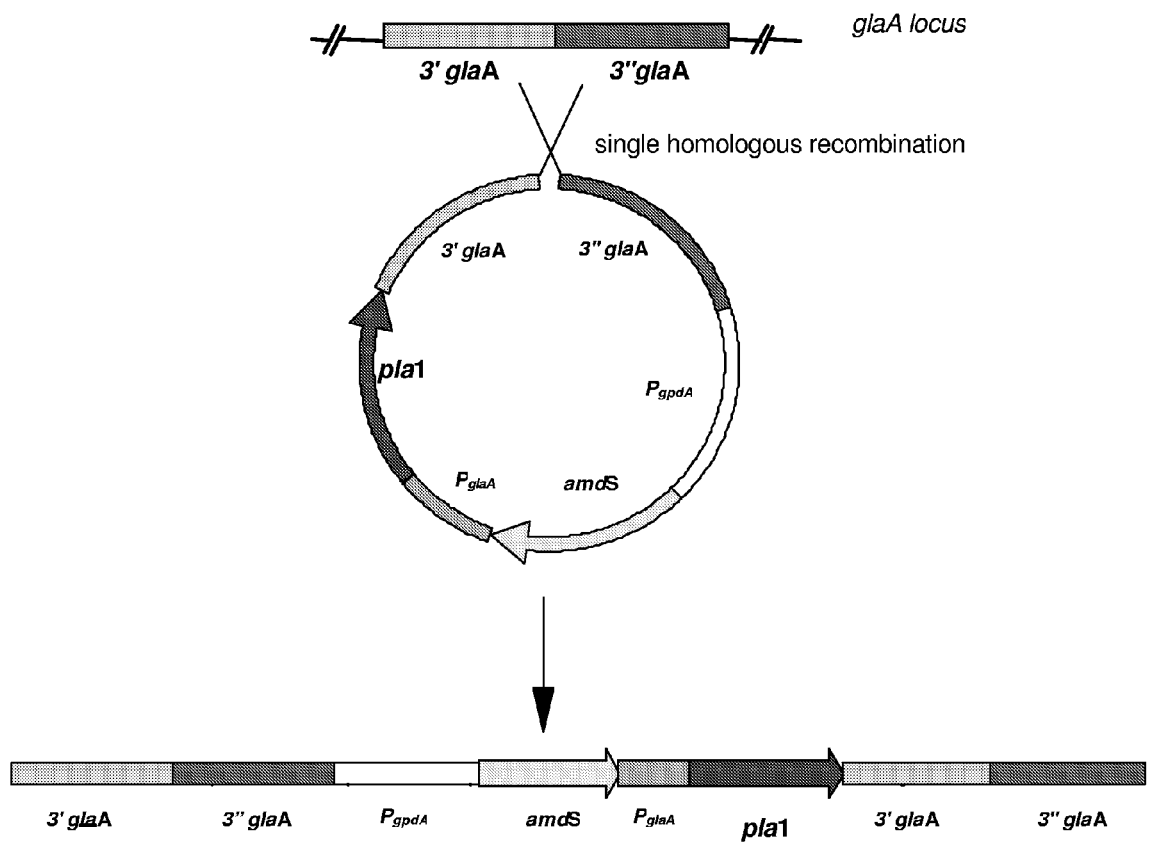
FIG. 5 depicts a schematic representation of integration through single homologous recombination. The expression vector comprises the selectable amdS marker, and the glaA promoter connected to the pla1 gene. These features are flanked by homologous regions of the glaA locus (3' glaA and 3" glaA, respectively) to direct integration at the genomic glaA locus.

4.3. Expression in *A. Niger* of Wild-Type and Modified Expression Constructs of *A. oryzae* Phospholipase A1 Using the pGBFINPLA-Vectors and of *A. Niger* Alpha-Amylase Using the pGBFINFUA-Vectors The pGBFINPLA- and pGBFINFUA-expression constructs, prepared in the former paragraph, were introduced in *A. niger* by transformation as described below and according to the strategy depicted in FIG. 5.

In order to introduce the eight pGBFINPLA-vectors (Table 8) in WT 2 and the three pGBFINFUA-vectors (Table 9) in WT 3, a transformation and subsequent selection of transformants was carried out as described in WO98/46772 and WO99/32617. In brief, linear DNA of the pGBFIN constructs was isolated and used to transform *A. niger*. Transformants were selected on acetamide media and colony purified according standard procedures. Colonies were diagnosed for integration at the glaA locus and for copy number using PCR. Five to ten independent transformants of each pGBFIN construct with similar estimated copy numbers (low copy: 1-2) were selected and named using the number of the transforming plasmid, as for example PLA-1a-1, PLA-1b-2 and FUA-1-1, FUA-3-1, respectively.

The selected PLA- and FUA-strains and *A. niger* WT 2 and WT 3 were used to perform shake flask experiments in 100 ml of the medium as described above for each of the protein products at 34° C. and 170 rpm in an incubator shaker using a 500 ml baffled shake flask. After 2, 3, 4, 5 and/or 6 days of fermentation, samples were taken. In a first step, the pla1 and amyA over-expression was measured by Northern blot analysis of the transformants of *A. niger* WT 2 and WT 3 and WT2 and WT 3 themselves. The collected mycelium was used for isolation of RNA (as described in WO99/32617) and Northern blot analysis following the standard procedures of Northern blot analysis (Sambrook et al., 1989). For all transformants of the wild-type pla1 gene, but not for WT2 itself, a strong and comparable hybridization signal was detected for the pla1 mRNA level (data not shown). This indicates that the transcriptional control of the pla1 gene by the glucoamylase promoter in all transformed strains of pGBFINPLA-1a until pGBFINPLA-1c was intact and unchanged compared to the wild-type glaA promoter. Additionally, pla1 over-expression of the pla1 modified constructs was measured by Northern blot analysis of the concerning PLA transformants of *A. niger* WT 2 and WT2 itself. For all transformants of the modified synthetic pla1 genes, but not for WT2 itself, a strong and comparable hybridization signal was detected (data not shown). This indicates that the transcriptional control of the optimized pla1 genes by the glucoamylase promoter in all transformed strains of pGBFINPLA-1d until pGBFINPLA-1h was intact and that the synthetic pla1 genes were expressed.

In a similar way, the amyA over-expression of the native and modified constructs was measured by Northern blot analysis of the concerning FUA transformants of *A. niger* WT 3 and WT3 itself, using a (universal) probe located in the 3'-untranslated region of the glucoamylase terminator used in all three expression constructs. For all transformants of amyA constructs, a strong and comparable hybridization signal was detected (data not shown). This indicates that the transcriptional control of the optimized amyA genes by the alpha-amylase promoter in all transformed strains of pGBFIN-FUA-1 to pGBFINFUA-3 was intact and that the synthetic amyA genes were expressed.

Figure 7:
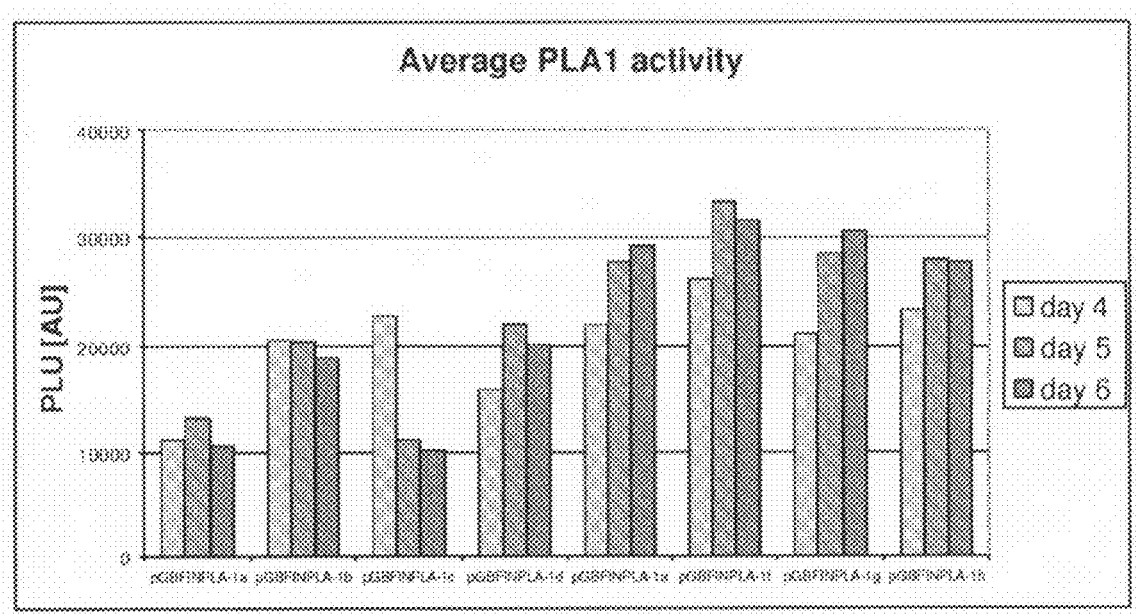
FIG. 7 depicts phospholipase A1 activity in culture broth for *A. niger* strains expressing eight different constructs (pGBFINPLA-1a-h). Depicted is the average phospholipase A1 activity in culture broth of *A. niger* strains expressing a native (pGBFINPLA-1a) or modified pla1 constructs (pGBFINPLA-1b-h), wherein the translation initiation sequence and/or the translation termination sequence and/or the codon usage have been modified according to the method of the invention. Phospholipase activities are depicted in arbitrary units [AU] and are the average of at least five independently isolated and cultivated transformants, named as indicated (Table 6), measured after the cultivation time as indicated.

The production of phospholipase A1 polypeptide was measured in all *A. niger* PLA transformants. As can be seen in FIG. 7, a positive effect of the use of a modified translation initiation site (variant 1 and variant 2) on phospholipase production can be observed using the glucoamylase promoter. Similarly, a positive effect of modification of codon usage and the translation stop sequence on phospholipase production was observed. A summary of the results is shown in Table 10 below. This indicates clearly how a single modification or a combination of modifications of the invention, for example a modified translation initiation sequence, such as variant 1, 2 or the variant described in U.S. Pat. No. 6,461,837 B1, and/or a modified codon usage and/or a modified translation stop sequence can be used to improve the yield of production of the phospholipase A1 in *A. niger*.

TABLE 10

Relative average phospholipase activities compared to wild-type construct for modified pla1 control and coding sequences (as concluded from FIG. 7).

Figure 8:
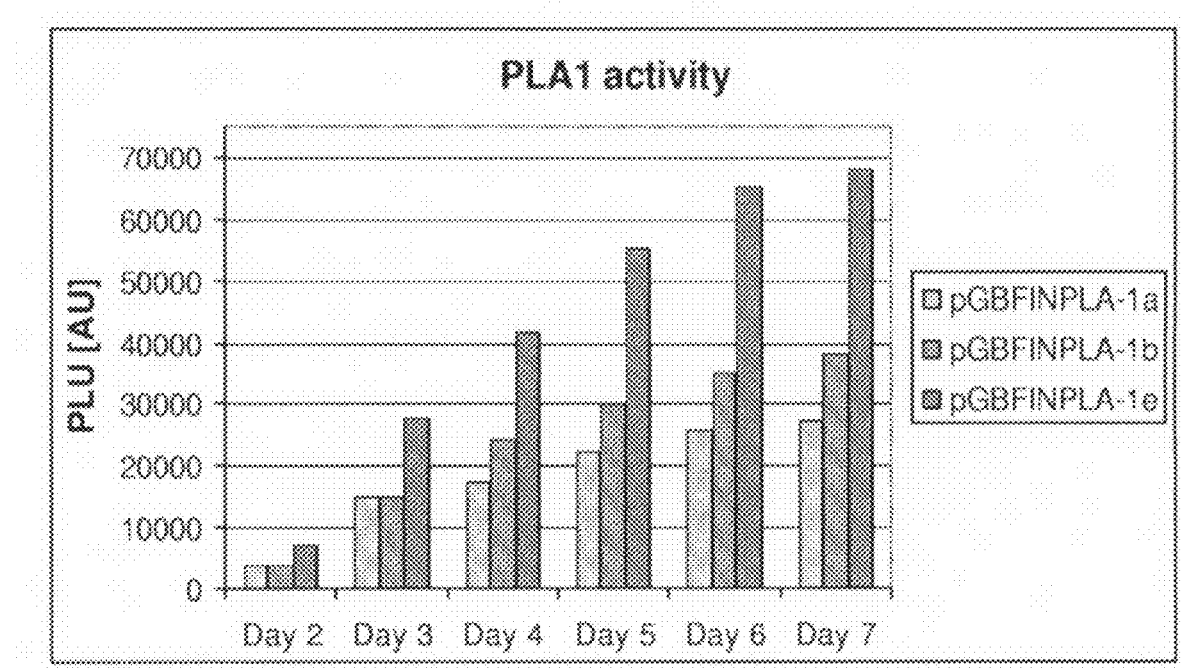
FIG. 8 depicts Phospholipase A1 activity in culture broth for *A. niger* strains expressing three different constructs. Depicted is the phospholipase A1 activity in culture broth of three *A. niger* strains expressing a native (pGBFINPLA-1a) or modified pla1 construct, wherein the translation initiation sequence and the translation termination sequence (pGBFIN-PLA-1b) and the translation initiation sequence, the translation termination sequence and the codon usage (pGBFIN-PLA-1e) were modified according a method of the invention. Phospholipase activities are depicted in arbitrary units [AU] for 2-copy pla1 transformants, named as indicated (Table 6), and measured after the cultivation time indicated.

| Plasmid name | SEQ ID NO | Translational initiator sequence | Translational initiator coding sequence | Optimized codon frequency | Translational termination sequence | Average production FIG. 7 | Average production FIG. 8 |
|---|---|---|---|---|---|---|---|
| PGBFINPLA-1a | 8 | CACCTCAGCA (SEQ ID NO: 193) | w.t | w.t | w.t | 100% | 100% |
| PGBFINPLA-1b | 9 | CACCGTCAAA (SEQ ID NO: 22) | w.t | w.t | w.t | 170% | 130% |
| PGBFINPLA-1c | 10 | CGCAGTCAAG (SEQ ID NO: 23) | w.t | w.t | w.t | 130% | |
| PGBFINPLA-1d | 11 | CACCTCAGCA (SEQ ID NO: 193) | TTCTCTCTC | modified | TAAATA | 170% | |
| PGBFINPLA-1e | 12 | CACCGTCAAA (SEQ ID NO: 22) | TTCTCTCTC | modified | TAATA | 230% | 240% |
| PGBFINPLA-1f | 13 | CGCAGTCAAG (SEQ ID NO: 23) | TTCTCTCTC | modified | TAATA | 260% | |
| PGBFINPLA-1g | 14 | CACCGTCAAA (SEQ ID NO: 22) | GCTTCCTTC (SEQ ID NO: 21) | modified | TAATA | 230% | |
| pGBFINPLA-1h | 35 | U.S. Pat. No. 6,461,837 B1 | TTCTCTCTC | modified | TAATA | 230% | |

As can be learned from FIG. 8, also in a multi-copy (2) situation the improvement clearly can be found. This indicated clearly how a single modification or a combination of modifications of the invention, for example a modified translation initiation sequence and/or a modified codon usage and/or a modified translation stop sequence can be used for improved production of the phospholipase A1 in *A. niger*.

Figure 9:
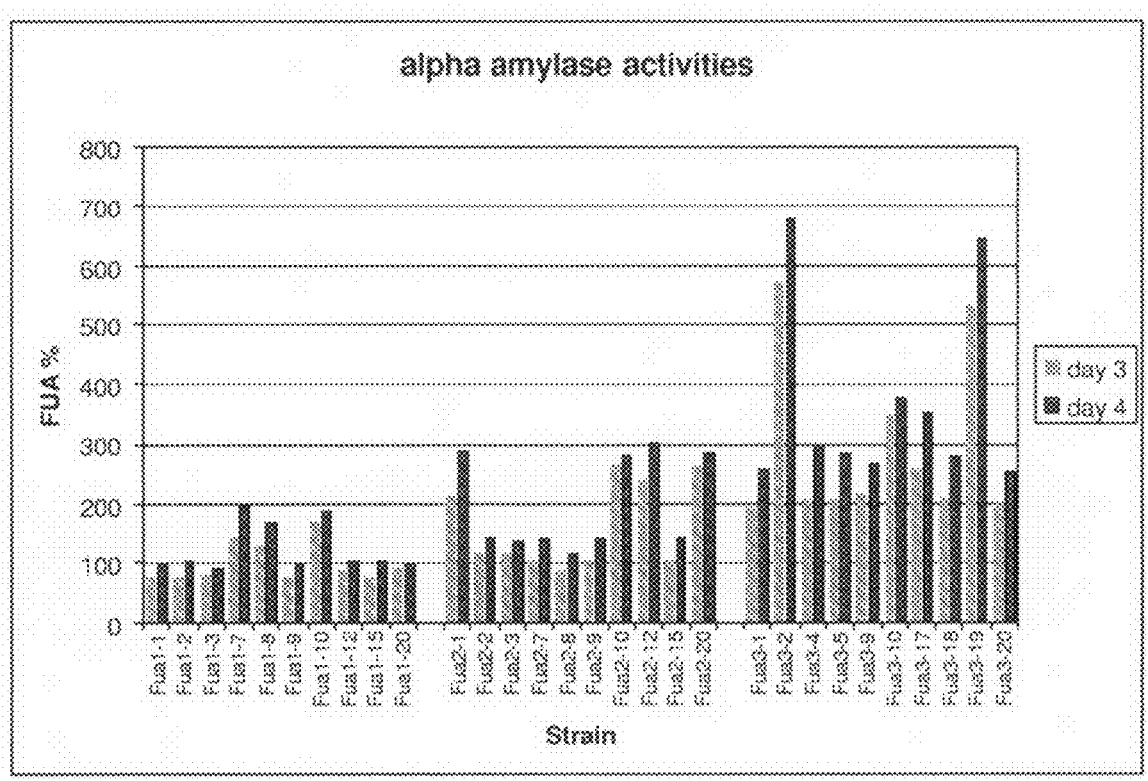
FIG. 9 depicts Alpha-amylase activity in culture broth for *A. niger* strains expressing three different constructs. Depicted is the alpha-amylase activity in culture broth of *A. niger* strains expressing a native (pGBFINFUA-1) or modified amyA construct, wherein the translation initiation sequence and the translation termination sequence were modified (pGBFINFUA-2) and the translation initiation sequence, the translation termination sequence and the codon usage were modified (pGBFINFUA-3) according a method of the invention. Alpha-amylase activities are depicted in relative units [AU], with the average of the 7 one-copy strains of the FUA1 group of 10 strains at day 4 set at 100%. The ten transformants per group indicated are independently isolated and cultivated transformants, named as indicated in Table 9, and measured the cultivation time as indicated.

The production of alpha-amylase was measured in all three different *A. niger* FUA transformants. As can be learned from FIG. 9, a positive effect of the use of a modified translation initiation site (variant 1) on alpha-amylase production can be observed, using the alpha-amylase promoter. Additionally, a positive and synergistic effect of combination of a modified translation initiation site (variant 1) with a modified codon usage and a modified translation stop sequence on improved alpha-amylase production was observed. These results indicate clearly the universal effect of the modification since both phospholipase production and alpha-amylase production can be improved using a method of the invention. Additionally, multiple promoters could be improved using a modified translation initiation site of the invention. Clearly, these examples show how a single or a combination of modifications of the invention, for example a modified translation initiation sequence, a modified codon usage and/or a modified translation stop sequence can be used for improved production of the alpha-amylase in *A. niger* or any other protein of interest in a filamentous fungus.

The invention claimed is:

1. A nucleotide sequence comprising:
a synonymous nucleotide coding sequence with optimized codon frequency such that a native codon has been exchanged with a synonymous codon, said synonymous codon encoding the same amino acid as the native codon and having a higher frequency in codon usage as defined in Table 1 than the native codon;
wherein the optimized codon frequency is such that at least 10% of the native codons have been exchanged with a synonymous codon, the synonymous codon changing the codon frequency such that the value of the absolute difference between the percentage for said synonymous codon in said frequency and the listed optimal percentage becomes smaller after modification, applying the following list of optimal percentages; cysteine by TGC (100%); phenylalanine by TTC (100%); histidine by CAC (100%); lysine by AAG (100%); asparagine by AAC (100%); glutamine by CAG (100%); tyrosine by TAC (100%); alanine is encoded by GCT (38%) GCC (51%), or GCG (11%); aspartate by GAC (64%); glutamate by GAG (74%); glycine by GGT (49%), GGC (35%), GGA (16%); isoleucine by ATT (27%), ATC (73%); leucine by TTG (13%), CTT (17%), CTC (38%), CTG (32%); proline by CCT (36%), CCC (64%); arginine by CGT (49%), CGC (51%); serine by TCT (21%), TCC (44%), TCG (14%), AGC (21%); threonine by ACT (30%), ACC (70%) and/or valine by GTT (27%), GTC (54%), GTG (19%); and optionally said nucleotide sequence comprises control sequences comprising:
one translational termination sequence orientated in 5' towards 3' direction selected from the following list of sequences: TAAG, TAGA and TAAA, and/or
one translational initiator coding sequence orientated in 5' towards 3' direction selected from the following list of sequences: GCTACCCCC; GCTACCTCC; GCTACCCTC; GCTACCTTC; GCTCCCCCC; GCTCCCTCC; GCTCCCCTC; GCTCCCTTC; GCTGCCCCC; GCTGCCTCC; GCTGCCCTC; GCTGCCTTC; GCTTCCTCC; GCTTCCCCC; GCTTCCCTC; and GCTTCCTTC (SEQ ID NO:21)

TABLE 1

Optimal filamentous fungal codon frequency for synonymous codons in %

|     | .T.       | .C.       | .A.       | .G.       |     |
|-----|-----------|-----------|-----------|-----------|-----|
| T.. | Phe<br>0  | Ser<br>21 | Tyr<br>0  | Cys<br>0  | ..T |
| T.. | Phe<br>100| Ser<br>44 | Tyr<br>100| Cys<br>100| ..C |
| T.. | Leu<br>0  | Ser<br>0  | Stop<br>100| Stop<br>0| ..A |

TABLE 1-continued

Optimal filamentous fungal codon frequency for synonymous codons in %

|     | .T.        | .C.       | .A.        | .G.        |     |
|-----|------------|-----------|------------|------------|-----|
| T.. | Leu<br>13  | Ser<br>14 | Stop<br>0  | Trp<br>100 | ..G |
| C.. | Leu<br>17  | Pro<br>36 | His<br>0   | Arg<br>49  | ..T |
| C.. | Leu<br>38  | Pro<br>64 | His<br>100 | Arg<br>51  | ..C |
| C.. | Leu<br>0   | Pro<br>0  | Gln<br>0   | Arg<br>0   | ..A |
| C.. | Leu<br>32  | Pro<br>0  | Gln<br>100 | Arg<br>0   | ..G |
| A.. | Ile<br>27  | Thr<br>30 | Asn<br>0   | Ser<br>0   | ..T |
| A.. | Ile<br>73  | Thr<br>70 | Asn<br>100 | Ser<br>21  | ..C |
| A.. | Ile<br>0   | Thr<br>0  | Lys<br>0   | Arg<br>0   | ..A |
| A.. | Met<br>100 | Thr<br>0  | Lys<br>100 | Arg<br>0   | ..G |
| G.. | Val<br>27  | Ala<br>38 | Asp<br>36  | Gly<br>49  | ..T |
| G.. | Val<br>54  | Ala<br>51 | Asp<br>64  | Gly<br>35  | ..C |
| G.. | Val<br>0   | Ala<br>0  | Glu<br>26  | Gly<br>16  | ..A |
| G.. | Val<br>19  | Ala<br>11 | Glu<br>74  | Gly<br>0.  | ..G |

2. A nucleotide sequence according to claim 1, wherein the codon fitness of the synonymous nucleotide coding sequence with optimized codon frequency has a fitness value that is at least 70%, where the codon fitness is the calculated by means of the following function:

$$fit_c(g) = 100 - \frac{1}{|g|} \cdot \sum_{k=1}^{|g|} |r_c^{target}(c(k)) - r_c^g(c(k))| \cdot 100$$

where g symbolizes a nucleotide coding sequence, |g| its length, g(k) its k-th codon, $r_c^{t\ arg\ et}(c(k))$ is a desired ratio of codon c(k) and $r_c^g(c(k))$ an actual ratio in the nucleotide coding sequence g.

3. A synonymous nucleotide coding sequence with a codon fitness as defined in claim 2, wherein said synonymous nucleotide coding sequence is reverse engineered from an amino acid sequence.

4. A nucleotide sequence comprising a synonymous nucleotide coding sequence according to claim 1, wherein the synonymous nucleotide coding sequence comprises a signal sequence.

5. A nucleotide sequence comprising at least one intron and a synonymous nucleotide coding sequence according to claim 1.

6. A nucleotide sequence, according to claim 1,
comprising a translational initiator sequence, said translational initiator sequence comprising the nucleic acid sequence as defined by the consensus translational initiator sequence: 5'-mwChkyCAmv-3' (SEQ ID NO: 16), using ambiguity codes for nucleotides: m (A/C); r (A/G); w (A/T); s (C/G); y (C/T); k (G/T); v (A/C/G); h (A/C/T); d (A/G/T); b (C/G/T); n (A/C/G/T).

7. A nucleotide sequence according to claim 1, comprising a translational initiator sequence, wherein the translational initiator sequence is 5'-CACCGTCAAA-3' (SEQ ID NO: 22) or 5'-CGCAGTCAAG-3' (SEQ ID NO: 23).

8. A nucleic acid construct comprising a nucleotide sequence according to claim 1.

9. A filamentous fungal host cell comprising at least one copy of the nucleic acid construct of claim 8.

10. A filamentous fungal host cell according to claim 9, wherein the coding and/or control sequences present in the nucleic acid construct are native to the host cell before modification of the coding and/or control sequences.

11. A filamentous fungal host cell according to claim 9, wherein the coding and/or control sequences present in the nucleic acid construct are heterologous to the host cell before modification of the coding and/or control sequences.

12. A filamentous fungal host cell according to claim 9 and comprising a given copy number of the nucleic acid construct, wherein the expression of the product encoded by said nucleic acid construct is enhanced as compared to the production of the same product encoded by the corresponding nucleic acid construct comprising the corresponding native nucleotide sequences, said corresponding nucleic acid construct being present in the same copy number in the corresponding filamentous fungal host cell.

13. A filamentous fungal host cell according to claim 9, which is an *Aspergillus, Trichoderma, Fusarium, Chrysporum* or *Penicillium* species.

14. An *Aspergillus, Trichoderma, Chrysosporum* or *Penicillium* host cell according to claim 13, which is an *Aspergillus niger, Aspergillus oryzae, Aspergillus sojae, Aspergillus terreus*, or *Trichoderma reesei*, or *Chrysosporum lucknowense*, or *Penicillium chrysogenum*.

15. A method for producing a compound of interest and optionally purifying it by using the filamentous fungal host cell of claim 9, comprising:
cultivating said filamentous fungal host cell in a nutrient medium suitable for production of the compound of interest; and
recovering the compound of interest from the nutrient medium of the filamentous fungal host cell.

16. A method according to claim 15, wherein the yield of the compound of interest produced by the filamentous fungal host cell of the invention comprising a given copy number of the nucleic acid construct is increased by at least 10% as compared to the production of the same compound of interest produced by the corresponding filamentous fungal host cell comprising the corresponding nucleic acid construct comprising the corresponding native nucleotide sequences, said corresponding nucleic acid construct being present in the same copy number in the corresponding filamentous fungal host cell.

17. A method according to claim 15, wherein production of the compound of interest in the filamentous fungal cell results in a production of 0.1 g per liter of the compound of interest.

18. A method for producing a nucleotide sequence comprising:
producing a synonymous nucleotide coding sequence with optimized codon frequency
as defined in claim 1, and optionally
operably linking said synonymous nucleotide coding sequence to a control sequence.

19. A nucleotide sequence, according to claim 1, comprising a translational initiator sequence, said consensus translational initiator sequence is one selected from the following list: 5'-mwChkyCAAA-3' (SEQ ID NO: 17), 5'-mwChky-CACA-3' (SEQ ID NO:18), and 5'-mwChkyCAAG-3' (SEQ ID NO: 19).

\* \* \* \* \*